US010912860B2

(12) United States Patent
Griffin et al.

(10) Patent No.: US 10,912,860 B2
(45) Date of Patent: Feb. 9, 2021

(54) CONTROLLABLE SELF-ANNEALING MICROGEL PARTICLES FOR BIOMEDICAL APPLICATIONS

(71) Applicant: THE REGENTS OF THE UNIVERSITY OF CALIFORNIA, Oakland, CA (US)

(72) Inventors: Donald R. Griffin, Los Angeles, CA (US); Westbrook Weaver, Los Angeles, CA (US); Tatiana Segura, Los Angeles, CA (US); Dino Di Carlo, Los Angeles, CA (US); Philip Scumpia, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 15/701,113

(22) Filed: Sep. 11, 2017

(65) Prior Publication Data
US 2017/0368224 A1  Dec. 28, 2017

Related U.S. Application Data

(60) Division of application No. 15/179,151, filed on Jun. 10, 2016, now abandoned, which is a continuation of
(Continued)

(51) Int. Cl.
*A61L 26/00* (2006.01)
*A61L 27/18* (2006.01)
(Continued)

(52) U.S. Cl.
CPC .............. *A61L 26/008* (2013.01); *A61K 9/06* (2013.01); *A61K 31/795* (2013.01); *A61K 47/62* (2017.08);
(Continued)

(58) Field of Classification Search
CPC ................ C04B 26/02; C04B 38/0058; C04B 2103/0062; C08L 5/08; C08L 71/02;
(Continued)

(56) References Cited

U.S. PATENT DOCUMENTS 4,726,877 A   2/1988   Fryd et al.
4,753,865 A   6/1988   Fryd et al.
(Continued)

FOREIGN PATENT DOCUMENTS

CN      1543339      11/2004
CN    104582747       4/2015
(Continued)

OTHER PUBLICATIONS

Burdick et al. (Tunable hydrogel-microsphere composites that modulate local inflammation and collagen bulking, Acta Biomaterialia, vol. 8:3218-3227 (May 29, 2012) (Year: 2012).*
(Continued)

*Primary Examiner* — Randall L Beane
(74) *Attorney, Agent, or Firm* — Vista IP Law Group LLP

(57) ABSTRACT

A microporous gel system for certain applications, including biomedical applications, includes an aqueous solution containing plurality of microgel particles including a biodegradable crosslinker. In some aspects, the microgel particles act as gel building blocks that anneal to one another to form a covalently-stabilized scaffold of microgel particles having interstitial spaces therein. In certain aspects, annealing of the microgel particles occurs after exposure to an annealing agent that is endogenously present or exogenously added. In some embodiments, annealing of the microgel particles requires the presence of an initiator such as exposure to light. In particular embodiments, the chemical and physical properties of the gel building blocks can be controlled to allow downstream control of the resulting assembled scaf-
(Continued)

fold. In one or more embodiments, cells are able to quickly infiltrate the interstitial spaces of the assembled scaffold.

1 Claim, 20 Drawing Sheets

Specification includes a Sequence Listing.

Related U.S. Application Data application No. PCT/US2015/040962, filed on Jul. 17, 2015.

(60) Provisional application No. 62/025,844, filed on Jul. 17, 2014, provisional application No. 62/059,463, filed on Oct. 3, 2014, provisional application No. 62/103,002, filed on Jan. 13, 2015.

(51) Int. Cl.
| | | |
|---|---|---|
| A61L 27/58 | (2006.01) | |
| A61K 47/62 | (2017.01) | |
| A61K 9/06 | (2006.01) | |
| A61K 31/795 | (2006.01) | |
| A61L 27/22 | (2006.01) | |
| A61L 27/52 | (2006.01) | |
| A61L 27/54 | (2006.01) | |
| A61L 27/56 | (2006.01) | |

(52) U.S. Cl.
CPC ......... *A61L 26/009* (2013.01); *A61L 26/0019* (2013.01); *A61L 26/0047* (2013.01); *A61L 26/0066* (2013.01); *A61L 26/0085* (2013.01); *A61L 27/18* (2013.01); *A61L 27/227* (2013.01); *A61L 27/52* (2013.01); *A61L 27/54* (2013.01); *A61L 27/56* (2013.01); *A61L 27/58* (2013.01); *A61L 2300/252* (2013.01); *A61L 2300/412* (2013.01); *A61L 2400/06* (2013.01); *A61L 2430/00* (2013.01); *A61L 2430/34* (2013.01)

(58) Field of Classification Search
CPC .. C08L 89/00; C08L 2205/04; C08L 2205/14; C08L 33/064; C08L 51/003; C12M 23/20; C12M 25/06; C12M 25/14; C12N 2539/10; C12N 5/0068; C12N 11/04; C12N 11/08; C12N 15/87; C12N 9/99; B82Y 30/00; B82Y 40/00; B82Y 15/00; B82Y 20/00; B82Y 25/00; B82Y 5/00; C08J 3/075; C08J 3/246; A61K 38/45; A61K 47/48853; A61L 2300/62; A61L 2430/38; A61L 27/00; A61L 27/04; A61L 27/10; A61L 27/18; A61L 27/20; A61L 27/36; A61L 27/502; A61L 27/52; A61L 27/54; A61L 27/56; B22F 2304/054; B82B 1/008; B82B 3/0095; C08B 37/0072; C08H 1/00; C09D 7/1291; C12Y 203/02013; Y10T 156/10; Y10T 428/298

See application file for complete search history.

(56) References Cited

U.S. PATENT DOCUMENTS

| | | |
|---|---|---|
| 5,102,597 A | 4/1992 | Roe et al. |
| 5,124,188 A | 6/1992 | Roe et al. |
| 5,213,580 A | 5/1993 | Slepian et al. |
| 5,575,815 A | 11/1996 | Slepian et al. |
| 5,843,156 A | 12/1998 | Slepian et al. |
| 5,854,382 A | 12/1998 | Loomis |
| 6,005,020 A | 12/1999 | Loomis |
| 6,007,833 A | 12/1999 | Chudzik et al. |
| 6,028,164 A | 2/2000 | Loomis |
| 6,063,061 A | 5/2000 | Wallace et al. |
| 6,066,325 A | 5/2000 | Wallace et al. |
| 6,156,345 A | 12/2000 | Chudzik et al. |
| 6,290,729 B1 | 9/2001 | Slepian et al. |
| 6,316,522 B1 | 11/2001 | Loomis et al. |
| 6,403,758 B1 | 6/2002 | Loomis |
| 6,534,560 B2 | 3/2003 | Loomis et al. |
| 6,602,975 B2 | 8/2003 | Hubbell |
| 6,660,827 B2 | 12/2003 | Loomis et al. |
| 6,669,827 B2 | 12/2003 | Austin |
| 6,924,370 B2 | 8/2005 | Chudzik et al. |
| 6,946,499 B2 | 9/2005 | Loomis et al. |
| 7,094,418 B2 | 8/2006 | Chudzik et al. |
| 7,109,255 B2 | 9/2006 | Loomis et al. |
| 7,442,384 B2 | 10/2008 | Loomis et al. |
| 7,547,445 B2 | 6/2009 | Chudzik et al. |
| 7,615,373 B2 | 11/2009 | Simpson et al. |
| 7,776,063 B2 | 8/2010 | Sawhney et al. |
| 7,785,617 B2 | 8/2010 | Shakesheff |
| 7,964,217 B2 | 6/2011 | Harris |
| 8,277,832 B2* | 10/2012 | Detamore ............ C12N 5/0075 424/423 |
| 8,318,193 B2 | 11/2012 | Ratner et al. |
| 8,357,378 B2 | 1/2013 | Wallace et al. |
| 8,557,288 B2 | 10/2013 | Elbert et al. |
| 8,603,511 B2 | 12/2013 | Wallace et al. |
| 8,927,022 B2 | 1/2015 | Maginness et al. |
| 9,234,171 B2 | 1/2016 | Lee et al. |
| 2002/0091229 A1 | 7/2002 | Hubbell |
| 2002/0176880 A1 | 11/2002 | Cruise et al. |
| 2004/0241203 A1 | 12/2004 | Shakesheff et al. |
| 2005/0119762 A1 | 6/2005 | Zilla et al. |
| 2006/0147443 A1* | 7/2006 | Schense ............ A61K 38/1825 424/94.63 |
| 2006/0257485 A1 | 11/2006 | Kumacheva |
| 2007/0141105 A1 | 6/2007 | Stein et al. |
| 2007/0167541 A1 | 7/2007 | Ruberti et al. |
| 2007/0190107 A1* | 8/2007 | Tosatti ................. A61L 27/34 424/423 |
| 2008/0193536 A1* | 8/2008 | Khademhosseini ........................ A61K 35/545 424/486 |
| 2009/0294049 A1 | 12/2009 | Udipi et al. |
| 2009/0311324 A1 | 12/2009 | Steinfeld et al. |
| 2010/0036503 A1 | 2/2010 | Chen et al. |
| 2011/0087152 A1 | 4/2011 | David et al. |
| 2011/0256628 A1 | 10/2011 | Galperin et al. |
| 2012/0015440 A1 | 1/2012 | Otsuka et al. |
| 2012/0114615 A1 | 5/2012 | Burdick et al. |
| 2012/0156259 A1 | 6/2012 | Rau et al. |
| 2012/0202263 A1 | 8/2012 | Blakely et al. |
| 2012/0308508 A1 | 12/2012 | Saunders et al. |
| 2013/0143056 A1 | 6/2013 | Swan et al. |
| 2013/0228530 A1 | 9/2013 | Di et al. |
| 2013/0233420 A1 | 9/2013 | Di et al. |
| 2014/0112960 A1 | 4/2014 | Lin |
| 2014/0120078 A1 | 5/2014 | Wallace et al. |
| 2014/0230909 A1 | 8/2014 | Di et al. |
| 2015/0071997 A1 | 3/2015 | Garcia et al. |
| 2015/0104427 A1 | 4/2015 | Segura |
| 2015/0202305 A1 | 7/2015 | Maynard et al. |
| 2015/0290362 A1 | 10/2015 | Douglas et al. |
| 2015/0359752 A1 | 12/2015 | Lu et al. |
| 2016/0279283 A1 | 1/2016 | Griffin |
| 2018/0078671 A1* | 3/2018 | Griffin ............... A61K 47/62 |
| 2019/0151497 A1* | 5/2019 | Griffin ............... A61K 31/795 |
| 2020/0085859 A1* | 3/2020 | Griffin ............... A61L 27/58 |

FOREIGN PATENT DOCUMENTS

| | | |
|---|---|---|
| EP | 1041970 A1 | 10/2000 |
| EP | 1063975 A1 | 1/2001 |
| EP | 1063975 B1 | 5/2005 |
| EP | 2542620 A1 | 1/2013 |

(56) References Cited

FOREIGN PATENT DOCUMENTS

| | | | | |
|---|---|---|---|---|
| EP | 1041970 | B1 | 7/2013 | |
| EP | 2542620 | B1 | 6/2016 | |
| GB | 2431104 | A | 4/2007 | |
| JP | 2004-523484 | | 8/2004 | |
| WO | WO-9509659 | A1 | 4/1995 | |
| WO | WO-9947129 | A1 | 9/1999 | |
| WO | WO 02/40242 | | 5/2002 | |
| WO | WO-03000234 | A1 * | 1/2003 | ........... A61K 9/5153 |
| WO | WO-2005006101 | A2 | 1/2005 | |
| WO | WO-2005035735 | A2 | 4/2005 | |
| WO | WO 2008093095 | | 8/2008 | |
| WO | WO 2011/101684 | A1 | 8/2011 | |
| WO | WO-0024378 | A1 | 8/2011 | |
| WO | WO 2011101684 | | 8/2011 | |
| WO | WO-2011101684 | A1 | 8/2011 | |
| WO | 2012/155110 | A1 | 11/2012 | |
| WO | WO 2012155110 | | 11/2012 | |
| WO | WO-2013071126 | A1 * | 5/2013 | ............ A61L 27/54 |
| WO | WO-2016011387 | A1 | 1/2016 | |
| WO | WO-2016096054 | A1 | 6/2016 | |

OTHER PUBLICATIONS

Ehrbar et al. (Enzymatic formation of modular cell-instructive fibrin analogs for tissue engineering, Biomaterials, vol. 28:3856-3866 Apr. 5, 2007) (Year: 2007).*

Ehrbar et al. (Elucidating the Role of Matrix Stiffness in 3D Cell Migration and Remodeling, Biophys J., vol. 100(2):284-293 (Jan. 19, 2011) (Year: 2011).*

IUPAC Gold Book, "Micropore", 1 page, also available at http://goldbook.iupac.org/html/M/M03906.html (last visited Oct. 8, 2018) (Year: 2018).*

Rouquerol et al., Recommendations for the Characterization of Porous Solids, IUPAC Technical Report, Pure & Appl. Chem., vol. 66(8):1739-1758 (1994) (Year: 1994).*

IUPAC Gold Book, "coalescence", 2 pages, also available at http://goldbook.iupac.org/html/C/C01119.html (last visited Oct. 8, 2018) (Year: 2018).*

IUPAC Gold Book, "sintering", 2 pages, also available at http://goldbook.iupac.org/html/S/S05704.html (last visited Oct. 8, 2018) (Year: 2018).*

Boula et al., Journal of Physical Chemistry C, vol. 120:386-395 (Dec. 18, 2015) (Year: 2015).*

Murata, Polymerization, Chapter 17: Rheology-Theory and Application to Biomaterials, pp. 403-426 (2012) (Year: 2012).*

Dynamic Mechnical Analysis (DMA): A beginner's Guide, www.Perkinelmer.com, 23 pages (Apr. 29, 2008), also available at https://www.perkinelmer.com/CMSResources/Images/44-74546GDE_IntroductionToDMA.pdf (last visited Oct. 23, 2018) (Year: 2008).*

Yan et al., Rheological properties of peptide-based hydrogels for biomedical and other applications, Chem. Soc. Rev., vol. 39:3528-3540 (2010) (Year: 2010).*

Jorfi et al., Physiologically responsive, mechanically adaptive polymer optical fibers for optogenetics, Optics Letters, vol. 39(10): 2872-2875 (2014) (Year: 2014).*

Renkema et al., The effect of pH on heat denaturation and gel forming properties of soy proteins, Journal of Biotechnology, vol. 79:223-230 (2000) (Year: 2000).*

Kim et al., Three-Dimensional Porous Biodegradable Polymeric Scaffolds Fabricated with Biodegradable Hydrogel Porogens, Tissue Engineering: Part C, vol. 15(4):583-594 (2009) (Year: 2009).*

Elias Mallis, De Novo Program, FDA, 64 slides (Nov. 4, 2014), also available at https://www.fda.gov/downloads/training/cdrhlearn/ucm421766.pdf (last visited Oct. 4, 2018) (Year: 2014).*

Scott et al., Modular scaffolds assembled around living cells using poly(ethylene glycol) microspheres with macroporation via a non-cytotoxic porogen, Acta Biomaterialia, vol. 6:29-38 (2010) (Year: 2010).*

Jia et al., Hyaluronic Acid-Based Microgels and Microgel Networks for Vocal Fold Regeneration, Biomacromolecules, vol. 7:3336-3344 (2006) (Year: 2006).*

Hoare et al., Hydrogels in drug delivery: Progress and challenges, Polymer, vol. 49:1993-2007 (2008) (Year: 2008).*

Annabi et al., Controlling the Porosity and Microarchitecture of Hydrogels for Tissue Engineering, Tissue Engineering, vol. 16(4):371-383 (2010) (Year: 2010).*

Sacanna et al. (Lock and key colloids, Nature, vol. 464:575-578 (Mar. 2010) (Year: 2010).*

Lee et. al., The effects of cross-linking of collagen-glycosaminoglycan scaffolds on compressive stiffness, chondrocyte-mediated contraction, proliferation and biosynthesis, Biomaterials, vol. 22:3145-3154 (2001) (Year: 2001).*

Trentin et al., PNAS, vol. 103(8):2506-2511 (Feb. 21, 2006) (Year: 2006).*

Dreifke et al., (Investigation of potential injectable polymeric biomaterials for bone regeneration, Journal of Biomedical Materials Research, vol. 101A(8):2436-2447 (Aug. 2013) (Year: 2013).*

Thaiboonrod et al., Doubly crosslinked poly(vinyl amine) microgels: hydrogels of covalently inter-linked cationic microgel particles, J. Mater. Chem. B, 2014, 2, 110 (published online Nov. 19, 2013)) (Year: 2013).*

IUPAC Gold Book, "Microgel", 2 pages (Feb. 24, 2014), also available at https://goldbook.iupac.org/html/M/M03901.html (last visited Jun. 20, 2019) (Year: 2014).*

Nichols et al., Biomaterials, vol. 30:5283-5291 (2009) (Year: 2009).*

PCT International Preliminary Report on Patentability (Chapter I of the Patent Cooperation Treaty) for PCT/US2015/040962, Applicant: The Regents of the University of California, Form PCT/IB/326 and 373, dated Jan. 26, 2017 (18pages).

Du et al., Directed assembly of cell-laden microgels for fabrication of 3D tissue constructs, PNAS, vol. 105 (28):9522-9527 (Jul. 15, 2008).

Ergenc et al., Recent Advances in the Modeling of PEG Hydrogel Membranes for Biomedical Applications, Biomedical Applications, Biomedical Engineering, Trends in Materials Science, Mr Anthony Laskovski (Ed.), ISBN: 978-953-307-513-6, Chapter 14, pp. 307-346 (2011).

Guan et al., PNIPAM microgels for biomedical applications: from dispersed particles to 3D assemblies, Soft Matter, vol. 7:6375-6384 (2011).

Jia et al., Hyaluronic Acid-Based Microgels and Microgel Networks for Vocal Fold Regeneration, Biomacromolecues, 2006, 7 (12), pp. 3336-3344.

Park et al., Bovine Primary Chondrocyte Culture in Synthetic Matrix Metallopreteinase-Sensitive Poly(ethylene glycol)-Based Hydrogels as a Scaffold for Cartilage Repair, Tissue Engineering, vol. 10(3/4/):515-522 (2004).

Sala et al., Microstructured Polymer Films and Matrices for Tissue Engineering, Poster Session, University of Zurich, Institute for Biomedical Engineering, 1 page with 2 pages of citation info, 2007, also available at http://www.lbb.ethz.ch/Publications/Posters/CCMXposter.pdf (last visited Dec. 21, 2016).

Thorne et al., Microgel applications and commercial considerations, Colloid. Polym. Sci., vol. 289:625-646 (2011).

Turturro et al., MMP-Sensitive PEG Diacrylate Hydrogels with Spatial Variations in Matrix Properties Stimulate Directional Vascular Sprout Formation, PLoS One 8(3): e58897. doi:10.1371/journal.pone.0058897, pp. 1-14 (Mar. 12, 2013).

Anna, et al., Formation of dispersions using 'flow focusing' in microchannels. *Appl. Phys. Lett.*82:364-366 (2003).

Bramfeld, et al., Scaffold Vascularization: A Challenge for Three-Dimensional Tissue Engineering. *Curr. Med. Chem.*17:3944-3967 (2010).

Burdick, et al., Controlled Degradation and Mechanical Behavior of Photopolymerized Hyaluronic Acid Networks. Biomacromolecules 6:386-391 (2005).

Chen, et al., Young's modulus measurements of soft tissues with application to elasticity imaging. *IEEE Trans. Ultrason. Ferroelectr. Freq. Control*43:191-194 (1996).

(56) References Cited

OTHER PUBLICATIONS

Chen, H. et al. Hydrogel-thickened microemulsion for topical administration of drug molecule at an extremely low concentration. *Int. J. Pharm.*341, 78-84 (2007).
Cheng, S. and Bilston, L. E. Unconfined compression of white matter. *J. Biomech.*40:117-124 (2007).
Discher, et al. Growth Factors, Matrices, and Forces Combine and Control Stem Cells.*Science*324:1673-1677 (2009).
Du, et al., Directed assembly of cell-laden microgels for fabrication of 3D tissue constructs. *Proc. Natl. Acad. Sci.*105: 9522-9527 (2008).
Dunne, et al., Influence of particle size and dissolution conditions on the degradation properties of polylactide-co-glycolide particles. *Biomaterials*21:1659-1668 (2000).
Fukano, Y. et al. Characterization of an in vitro model for evaluating the interface between skin and percutaneous biomaterials. *Wound Repair Regen.*14: 484-491 (2006).
Fukano, Y. et al. Epidermal and dermal integration into sphere-templated porous poly(2-hydroxyethyl methacrylate) implants in mice.*J. Biomed. Mater. Res. A*94A:1172-1186 (2010).
Galiano, et al., Quantitative and reproducible murine model of excisional wound healing. *Wound Repair Regen. Off. Publ. Wound Heal. Soc. Eur. Tissue Repair Soc.*12: 485-492 (2004).
Galler, et al., Self-Assembling Multidomain Peptide Hydrogels: Designed Susceptibility to Enzymatic Cleavage Allows Enhanced Cell Migration and Spreading. *J. Am. Chem. Soc.* 132: 3217-3223 (2010).
Garstecki, et al., Formation of droplets and bubbles in a microfluidic T-junction—scaling and mechanism of break-up. *Lab. Chip* 6:437-446 (2006).
Gorgieva, S. and Kokol, V. Preparation, characterization, and in vitro enzymatic degradation of chitosan-gelatine hydrogel scaffolds as potential biomaterials. J. Biomed. Mater. Res. A 100:1655-1667 (2012).
Hollister, S. J. Porous scaffold design for tissue engineering. *Nat. Mater.*4:518-524 (2005).
Hosokawa, et al., Handling of Picoliter Liquid Samples in a Poly(dimethylsiloxane)-Based Microfluidic Device. *Anal. Chem.* 71: 4781-4785 (1999).
Huebsch, N. et al. Harnessing traction-mediated manipulation of the cell/matrix interface to control stem-cell fate. *Nat. Mater.*9: 518-526 (2010).
Jgamadze, et al. Colloids as mobile substrates for the implantation and integration of differentiated neurons into the mammalian brain. *PloS One*7, e30293 (2012).
Kawakatsu, et al., Regular-sized cell creation in microchannel emulsification by visual microprocessing method. *J. Am. Oil Chem. Soc.*74:317-321 (1997).
Kong, et al., Controlling rigidity and degradation of alginate hydrogels via molecular weight distribution. Biomacromolecules 5:1720-1727 (2004).
Li, et al., DNA-templated assembly of droplet-derived PEG microtissues. *Lab. Chip*11:2967-2975 (2011).
Lin, et al., Eph/ephrin signaling in epidermal differentiation and disease. *Semin. Cell Dev. Biol.*23:92-101 (2012).
Lucas, T. et al. Differential Roles of Macrophages in Diverse Phases of Skin Repair.*J. Immunol.* 184:3964-3977 (2010).
Lutolf, M. P. and Hubbell, J. A. Synthetic biomaterials as instructive extracellular microenvironments for morphogenesis in tissue engineering. *Nat. Biotechnol.*23:47-55 (2005).
Lutolf, M. P. et al. Synthetic matrix metalloproteinase-sensitive hydrogels for the conduction of tissue regeneration: Engineering cell-invasion characteristics. *Proc. Natl. Acad. Sci.*100: 5413-5418 (2003).
Madden, L. R. et al. Proangiogenic scaffolds as functional templates for cardiac tissue engineering. *Proc. Natl. Acad. Sci.*107:15211-15216 (2010).
Parker, et al., Tissue response to mechanical vibrations for 'sonoelasticity imaging'. *Ultrasound Med. Biol.*16:241-246 (1990).

Pautot, et al., Colloid-guided assembly of oriented 3D neuronal networks. *Nat. Methods*5: 735-740 (2008).
Peters, et al., Engineering vascular networks in porous polymer matrices. *J. Biomed. Mater. Res.*60:668-678 (2002).
Richardson, et al., Polymeric system for dual growth factor delivery. *Nat. Biotechnol.*19:1029-1034 (2001).
Rustad, K. C. et al. Enhancement of mesenchymal stem cell angiogenic capacity and stemness by a biomimetic hydrogel scaffold. *Biomaterials* 33:80-90 (2012).
Samani, et al., Measuring the elastic modulus of ex vivo small tissue samples. *Phys. Med. Biol.*48: 2183 (2003).
Schense, et al., Cross-linking exogenous bifunctional peptides into fibrin gels with factor XIIIa. *Bioconjug. Chem.*10:75-81 (1999).
Seliktar, et al., MMP-2 sensitive, VEGF-bearing bioactive hydrogels for promotion of vascular healing. *J. Biomed. Mater. Res. A*,68:704-716 (2004).
Stachowiak, et al., Bioactive Hydrogels with an Ordered Cellular Structure Combine Interconnected Macroporosity and Robust Mechanical Properties. Adv. Mater. 17:399-403 (2005).
Stratman, et al., Pericyte recruitment during vasculogenic tube assembly stimulates endothelial basement membrane matrix formation. *Blood* 114:5091-5101 (2009).
Wade, R. J. and Burdick, J. A. Engineering ECM signals into biomaterials. Mater. Today 15:454-459 (2012).
Wang, et al. Multifunctional chondroitin sulphate for cartilage tissue-biomaterial integration. *Nat. Mater.*6:385-392 (2007).
Yang, et al., The Design of Scaffolds for Use in Tissue Engineering. Part I. Traditional Factors. Tissue Eng.7:679-689 (2001).
Yeh, et al., Elastic modulus measurements of human liver and correlation with pathology. Ultrasound Med. Biol.28:467-474 (2002).
The extended European search report dated Feb. 19, 2018 in European Patent Application No. 15821310.8-1109, (11 pages).
Communication pursuant to Rules 70(2) and 70a(2) EPC dated Mar. 8, 2018 European Patent Application No. 15821310.8-1109, (1 page).
Lam, Jonathan et al., Design of cell-matrix interactions in hyaluronic acid hydrogel scaffolds, Acta Biomaterialia, vol. 10, No. 4, Apr. 1, 2014, pp. 1571-1580, XP55449152.
Lin, Chien-Chi et al., Peg Hydrogels for the Controlled Release of Biomolecules in Regenerative Medicine, Pharmaceutical Research, Kluwer Academic Publishers-Plenum Publishers, NL, vol. 26, No. 3, Dec. 18, 2008, pp. 631-643, XP019686137.
Yongdoo, Part et al., Bovine primary chondrocyte culture in synthetic matrix metalloproteinase-sensitive poly (ethylene glycol)-based hydrogels as a scaffold for cartilage repair, Tissue Engineering, Larchmont, NY, US, vol. 10, No. 3-4, Mar. 1, 2004, pp. 515-522, XP002464246.
Alijotas-Reig et al. Late-Onset Inflammatory Adverse Reactions Related to Soft Tissue Filler Injections. Clin. Rev. Allergy Immunol. 45:97-108 (Aug. 2013).
Conchouso et al. Three-dimensional parallelization of microfluidic droplet generators for a litre per hour volume production of single emulsions. Lab. Chip14: 3011-3020 (Aug. 2014).
Das et al. Biomaterials and Nanotherapeutics for Enhancing Skin Wound Healing. Front Bioeng Biotechnol 4:82 (Oct. 2016).
De France et al. Structured Macroporous Hydrogels: Progress, Challenges, and Opportunities. Adv Healthc Mater 7(1):17 pgs (Jan. 2018).
Griffin et al. Accelerated wound healing by injectable microporous gel scaffolds assembled from annealed building blocks. Nat Mater 14:737-744 (Jun. 2015).
Griffin et al. Hybrid photopatterned enzymatic reaction (HyPER) for in situ cell manipulation. Chembiochem Eur. J. Chem. Bio1.15:233-242 (Jan. 2014).
Guvendiren et al. Engineering synthetic hydrogel microenvironments to instruct stem cells. CWT Opin Biotechnol 24:841-846 (Oct. 2013).
Hunckler et al. A current affair: electrotherapy in wound healing. J Multidiscip Healthc 10:179-194 (Apr. 2017).
Jgamadze et al. Thermoswitching Microgel Carriers Improve Neuronal Cell Growth and Cell Release for Cell Transplantation. Tissue Eng. Part C Methods (Jan. 2014).
Jiang et al. Cell-laden microfluidic microgels for tissue regeneration. Lab Chip 16(23):4482-4506 (Nov. 2016).

(56) References Cited

OTHER PUBLICATIONS

Lee et al. Tissue, cell and engineering. Curr. Opin. Biotechnol. 24:827-829 (Oct. 2013).
Ling et al. A cell-laden microfluidic hydrogel. Lab Chip 7(6):756-762 (Jun. 2007).
Qi et al. DNA-directed self-assembly of shape-controlled hydrogels. Nat. Commun. 4:2275 (2013).
Sokic et al. In situ generation of cell-laden porous MMP-sensitive PEGDA hydrogels by gelatin leaching. Macromol. Biosci.14:731-739 (May 2014).
Stejskalova et al. Using biomaterials to rewire the process of wound repair. Biomater Sci 5(8):1421-1434 (Jul. 2017).
Wang et al. Novel Biodegradable Porous Scaffold Applied to Skin Regeneration. PLoS One8:e56330 (Jun. 2013).
Xin et al. Assembly of PEG Microgels into Porous Cell-Instructive 3D Scaffolds via Thiol-Ene Click Chemistry. Adv Healthc Mater 7(11):e1800160 (Jun. 2018).
Gan, Tiantian et al., In Situ Gelation of P(NIPAM-HEMA) Microgel Dispersion and Its Applications as Injectable 3D Cell Scaffold, Biomacromolecules 2009, 10, 1410-1415.
Guan, Ying et al., PNIPAM microgels for biomedical applications: from dispersed particles to 3D assemblies, Soft Matter, 2011, 7, 6375-6384.
Hu, Zhibing et al., Hydrogel Nanoparticle Dispersions with Inverse Thermoreversible Gelation, Adv. Mater. 2004, 16, No. 4, Feb. 17, 305-309, DOI: 10.1002/adma.200305560.
Karg, Matthias et al., New "smart" poly(NIPAM) microgels and nanoparticle microgel hybrids: Properties and advances in characterisation, Current Opinion in Colloid & Interface Science 14 (2009) 438-450.
Saunders, Brian R. et al., Microgel particles as model colloids: theory, properties and applications, Advances in Colloid and Interface Science, 80 (1999) 1-25.
Yin, Yadong et al., Self-Assembly of Monodispersed Spherical Colloids into Complex Aggregates with Well-Defined Sizes, Shapes, and Structures, Adv. Mater. 2001, 13, No. 4, Feb. 19, 267-271.
Zhou, Jun et al., Viscoelastic Behavior and In Vivo Release Study of Microgel Dispersions with Inverse Thermoreversible Gelation, Biomacromolecules 2008, 9, 142-148.
PCT International Search Report for PCT/US2015/040962, Applicant: The Regents of the University of California, Form PCT/ISA/210 and 220, dated Oct. 7, 2017 (6 pages).
PCT Written Opinion of the International Search Authority for PCT/US2015/040962, Applicant: The Regents of the University of California, Form PCT/ISA/237, dated Oct. 7, 2017 (16 pages).
Du, Yanan et al., Directed assembly of cell-laden microgels for fabrication of 3D tissue constructs, 9522-9527, PNAS, Jul. 15, 2008, vol. 105, No. 17.
Office Action dated May 1, 2018 in U.S. Appl. No. 15/829,440, (105 pages).
First Office Action, Japanese Patent Application No. 2017-502712 (corresponding Japanese patent application) dated Jul. 2, 2019 (with English Summary).
Huang et al., Controlled drug release from hydrogel nanoparticle networks, Journal of Controlled Release, 94, 303-11 (2004).
Gaulding et al., Reversible Inter- and Intra-Microgel Cross-Linking Using Disulfides, Macromolecules, 45, 39-45 (2012).
Syrett et al., Functional, star polymeric molecular carriers, built from biodegradable microgel/nanogel cores, Chem. Commun, 47, 1449-1451 (2011).
Aleman et al., IUPAC Recommendations, Pure Appl. Chem., vol. 79(10): 1801-1829 (2007) (Year: 2007).
Chin, UCLA researchers develop new material to accelerate healing, UCLA Newsroom, 3 pages (Jun. 1, 2015), also available at http://newsroom.ucla.edu/releases/ucla-researchers-develop-new-material-to-accelerate-healing (last visited 715120 19) (Year: 2015).
Gan et al., In Situ Gelation of P(NIPAM-HEMA) Microgel Dispersion and Its Applications as Injectable 3D Cell Scaffold, Biomacromolecules vol. 10:1410-1415 (2009) (Year: 2009).

Goyanes et al., Morphometric categorization of the human oocyte and early conceptus, Human Reproduction, vol. 5 (5):613-618 (Jul. 1990) (Year: 1990).
Griffin et al., Accelerated wound healing by injectable microporous gel scaffolds assembled from annealed building blocks, Nature Materials, vol. 14:737-744 and 21 pages of Supplemental Information (Published online Jun. 1, 2015) (Year: 2015).
Lodish et al., Molecular Cell Biology, 4th edition. New York: W. H. Freeman; 2000. Section 21.1, Overview of Neuron Neuron Structure and Function, available at www.ncbi.nlm.nih.gov/books/N BK21535/ (last visited Jun. 20, 2019). (Year: 2000).
Koh et al., Three-Dimensional Scaffolds for Tissue Engineering Applications: Role of Porosity and Pore Size, Tissue Engineenng: Part B, vol. 19(6): 485-502 (online Jun. 25, 2013) (Year: 2013).
Malafaya et al., Biomaterials, vol. 29:3914-3926 (Jul. 22, 2008) (Year: 2008).
Maree et al., Morphometric dimensions of the human sperm head depend on the staining method used, Human Reproduction, vol. 25(6):1369-1382 (epub Apr. 17, 2010) (Year: 2010).
Nguyen et al., Clickable Poly(ethylene glycoi)-Microsphere-Based Cell Scaffolds, Macromol Chem Phys., vol. 214 (8):948-956 (online Mar. 4, 2013) (Year: 2013).
Parlato et al., Adaptable Poly(ethylene glycol) Microspheres Capable of Mixed-mode Degradation, Acta Biomater., vol. 9):9270-9280 (online Aug. 17, 2013) (Year 2013).
Patel, Poly(ethylene glycol) Hydrogel System Supports Preadipocyte Viability, Adhesion, and Proliferation, Tissue Engineenng, vol. 11, No. 9/10, 2005 (8pages).
Sanson el al., Polym. Chem., vol. 1:965-977 (2010) (Year: 2010).
IUPAC Gold Book, "Peptides", 2 pages (Feb. 24, 2014), also available at https://goldbook.iupac.org/html/P/P04479. html (last visited Jul. 1, 2019) (Year: 2014).
Office Action dated Jul. 8, 2019 in U.S. Appl. No. 16/264,466, (91 pages).
Response to an Examiner's Report dated Jun. 21, 2019 in Australian Application No. 2015289474, (21 pages).
Examination report No. 2 for standard patent application dated Jul. 15, 2019 in Australian Application No. 2015289474, (4 pages).
Response to an Examiner's Report dated Oct. 28, 2019 in Australian Application No. 2015289474, (30 pages).
Examination report No. 3 for standard patent application dated Oct. 30, 2019 in Australian Application No. 2015289474, (2 pages).
First Office Action dated Jul. 3, 2019 in Brazilian Patent Application No. BR112017000813-0, (7 pages).
Notification of First Office Action dated Jun. 13, 2019 in Chinese Patent Application No. 2015800494786, (18 pages).
Response to First Office Action dated Sep. 26, 2019 in Chinese Patent Application No. 2015800494786, (8 pages).
Response extended European Search Report dated Sep. 18, 2019 in European Patent Application No. EP15821310.8, (28 pages).
Notice of Rejection dated Mar. 22, 2019 in Japanese Patent Application No. 2017-502712, (17 pages).
Guan, Ying et al., PNIPAM microgels for biomedical applications: from dispersed particles to 3D assemblies, Soft Matter, 2011, vol. 7, pp. 6375-6384.
Huang, Gang et al., Controlled drug release from hydrogel nanoparticle networks, Journal of Controlled release, 2004, vol. 94, pp. 303-311.
Gaulding, Jeffrey C. et al., Reversible Inter- and Intra-Microgel Cross-Linking Using Disulfides, Macromolecules, 2012, vol. 45, pp. 39-45.
Syrett, Jay A. et al., Functional, star polymeric molecular colliers, built from biodegradable microgel/nanogel cores, Chem. Commu., 2011, vol. 47, pp. 1449-1451.
Response to Notice of Rejection dated Jul. 2, 2019 in Japanese Patent Application No. 2017-502712, (12 pages).
Request for Continued Examination dated Feb. 7, 2019 in U.S. Appl. No. 15/829,440, (31 pages).
Cha, Chaenyung et al., Microfluidics-Assisted Fabrication of Gelatin-Silica Core-Shell Microgels for Injectable Tissue Constructs, dx.doi.org/10.1021/bm401533y, Biomacromolecules 2014, 15, 283-290 (Dec. 2013).
Du et al. Fabrication of Hexagonal-Prismatic Granular Hydrogel Sheets. Langmuir 34(11):3459-3466 (Feb. 2018).

(56) References Cited

OTHER PUBLICATIONS

Grainger. Wound healing: Enzymatically crosslinked scaffolds. Nat Mater 14:662-663 (Jul. 2015).

Muehleder et al. Connections matter: channeled hydrogels to improve vascularization. Front Bioeng Biotechnol 2:52 (Nov. 2014).

Nih et al. Injection of Microporous Annealing Particle (MAP) Hydrogels in the Stroke Cavity Reduces Gliosis and Inflammation and Promotes NPC Migration to the Lesion. Adv Mater 29(32):1606471 (Aug. 2017).

Cam et al., Systemic evaluation of natural scaffolds in cutaneous wound healing, J. of Materials Chemistry B, vol. 3:7986-7992 (epub Aug. 21, 2015) (Year: 2015).

Shin, Dissertation Development of Cell-Laden Hydrogels with High Mechanical Strength for Tissue Engineering Applications, MIT, Department of Materials Science and Engineering, 86 pages (Jan. 1, 2014) (Year: 2014).

Smith, Dissertion Engineering Poly(ethylene glycol) Materials to Promote Cardiogenesis, Washington University, St. Louis, Missouri, 142 pages (Aug. 2013) (Year: 2013).

Shih, Thesis, Step-Growth Thiol-ene Photopolymerization to Form Degradable, Cythocompatible and Multi-structural Hydrogels, Purdue University, Indianapolis, Indiana, 92 pages (May 2013) (Year: 2013).

Selimovic et al., Microscale Strategies for Generating cell-encapsulating hydrogels, Polymers, vol. 4:1554-1579 (2012) (Year: 2012).

Hillel et al., Photoactivated Composite Biomaterial for Soft Tissue Restoration in Rodents and in Humans, Sci Transl Med., vol. 3(93):93ra67, 24 pages including Supp., (Jul. 27, 2011) (Year: 2011).

Burdick et al., Hyaluronic Acid Hydrogels for Biomedical Applications, Adv. Mater., vol. 23H41-H56 (2011) (Year: 2011).

Office Action dated Nov. 7, 2018 in U.S. Appl. No. 15/829,440, inventor: Donald R. Griffin, (101 pages).

Examination report No. 1 for standard patent application dated Nov. 30, 2018 in Australian Patent Application No. 2015289474, (6pages).

Examination—Response to an Examiners Report dated Nov. 21, 2019 in Australian Patent Appl No 2015289474, (10pages).

Notice of Acceptance dated Nov. 26, 2019 in Australian Patent Appl No. 2015289474, (3pages).

Response to Office Action dated Nov. 22, 2019 in Brazilian Patent Appl No. 112017000813-0, (17pages).

Office Action dated Nov. 18, 2019 in U.S. Appl. No. 16/596,312, (13pages).

Amendment and Response to Office Action dated Dec. 9, 2019 in U.S. Appl. No. 16/596,312, (9pages).

Restriction Requirement dated Jan. 23, 2020 in U.S. Appl. No. 16/596,312, (10pages).

Notice of Allowance dated Dec. 24, 2019 in Japanese Patent Application No. 2017-502712, (4pages).

Notification of Defects dated Mar. 24, 2020 in Israel Patent Application No. 250092, (7pages).

Notification of Defects dated Aug. 6, 2020 for Israel Patent Application No. 250092, (7pages).

Office Action including partial translation dated Sep. 24, 2020 for Brazilian Patent Appl No. 112017000813-0, (6pages).

Communication pursuant to Article 94(3) EPC dated Oct. 7, 2020 for European Patent Appl No. 15621310.8-1109 (10pages).

KIPO's Notice of Preliminary Rejection dated Oct. 17, 2020 for Korean Patent Appl No. 10-2017-7004012, (16pages).

\* cited by examiner

FIG. 2B
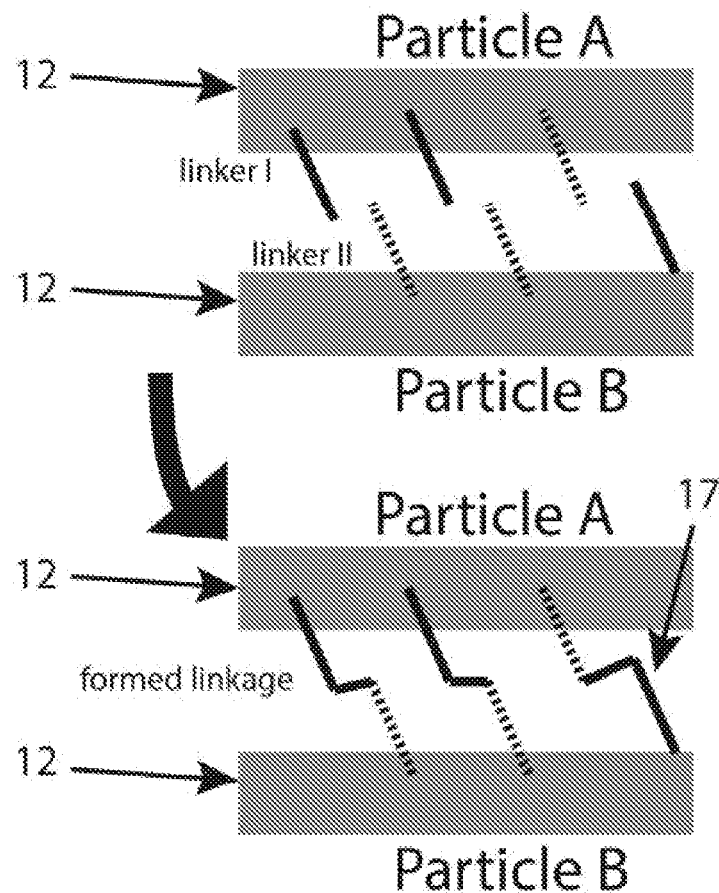
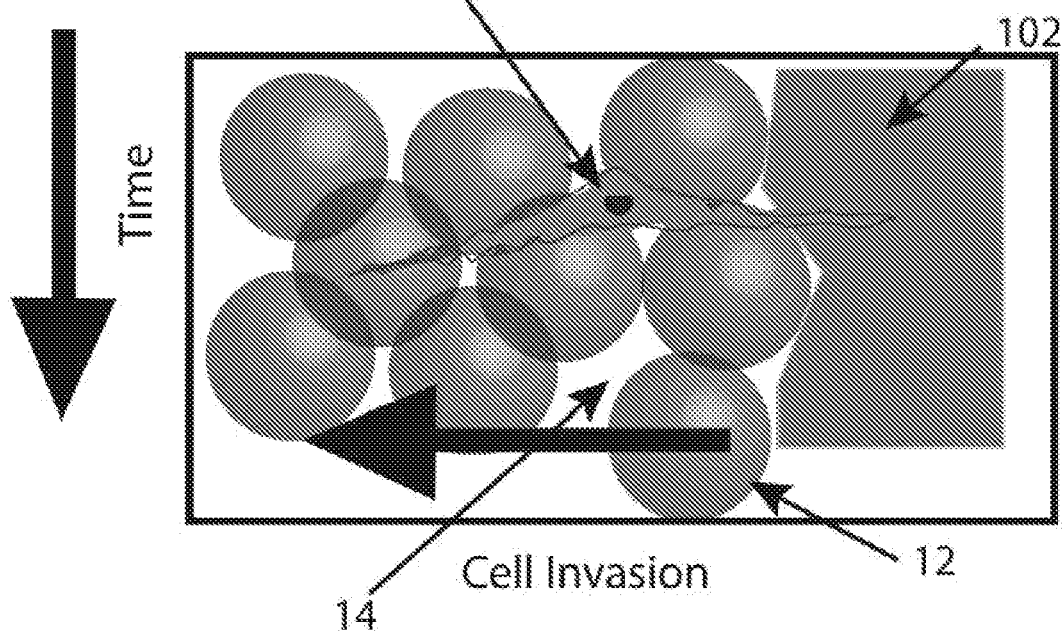
FIG. 2C

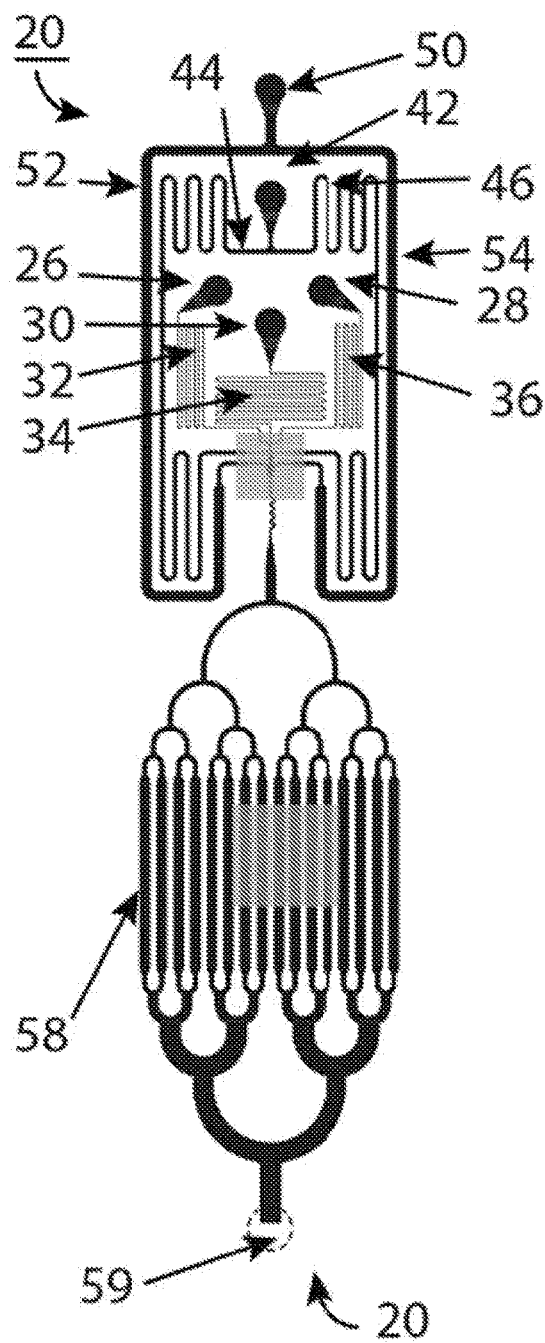
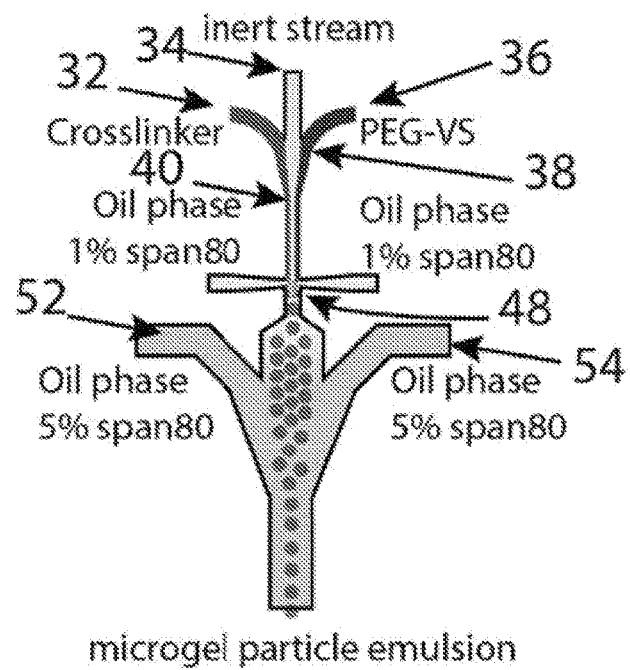
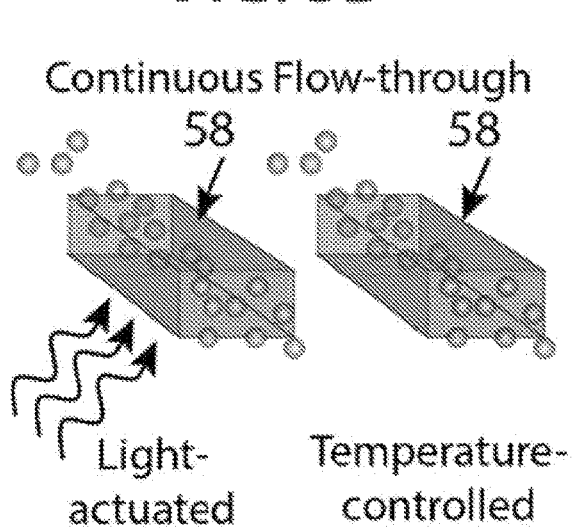
FIG. 3A
FIG. 3B
FIG. 3C

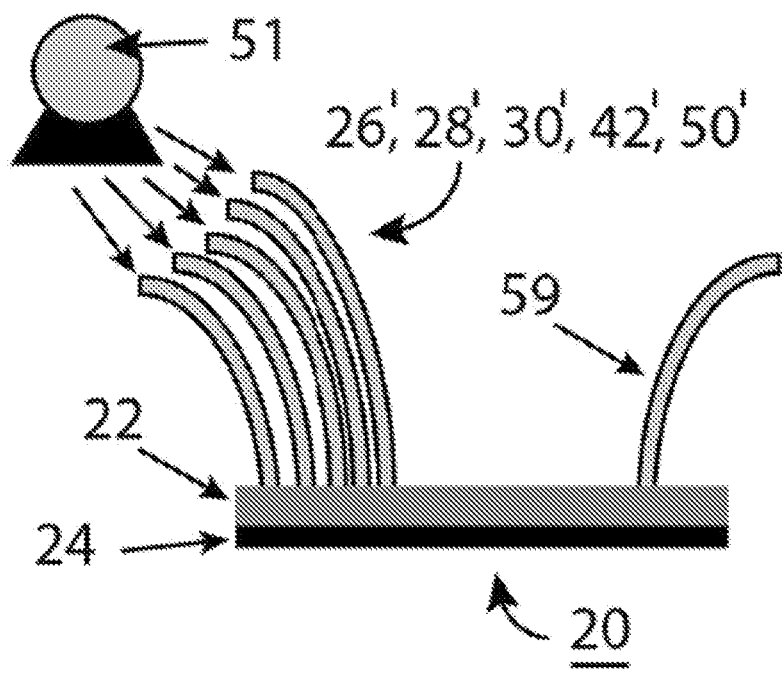
FIG. 3D
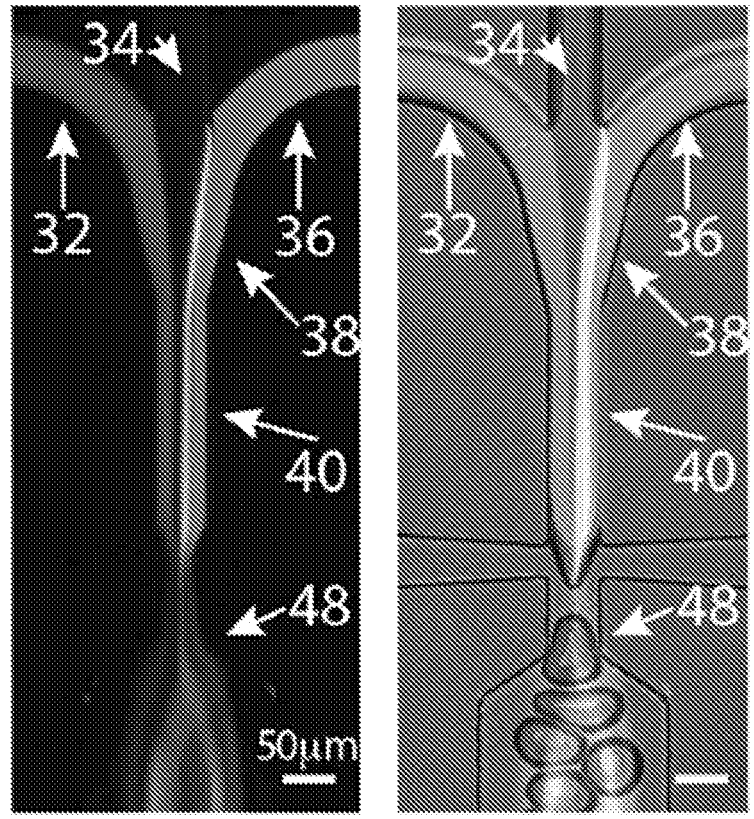
FIG. 3E   FIG. 3F

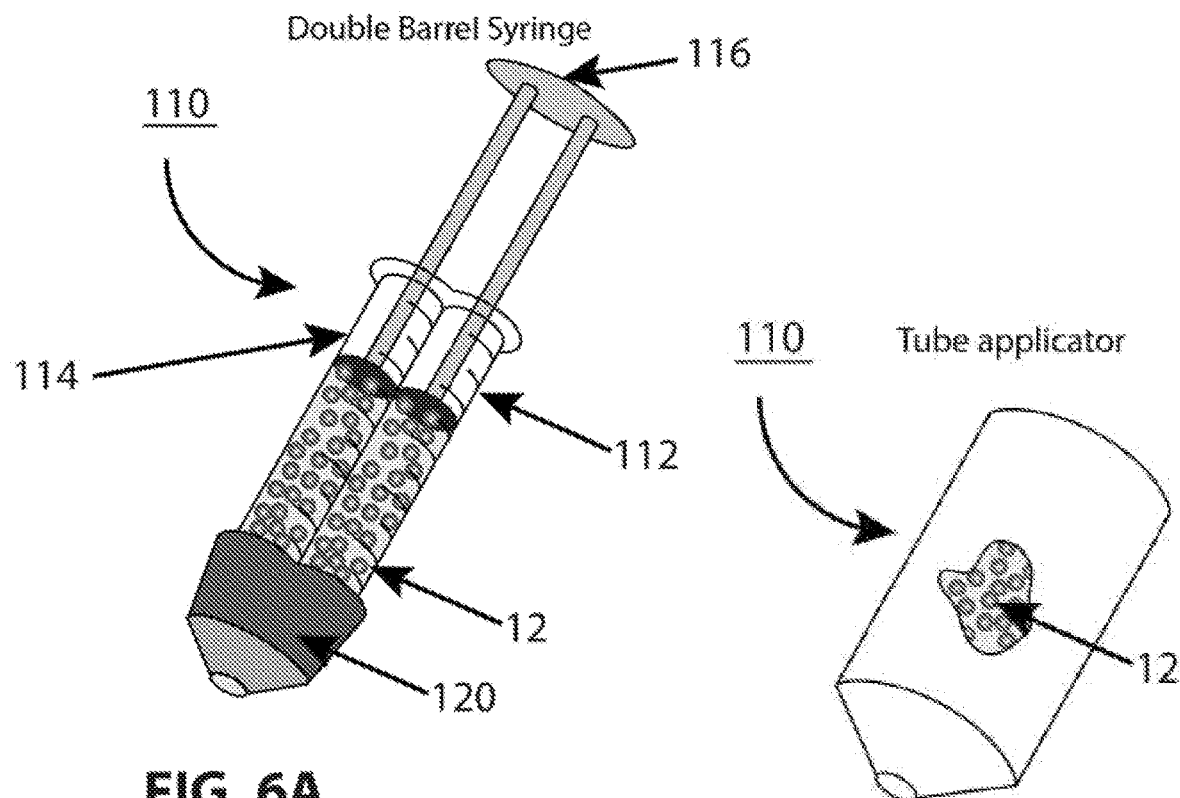
FIG. 6A
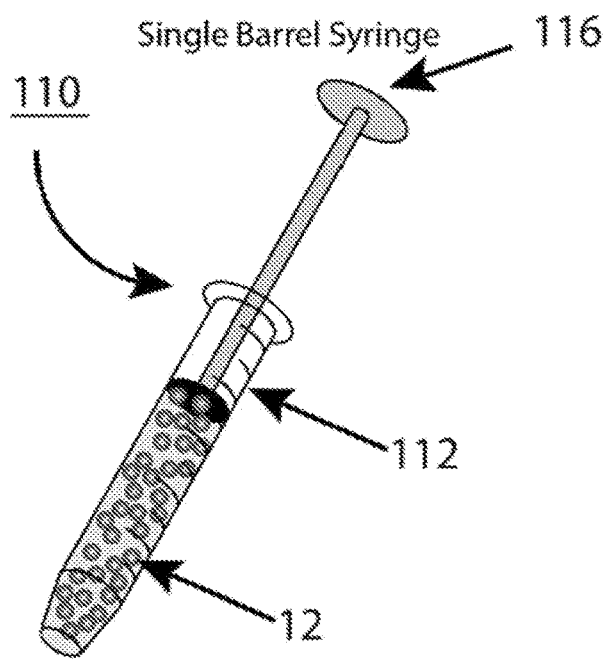
FIG. 6B
FIG. 6C

FIG. 7A  FIG. 7B

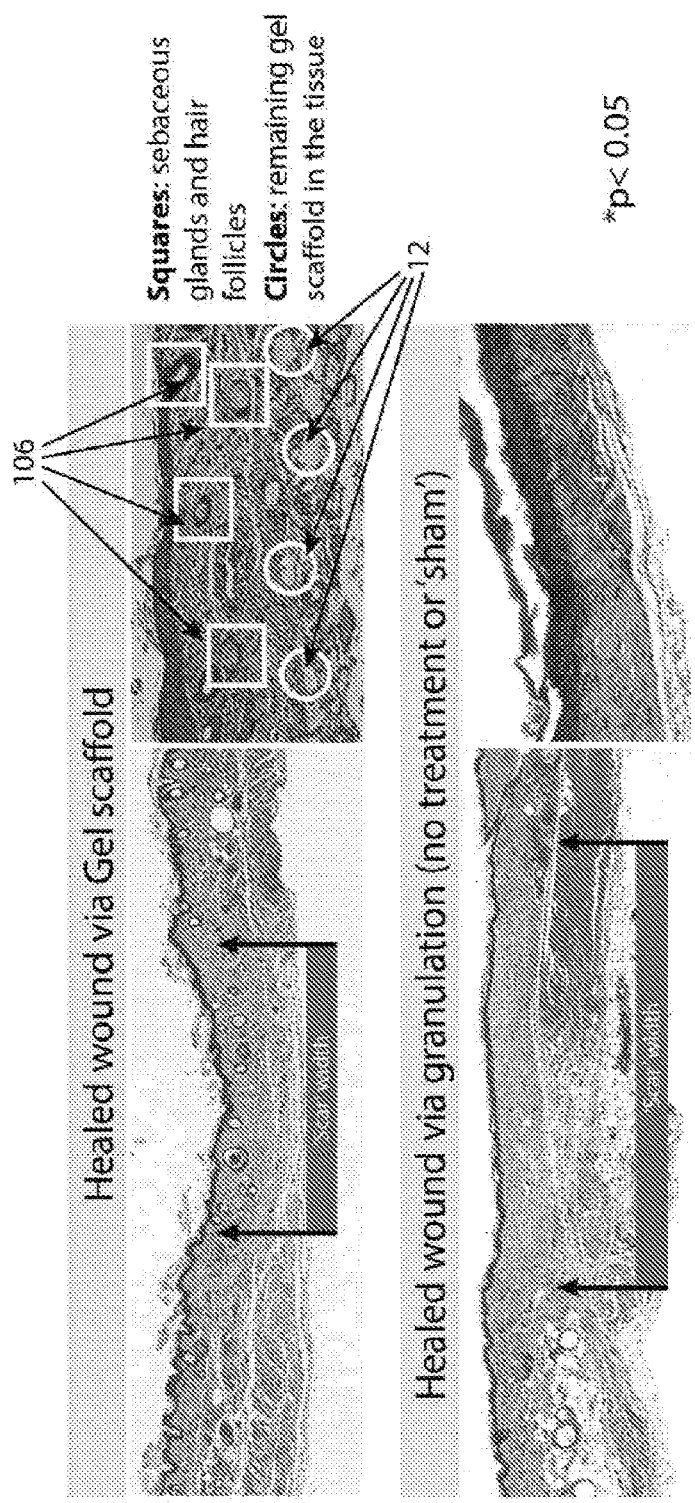
FIG. 8A
FIG. 8B
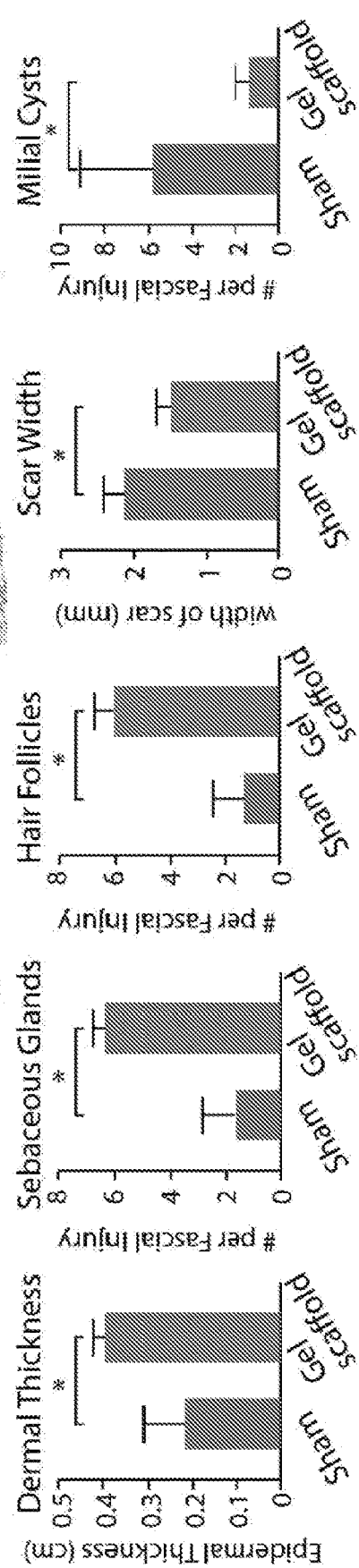
FIG. 8C
FIG. 8D
FIG. 8E
FIG. 8F
FIG. 8G

SEQUENCE LISTING

```
<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: Linker molecule

<400> SEQUENCE: 1

Phe Lys Gly Gly Glu Arg Cys Gly
1               5

<210> SEQ ID NO 2
<211> LENGTH: 14
<212> TYPE: PRT
<213> ORGANISM: Artificial Sequence
<220> FEATURE:
<223> OTHER INFORMATION: Linker molecule

<400> SEQUENCE: 2

Asn Gln Glu Gln Val Ser Pro Leu Gly Gly Glu Arg Cys Gly
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Cell adhesive peptide

<400> SEQUENCE: 3

Arg Gly Asp Ser Pro Gly Glu Arg Cys Gly
1               5                   10

<210> SEQ ID NO 4
<211> LENGTH: 16
```

```
<212> TYPE: PRT
<213> ORGANISM: Artificial Sequence
<220> FEATURE:
<223> OTHER INFORMATION: matrix metalloprotease degradable crosslinker

<400> SEQUENCE: 4

Gly Cys Arg Asp Gly Pro Gln Gly Ile Trp Gly Gln Asp Arg Cys Gly
1               5                   10                  15
```

CONTROLLABLE SELF-ANNEALING MICROGEL PARTICLES FOR BIOMEDICAL APPLICATIONS

RELATED APPLICATIONS

This Application is a divisional of U.S. application Ser. No. 15/179,151, filed on Jun. 10, 2016, which is a continuation of International Patent Application No. PCT/US2015/040962, filed on Jul. 17, 2015, which claims priority to U.S. Provisional Patent Application Nos. 62/025,844 filed on Jul. 17, 2014, 62/059,463 filed on Oct. 3, 2014, and 62/103,002 filed on Jan. 13, 2015. Priority is claimed pursuant to 35 U.S.C. § 119. The above-noted Patent Applications are incorporated by reference as if set forth fully herein.

STATEMENT REGARDING FEDERALLY SPONSORED RESEARCH AND DEVELOPMENT

This invention was made with government support under Grant Numbers HL110592 and NS079691, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 17, 2015 is named 2014-908-4_ST25.txt.

TECHNICAL FIELD

The technical field relates generally to the field of wound treatment, and in particular, the use of microgel particles and scaffolds including the particles for treating and sealing wounds and for tissue filler applications.

BACKGROUND

A central concept tied to the generation and regeneration of tissue is collective cell migration, a process by which entire networks of cells move together into an area of development to facilitate the formation of functional tissue. Researchers have sought to develop would healing agents; however, these materials display batch-to-batch variability and exhibit degradation rates that limit extended structural support for growing tissues. Synthetic materials are more tunable than natural materials and their mechanical properties have been engineered to allow use with a wide range of tissue types. Despite this tunability, however, synthetic injectable biomaterials have been limited to non-porous or nanoporous scaffolds that require physical degradation for cellular migration through the material. Porous synthetic hydrogels that contain pre-formed microscale interconnected pores allow greater cell mobility without the need for degradation, circumventing the trade-off between cell mobility and material stability inherent to non-porous scaffolds. The typical mode of pore formation includes the toxic removal of porogens, or the degradation of encapsulated microparticles, which requires these constructs to be either cast ex vivo, preventing them from seamlessly integrating with the surrounding tissue like an injectable biomaterial or requires long-term in vivo development to resolve the porous structure. For example, Healionics Corporation has developed a technology self-described as Sphere Templated Anigiogenic Regeneration (STAR) in which STAR scaffolds are formed by sintering together an array of packed beads of controlled size, casting a polymer into the interstitial space between the beads, and dissolving away the beads to yield a pore network of interconnected spherical voids. As noted above, however, these conventional processes require the toxic removal of porogens.

SUMMARY

Human skin wounds are an ever-increasing threat to public health and the economy and are very difficult to treat. Physicians, when treating skin wounds, seek to keep the area moist because dry wounds heal much more slowly than wet ones. To accomplish this, physicians often use ointments to fill in the wound, much like filling a pothole with new asphalt. However, these and other conventional approaches to wound healing fail to provide an optimal scaffold to allow new tissue to grow. As a result, new tissue growth, if any, is relatively slow and fragile leading to longer healing times, to the extent timely healing is even possible.

In the context of engineered tissue healing, the instant inventors have identified the gold standard of the development of interconnected microporous scaffolds that allow for interconnected cell networks and collective migration without the need for scaffold degradation or invasive procedures for implantation is essential for bulk integration with the surrounding tissue. In fact, to be most effective, the instant inventors have identified that these materials should facilitate collective cell migration that mediates regeneration while providing molecular cues to promote wound healing and niche recognition. Further, the instant inventors have also identified that these materials must be able to be seamlessly replaced by migrating cells and natural matrix, provide a stable structural support prior to replacement, and be easily delivered and conform to the site of injury to minimize fibrotic and inflammatory responses.

Provided herein are systems, compositions, methods, and devices that implement these principles and provide a biomaterial that promotes rapid regeneration of tissue while maintaining structural support of surrounding tissue of a wound. Indeed, the present inventors have achieved solutions to long-felt and unmet medical needs in the field of tissue engineering using a flowable or injectable microgel-based, tailor-made material chemistry and microfluidic fabrication of uniform spherical building blocks, including for example building blocks the width of a human hair.

The technology described herein utilizes chemistry to generate tiny microgels that can be assembled into a large unit, leaving behind a path for cellular infiltration. The result is a packed cluster of microscopic synthetic polymer bodies (e.g., spheres) attached at their surfaces, akin to a jar of gumballs that are stuck together. The cluster creates a scaffold of microporous annealed particles (e.g., a porous gel scaffold) that fills in the wound. New tissue quickly grows into the voids between the microgel particles, and as the microgel particles degrade into the body, a matrix of newly grown tissue is left where the wound once was. New tissue continues growing until the wound is completely healed.

The microgel systems described herein represents a substantial improvement over conventional products. For example, the technologies described herein do not require added growth factors to attract cells into the material. The geometry of the described microgel networks entice cells to migrate into the microgel.

The present inventors have demonstrated that the described microgels can promote the growth of new cells and formation of networks of connected cells at previously unseen rates. For example, during in vivo studies, significant tissue regeneration was observed in the first 48 hours, with much more healing over five days compared to conventional materials in use today.

The technologies described herein are useful for a wide array of applications. For example, the disclosed microgel technology can be used for wound applications, including acute damage, like lacerations and surgical wound closures, and also more chronic applications like diabetic ulcers and large-area burn wounds. The hydrogel scaffolds described herein can also be useful in trauma situations, such as battlefields or emergency rooms.

Described herein, in certain aspects, are systems, compositions, methods, and devices comprising a microporous gel that comprises an aqueous solution comprising a plurality of microgel particles and a crosslinker, including for example a biodegradable crosslinker. Microporous gels described herein are flowable and/or injectable and can be applied in multiple different ways, including for example topically or by injection. Injected and/or flowable microporous gels can be inserted transdermally or into deep tissue. Flowable microporous gels can also be administered topically to the dermis and other tissues.

In one aspect, when an annealing agent is applied to the plurality of microgel particles, the microgel particles form a covalently-stabilized scaffold of microgel particles having interstitial spaces therein. In certain applications, the systems, compositions, methods, and devices are specifically engineered for biomedical applications. In some embodiments, the microporous gel particles further comprise a crosslinker, wherein the crosslinker includes a matrix metalloprotease (MMP)-degradable crosslinker. In one or more embodiments, an annealing agent comprises Factor XIIIa. In further or additional embodiments, the annealing agent comprises Eosin Y, a free radical transfer agent, or a combination thereof.

In some embodiments, the microgel systems, compositions, methods, and devices further comprises a source of light configured to illuminate a mixture of the plurality of microgel particles and the annealing agent. In one or more embodiments, the microporous gel particles comprise cell adhesive peptides exposed on a surface thereof. In some embodiments, the microporous gel particles comprise a K-peptide. In further or additional embodiments, the microporous gel particles comprise a K-peptide that comprises a Factor XIIIa-recognized lysine group. In some embodiments, the microporous gel particles comprise a Q-peptide. In some embodiments, the Q-peptide comprises a Factor XIIIa-recognized glutamine group. In certain embodiments, the microporous gel particles comprise a crosslinker that is degradable. In certain embodiments, the microporous gel particles comprise interstitial spaces that comprise border surfaces exhibiting negative concavity. In one or more embodiments, the covalently-stabilized scaffold of microgel particles has a void volume of from about 10% to about 50%.

In one embodiment, a microporous gel system for biomedical applications includes an aqueous solution containing a plurality of microgel particles formed with a biodegradable crosslinker such as a matrix metalloprotease (MMP)-degradable crosslinker and an annealing agent that when applied to the plurality of microgel particles causes the microgel particles to form a covalently-stabilized scaffold of microgel particles having interstitial spaces therein.

In another embodiment, a microporous gel system includes a delivery device and a collection of biodegradable microgel particles contained in an aqueous solution and stored in the delivery device. An annealing agent or annealing agent precursor is also stored in the delivery device. The delivery device may contain a single or multiple compartments, depending on the particular embodiment employed.

In another embodiment, a method of treating tissue includes delivering to the tissue an aqueous-based solution containing a plurality of microgel particles decorated with cell adhesive peptides, wherein the microgel particles are formed with a biodegradable crosslinker such as matrix metalloprotease (MMP)-degradable crosslinker. The plurality of microgel particles are exposed to an annealing agent that anneals the microgel particles to form a covalently-stabilized scaffold of microgel particles having interstitial spaces therein.

In another embodiment, a microporous gel system for biomedical applications includes a collection of microgel particles formed by a reaction of a backbone polymer having one or more cell attachment moieties, one or more annealing components, and a biodegradable network crosslinker component. The microporous gel system includes an endogenous or exogenous annealing agent that links the microgel particles together in situ via the annealing components to form a covalently-stabilized scaffold of microgel particles having interstitial spaces therein.

In another aspect, described herein are systems, compositions, methods, and devices that comprise a delivery device or mechanism and microporous gel. In certain embodiments, the delivery device contains an aqueous solution comprising a plurality of microgel particles and the annealing agent or an annealing agent precursor. In one or more embodiments, the delivery device comprises a single compartment delivery device containing the aqueous solution comprising a plurality of microgel particles and the annealing agent. In one or more embodiments, the delivery device comprises a multiple (e.g., double) compartment delivery device, wherein one compartment contains the aqueous solution containing plurality of microgel particles and a first annealing agent precursor and the second compartment contains the aqueous solution containing plurality of microgel particles and a second annealing agent precursor. In certain embodiments, microporous gels further comprise a (MMP)-degradable crosslinker that comprises at least one D-amino acid. In further or additional embodiments, the microgel particles comprise a (MMP)-degradable crosslinker comprises a plurality of D-amino acids.

In yet another aspect, described here is a microporous gel system comprising: a delivery device; a plurality biodegradable microgel particles contained in an aqueous solution and stored in the delivery device; and an annealing agent or annealing agent precursor stored in the delivery device. In one or more embodiments, the microporous gel particles further comprise a collection of biodegradable microgel particles of two or more types that are contained in an aqueous solution and stored in the delivery device. In certain embodiments, the delivery device comprises two compartments, biodegradable microgel particles are stored in each of the two compartments, and a first annealing precursor is stored in one compartment and a second annealing precursor is stored in the other compartment, wherein the annealing agent is formed by the presence of both the first and second annealing precursors. In one or more embodiments, the delivery device comprises a single compartment and the collection of biodegradable microgel particles and the annealing agent are both stored in the single compartment.

In still further or additional embodiments, the annealing agent comprises a photoinitiator and a free radical transfer agent stored in the single compartment. In a further or additional embodiment, the microporous gel system further comprises a light-emitting device configured to illuminate a mixture of the collection of biodegradable microgel particles and the annealing agent. In certain embodiments, the microgel particles comprise substantially monodisperse spheres. In one or more embodiments, the substantially monodisperse spheres have a diameter within the range of from about 30 micrometers to about 150 micrometers. In further or additional embodiments, the microgel particles are covalently linked to another after annealing.

Provided in another aspect is a method of treating tissue comprising: delivering to the tissue an aqueous-based solution containing a plurality of microgel particles; and exposing the plurality of microgel particles to an annealing agent that anneals the microgel particles to form a covalently-stabilized scaffold of microgel particles having interstitial spaces therein. In some embodiments, the plurality of microgel particles is decorated with cell adhesive peptides, and wherein the microgel particles are formed with a matrix metalloprotease (MMP)-degradable crosslinker. In one or more embodiments, the annealing agent is delivered to the tissue. In some embodiments, the annealing agent is present within the tissue. In yet additional embodiments, the method further comprises initiating the annealing of the microgel particles with exposure to light. In some embodiments, the wavelength of light is in the visible range. In some embodiments, the wavelength of light is in the infrared range. In one or more embodiments, the aqueous-based solution and the annealing agent are delivered simultaneously. In some embodiments, the aqueous-based solution and the annealing agent are delivered sequentially. In still further or additional embodiments, the microgel particles comprise a therapeutically active chemical compound. In certain embodiments, the microgel particles expose or elute the chemical compound to the tissue. In one or more embodiments, the tissue comprises a site of cosmetic reconstruction, chronic wound development, acute tissue damage, or a tissue gap caused by surgical incision. In yet additional embodiments, the (MMP)-degradable crosslinker comprises D-amino acid.

In another aspect, provided is a microporous gel system or device comprising: a collection of microgel particles comprising a backbone polymer having one or more cell attachment moieties, one or more annealing components, and one or more biodegradable network crosslinker components; and an endogenous or exogenous annealing agent that links the microgel particles together in situ via the annealing components to form a covalently-stabilized scaffold of microgel particles having interstitial spaces therein. In certain embodiments, the backbone polymer comprises poly(ethylene glycol) vinyl sulfone. In one or more embodiments, the one or more cell attachment moieties comprise a RGD peptide or a fragment thereof, fibronectin or a fragment thereof, collagen or a fragment thereof, or laminin or a fragment thereof. In some embodiments, the one or more cell attachment moieties comprise a RGD peptide or a fragment thereof. In an embodiment, the one or more cell attachment moieties comprise SEQ ID NO: 3 or a fragment thereof. In further or additional embodiments, the one or more annealing components comprise a K-peptide and a Q-peptide. In certain embodiments, the K-peptide comprises a Factor XIIIa-recognized lysine group and the Q-peptide comprises a Factor XIIIa-recognized glutamine group. In some embodiments, the biodegradable network crosslinker component comprises a matrix metalloprotease (MMP)-degradable crosslinker. In one or more embodiments, the (MMP)-degradable crosslinker comprises D-amino acid. In certain embodiments, the collection of microgel particles comprises microgel particles of two or more types. In one or more embodiments, the microgel particles of a first type comprise (MMP)-degradable crosslinker comprising D-amino acid, and microgel particles of a second type comprise (MMP)-degradable crosslinker comprising only L-amino acid. In one or more embodiments, the system or device comprises a single compartment delivery device containing the collection of microgel particles and the annealing agent. In one or more embodiments, the system or device further comprises a double compartment delivery device, wherein one compartment contains the aqueous solution containing plurality of microgel particles and a first annealing agent precursor and the second compartment contains the aqueous solution containing plurality of microgel particles and a second annealing agent precursor, wherein the annealing agent is formed by the presence of the first and second annealing agent precursors.

In an additional aspect, described is a method of treating tissue comprising: delivering to the tissue a first layer of microgel particles decorated with cell adhesive peptides, wherein the microgel particles are formed with a biodegradable crosslinker; exposing the first layer to an annealing agent that anneals the microgel particles to form a covalently-stabilized scaffold of microgel particles having interstitial spaces therein; delivering to the tissue a second layer of microgel particles decorated with cell adhesive peptides, wherein the microgel particles are formed with a biodegradable crosslinker and wherein the microgel particles in the second layer differ in one of a physical property or chemical composition as compared to the microgel particles in the first layer; and exposing the second layer to an annealing agent that anneals the microgel particles to form a covalently-stabilized scaffold of microgel particles having interstitial spaces therein. In one or more embodiments, the microgel particles in the second layer have a different size. In yet additional embodiments, the microgel particles in the second layer have a different shape. In one or more embodiment, the microgel particles in the second layer have a different stiffness. In certain embodiments, the microgel particles in the second layer having a chemical component different from a chemical component in the first layer. In further or additional embodiment, the microgel particles in the second layer having a chemical component of a different concentration from the same chemical component in the first layer.

In another aspect, provided is method of treating tissue comprising: delivering to the tissue an aqueous-based solution containing a plurality of microgel particles decorated with cell adhesive peptides, wherein the microgel particles are formed with a biodegradable crosslinker; exposing the plurality of microgel particles to an annealing agent that anneals the microgel particles to form a covalently-stabilized scaffold of microgel particles having interstitial spaces therein.

In another embodiment, a method of treating tissue includes delivering to the tissue a first layer of microgel particles decorated with cell adhesive peptides, wherein the microgel particles are formed with a biodegradable crosslinker. The first layer is exposed to an annealing agent that anneals the microgel particles to form a covalently-stabilized scaffold of microgel particles having interstitial spaces therein. A second layer of microgel particles decorated with cell adhesive peptides is delivered to the tissue, wherein the microgel particles are formed with a biodegradable crosslinker and wherein the microgel particles in the second layer differ in one of a physical property or chemical composition as compared to the microgel particles in the first layer. The second layer is exposed to an annealing agent that anneals the microgel particles to form a covalently-stabilized scaffold of microgel particles having interstitial spaces therein.

In another embodiment, a method of treating tissue includes delivering to the tissue an aqueous-based solution containing a plurality of microgel particles decorated with cell adhesive peptides, wherein the microgel particles are formed with a biodegradable crosslinker. The plurality of microgel particles are exposed to an annealing agent that anneals the microgel particles to form a covalently-stabilized scaffold of microgel particles having interstitial spaces therein.

In yet an additional aspect, described is a method of making microgel particles comprising: providing a water-in-oil droplet generating microfluidic device having a plurality of input channels leading to a common channel and a pair of oil-pinching channels intersecting with the common channel at a downstream location flowing a first pre-polymer solution containing a polymer backbone modified with oligopeptides into a first input channel; flowing a second solution containing a biodegradable crosslinker into a second input channel; flowing an oil and a surfactant into the pair of oil pinching channels to form droplets containing the first pre-polymer solution and the second solution; and collecting microgel particles formed by cross-linking of the droplets. In another embodiment, the method further comprises a third input channel interposed between the first input channel and the second input channel, wherein a third inert solution containing a pre-polymer is flowed into the third input channel. In one or more embodiments, the method further comprises sheathing the generated droplets with an additional pair of sheathing channels located downstream of a location where the pair of oil pinching channels intersect with the common channel, wherein the additional pair of sheathing channels carries oil and a surfactant at a higher concentration than the surfactant contained in the upstream pair of oil pinching channels. In one embodiment, the method further comprises centrifuging the collected microgel particles. In another aspect, the method comprises reducing the free water volume content of the centrifuged microgel particles. In one or more embodiments, the method comprises storing the collected microgel particles for an extended period of time (e.g., months to years).

In still another embodiment, a method of making microgel particles includes providing a water-in-oil droplet generating microfluidic device having a plurality of input channels leading to a common channel and a pair of oil-pinching channels intersecting with the common channel at a downstream location. A first pre-polymer solution containing a polymer backbone modified with oligopeptides is flowed into a first input channel. A second solution containing a biodegradable crosslinker is flowed into a second input channel. An oil and a surfactant are flowed into the pair of oil pinching channels to form droplets containing the first pre-polymer solution and the second solution. Microgel particles are formed by cross-linking of the droplets which are then collected.

Other objects, features and advantages of the present disclosure will become apparent to those skilled in the art from the following detailed description. It is to be understood, however, that the detailed description and specific examples, while indicating some embodiments of the present disclosure are given by way of illustration and not limitation. Many changes and modifications within the scope of the present disclosure may be made without departing from the spirit thereof, and the disclosure includes all such modifications. Moreover aspects of one embodiment may be utilized in other, different embodiments.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2B schematically illustrates an exemplary annealing reaction between different microgel particles potentiated by linkers on the surface of the microgel particles.

FIG. 2C illustrates an exemplary process of tissue infiltration into a scaffold formed within a delivery site on tissue, where the boundary between the tissue and the microgels represents any interface between them, where cells can pass through the interface moving inwards from the tissue or outward toward the tissue from the microgels.

FIG. 3A illustrates a top down view of a microfluidic device according to one embodiment used to generate a plurality of microgel particles as part of a microporous gel system.

FIG. 3B illustrates a magnified view of the droplet generation region and downstream oil/surfactant pinching region (see box region in FIG. 3A).

FIG. 3C illustrates magnified, perspective views of two branch channels illustrated in FIG. 3A.

FIG. 3D illustrates a side view of the microfluidic device of FIG. 3A according to one embodiment.

FIG. 3E illustrates a photograph taken of a reduction to practice of the scheme illustrated in FIG. 3B where fluorescent solution on the left contains crosslinker, the fluorescent solution on the right contains polymer and reaction buffer, and the middle stream contains an inert liquid solution to prevent mixing of left and right solutions prior to droplet segmentation. Bright fluorescence between middle and right streams illustrates pH change in the middle stream due to diffusion of reaction buffer.

FIG. 3F illustrates a photograph of a reduction to practice of the scheme illustrated in FIG. 3B and FIG. 3E, while also showing the light microscopic view of droplet segmentation after the pinching oil streams are introduced.

FIG. 6A illustrates an exemplary dispensing device in the form of a double-barreled syringe according to one embodiment.

FIG. 6B illustrates an exemplary dispensing device in the form of a single-barreled syringe according to another embodiment.

FIG. 6C illustrates an exemplary dispensing device in the form of a tube that holds the microgel particles according to one embodiment.

FIG. 7A illustrates hematoxylin and eosin staining (H&E staining) of tissue sections in SKH1-Hr$^{hr}$ mice for tissue injected with the scaffold (Microporous Annealed Particle or "MAP" scaffold) as well as the non-porous control twenty-four (24) hours after injection.

FIG. 7B illustrates a graph of wound closure (%) as a function of days post-injection. This graphs shows that over a five (5) day period there is statistically significant improvement in the wound closure rates for using the scaffolds when compared to non-porous bilateral controls (N=5).

FIGS. 8A and 8B illustrate stained microscopic images of damaged tissue (i.e., wound site) that has been treated with the microgel scaffold (FIG. 8A) and with no treatment or "sham" (FIG. 8B) in a mouse model twenty-one (21) days after skin excision and gel application. The scar reduction enabled by the microgel scaffold can clearly be seen in FIG. 8A. Squares indicate hair follicles and oil glands (sebaceous glands) in the reforming tissue after gel application to a wound. Circles indicate remaining microgel particles in the reforming tissue.

FIG. 8C illustrates a graph showing the epidermal thickness for the tissue treated with the sham as well as tissue treated with the gel scaffold.

FIG. 8D illustrates a graph showing the number of sebaceous glands for the tissue treated with the sham as well as tissue treated with the gel scaffold.

FIG. 8E illustrates a graph showing the number of hair follicles for the tissue treated with the sham as well as tissue treated with the gel scaffold.

FIG. 8F illustrates a graph showing the scar width for the tissue treated with the sham as well as tissue treated with the gel scaffold.

FIG. 8G illustrates a graph showing the number of milial cysts for the tissue treated with the sham as well as tissue treated with the gel scaffold.

FIG. 13B illustrates an exemplary in vitro syringe injection. FIG. 13C illustrates an exemplary in vitro shape molding. FIG. 13D illustrates an exemplary in vitro annealed scaffold.

DETAILED DESCRIPTION OF THE ILLUSTRATED EMBODIMENTS

Figure 1:
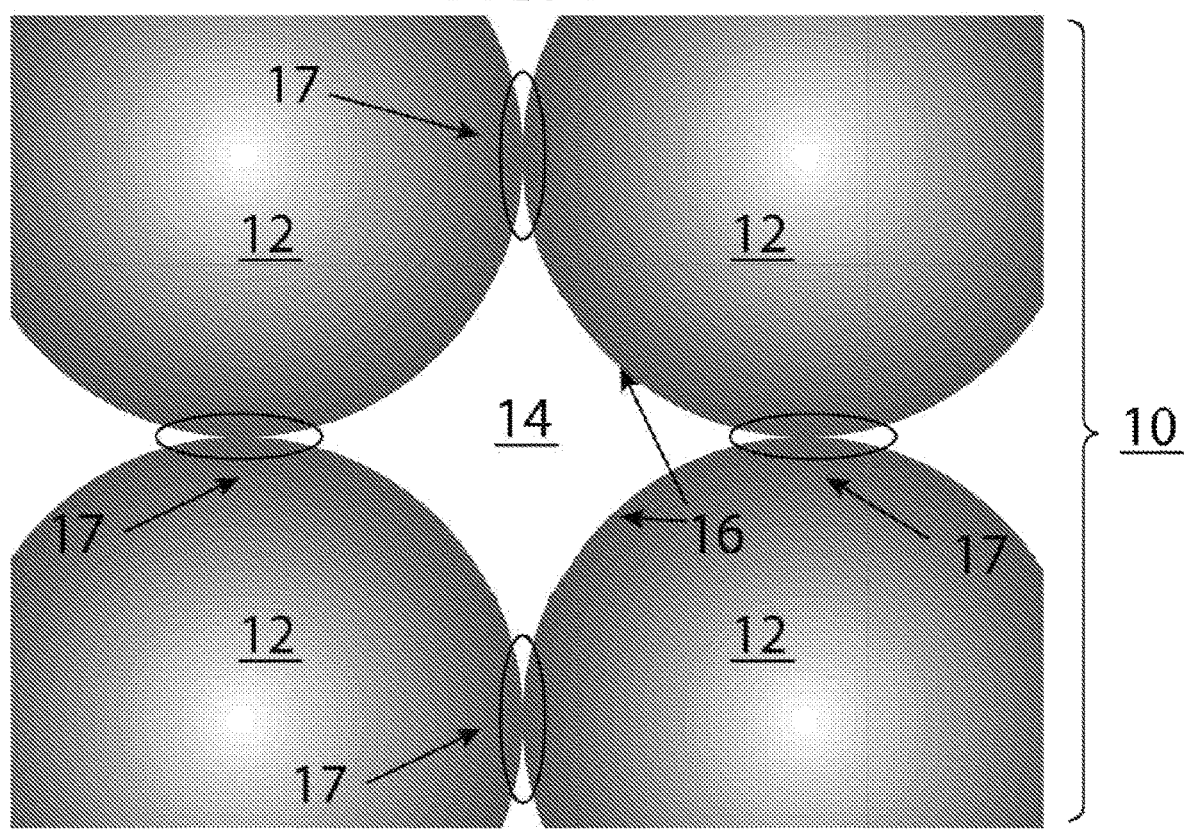
FIG. 1 illustrates a portion of a scaffold formed from a plurality of annealed microgel particles.

In the description of the preferred embodiment, reference is made to the accompanying drawings which form a part hereof, and in which is shown by way of illustration a specific embodiment in which the subject matter described herein may be practiced. It is to be understood that other embodiments may be utilized and structural changes may be made without departing from the scope and spirit of the inventive subject matter described herein. Further, various aspects of different embodiments may be utilized with other embodiments described herein without departing from the scope of the invention.

In one aspect of the subject matter described herein, a solid microgel scaffold for biomedical applications such as wound healing is disclosed that is formed when a plurality of microgel particles are annealed to one another in an annealing reaction. The annealing reaction, in one aspect of the subject matter described herein forms covalent bonds between adjacent microgel particles. For example, in the post-annealed state, the scaffold forms a three-dimensional structure that conforms to the site of application or delivery. Because of the imperfect packing of the microgel particles, the annealed scaffold formed from the particles includes interstitial spaces formed therein where cells can migrate, bind, and grow. The formed scaffold structure is porous upon annealing in the wound or other delivery site (unlike the non-porous solid scaffold provided by fibrin-based products). This porosity includes the interstitial spaces mentioned above as well as nanoscopic pores that may be created or formed in the particles themselves. The micro-porosity of the scaffold structure allows for high diffusivity of nutrients, cell growth and differentiation factors, as well as cell migration, ingrowth, and penetration. The microporosity of the scaffold provides for accelerated healing or improved therapeutic delivery of drugs or medicaments over conventional fibrin glue, hyper-branched polymers, or polymers with degradable crosslinker options, because of the enhanced cell migration through interstitial spaces while maintaining overall scaffold integrity. In addition, by not limiting the biomaterial to natural materials, the degradation profile and physical properties (e.g., stiffness, internal diffusivity, etc.) are improved, for example, by having a larger available range and a wider array of biological signals or therapeutically-active chemicals can be included within the material (e.g., antibiotics, steroids, growth factors, and the like can be loaded into the scaffold). Furthermore, the release or elution of the drugs, compounds, or other material to trigger or control biological activity, in certain embodiments, can be tuned through modification of the desired biomaterial. The signal compounds or molecules discussed above may be exposed to the tissue during the healing process or upon degradation of the scaffold. The signal compounds or molecules may also be released or eluted into the affected area after initial placement of the scaffold at the delivery site.

One advantage of the subject matter described herein beyond methods such as the STAR™ technology is that the formation of a scaffold occurs in vivo, allowing it to completely fill the desired space and be tuned to bind (chemically or otherwise) to the surrounding tissue. In addition, the pre-delivery formation of the microgel particles allows for controlled mechanical tunability of the resultant formed scaffold to match the properties of the surrounding tissue. These capabilities result in a better seal and overall integration with the tissue. Greater integration results in decreased possibility of material failure and enhanced long-term regeneration. This also helps prevent contamination from the environment. Moreover, the microporous nature of the annealed scaffold is beneficial to reduce immune foreign body response to the scaffold.

FIG. 1 illustrates a portion of the formed three dimensional scaffold 10 that is formed by a plurality of annealed microgel particles 12. The scaffold 10 includes interstitial spaces therein 14 that are voids that form micropores within the larger scaffold 10. The interstitial spaces 14 have dimensions and geometrical profiles that permit the infiltration, binding, and growth of cells. It should be appreciated that the microporous nature of the scaffold 10 disclosed herein involves a network of interstitial spaces or voids 14 located between annealed microgel particles 12 that form the larger scaffold structure. In one embodiment, the interstitial spaces or voids 14 created within the scaffold 10 exhibit negative concavity (e.g., the interior void surface is convex). FIG. 1 illustrates an exemplary void 14 with void walls 16 exhibiting negative concavity. The negative concavity is caused because the microgel particles 12 that are annealed to one another are generally or substantially spherical in shape in one preferred embodiment. This allows for the packing of microgel particles 12 that, according to one embodiment, produces a low void volume fraction between about 10% and about 50% and, in another embodiment between about 26% to about 36%. While the void volume fraction is low, the negative concavity exhibited in certain embodiments within the network of voids 14 provides a relatively high surface area to void volume for cells to interact with. For a given volume of cells, they would then, on average, be exposed to even more and larger surfaces (e.g., on the void walls 16) to interact within the network of voids in the scaffold 10.

It is important to note that the void network consists of regions where microgel surfaces are in close proximity (e.g., near neighboring annealed microgel particles 12) leading to high surface area adhesive regions for cells to adhere and rapidly migrate through, while neighboring regions further in the gaps between microgel particles 12 have a larger void space that can enable cell and tissue growth in this space. Therefore the combined adjacency of the tight void areas and more spacious void gaps is expected to have a beneficial effect on tissue ingrowth and regrowth, compared to either entirely small voids or all larger voids.

Note that in the embodiment described above, the negative concavity results due to the spherical shape of the microgel particles 12. In other embodiments, the microgel particles 12 might not be spherical in shape. Other non-spherical shapes may still be used in the scaffold 10. Still referring to FIG. 1, the scaffold 10 is formed by microgel particles 12 that are secured to one another via annealing surfaces 17. As explained herein, the annealing surfaces 17 are formed either during or after application of the microgel particles 12 to the intended delivery site.

Figure 2A:
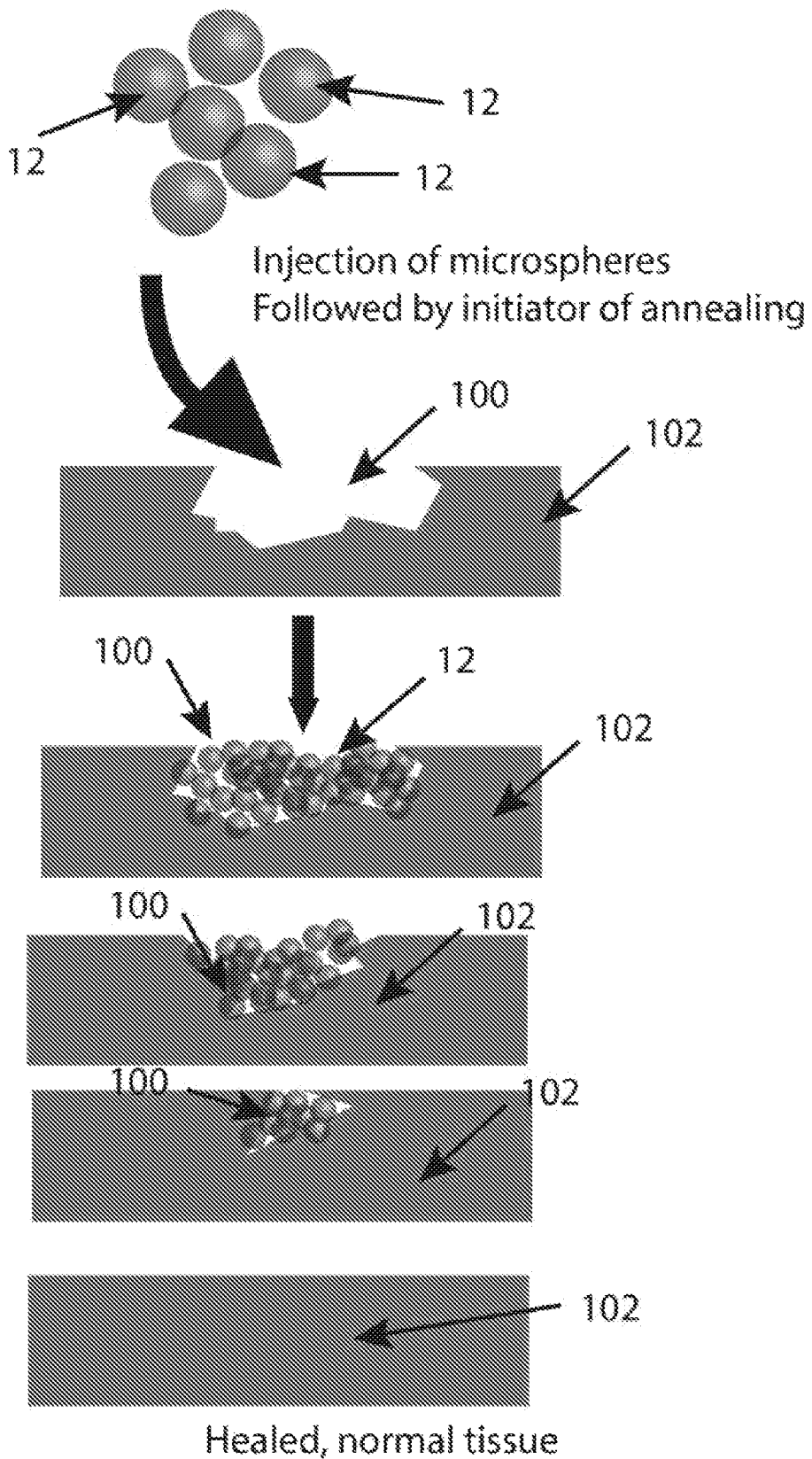
FIG. 2A illustrates an exemplary method of injecting microgel particles into a wound site for healing the same.

The scaffold 10 may be used for various applications, including a variety of medical applications such as military field medicine, medical trauma treatment, post-surgical closure, burn injuries, inflammatory and hereditary and autoimmune blistering disorders, etc. In one or more embodiments, the scaffold 10 is used as a tissue sealant (e.g., an acute wound-healing substance, surgical sealant, topical agent for partial thickness, full thickness, or tunneling wounds, pressure ulcers, venous ulcers, diabetic ulcers, chronic vascular ulcers, donor skin graft sites, post-Moh's surgery, post-laser surgery, podiatric wounds, wound dehiscence, abrasions, lacerations, second or third degree burns, radiation injury, skin tears, and draining wounds, and the like). FIGS. 2A-2C illustrate an embodiment, where the scaffold 10 is used to treat a wound site 100 formed in tissue 102 of a mammal. In certain embodiments, the scaffold 10 is used for immediate treatment of acute wounds. In acute wounds, the scaffold 10 provides several benefits, including a rapid method to seal wounds 100, prevent trans-epidermal water loss, provide cells or medication(s), and enhance the healing of skin wounds (e.g., surgical sites, burn wounds, ulcers) to provide more natural tissue development (e.g., avoiding the formation of scar tissue). One particular benefit of the scaffold 10 is the ability of the scaffold 10 to reduce or minimize the formation of scar tissue. The scaffold 10 provides a more effective alternative to tissue glues and other current injectable tissue fillers and adhesives.

As seen in FIG. 2A, microgel particles 12 are delivered to the wound site 100 followed by the initiation of the annealing reaction to anneal the microgel particles 12 to one another to form the scaffold 10. As seen in FIG. 2A, the wound site 100 is sealed by the scaffold 10 and as time progresses, the wound site 100 is healed into normal tissue (see also FIG. 11). FIG. 2B illustrates how adjacent microgel particles 12 (particle A and particle B) undergo chemical or enzymatic initiation of the annealing reaction to form an annealing surface 17 between microgel particles 12. FIG. 2C illustrates a magnified view illustrating how the scaffold 10 acts as a structural support yet permits the tissue infiltration and biomaterial resorption due to the porous nature of the scaffold 10. A cell 106 is illustrated infiltrating the interstitial spaces formed within the scaffold 10.

The scaffold 10 may also be used in a regenerative capacity, for example, applied to tissue for burns, acute and chronic wounds, and the like. In one embodiment, the scaffold 10 is used for chronic wounds. In chronic wounds, where the normal healing process is inhibited, the scaffold 10 can be used not only to seal wounds, but also to remove excess moisture, and apply medication(s), including cellular therapies that can assist in promoting the normal wound healing process. In the case of tissue filler applications for volume loss related to aging, lipoatrophy, lipodystrophy, dermal scarring, or superficial or deep rhytides, injection of the microgel particles 12 directly into the dermis via needle or cannula may be used to improve tissue contour, tissue loss, or tissue displacement. Because cells used in regenerative medicine can grow within the microgel particles 12, cells (e.g., mesenchymal stem cells, fibroblasts, etc.) may be included as a therapy by initially polymerizing the cells (1-20 cells) within microgel particles, or cells may be initially adhered to microgel particles, or cells may be introduced with the microgel particle solution (non-adhered), prior to annealing in situ in tissue.

The scaffold 10 may also be used for in vitro tissue growth, three-dimensional (3D) matrices for biological science studies, and cosmetic and dermatologic applications. For example, cancer cells could be seeded along with the microgel precursors and once annealed could allow for rapid 3D growth of tumor spheroids for more physiologically-relevant drug testing without the need for matrix degradation as would be required for other 3D culture gels (e.g., Matrigel®). It is expected that the rapid ability to form contacts between cells in the 3D matrix of the annealed gel will enhance growth and formation of micro-tissues from a single cell type or multiple cell types which can be used to screen for drugs or test cosmetics. Epidermal layers can form over the surface of a scaffold 10, which could allow testing of drugs or cosmetics on a more skin-like substitute compared to animal models. Previous 3D culture materials either can enable cell seeding within the gel uniformly through the volume, but not maintain cell-cell contacts because of the lack of porosity, or create porosity but require cells to be seeded following fabrication and migrate into the scaffold.

As explained herein, while the annealed scaffold 10 generally forms a defined structure, the precursor materials prior to final annealing is flowable and can be delivered as paste, slurry, or even injected to the delivery site of interest. Other injectable hydrogels can provide a scaffold for in situ tissue regrowth and regeneration, however these injected materials require gel degradation prior to tissue reformation limiting their ability to provide physical support. The injectable microporous gel system described herein circumvents this challenge by providing an interconnected microporous network for simultaneous tissue reformation and material degradation.

Microfluidic formation enables substantially monodisperse microgel particles 12 to form into an interconnected microporous annealed particle scaffold 10 (in one aspect of the subject matter described herein), thereby enabling the controlled chemical, physical, and geometric properties of the microgel particles 12 (e.g., building blocks), to provide downstream control of the physical and chemical properties of the assembled scaffold 10. In vitro, cells incorporated during scaffold 10 formation proliferate and form extensive three-dimensional networks within forty-eight (48) hours. In vivo, the injectable gel system that forms the scaffold 10 facilitates cell migration resulting in rapid cutaneous tissue regeneration and tissue structure formation within five (5) days. The combination of microporosity and injectability achieved with the scaffolds 10 enables novel routes to tissue regeneration in vivo and tissue creation de novo.

FIG. 2A illustrates the scaffold 10 formed within a wound site 100. Successful materials for tissue regeneration benefit from precisely matching the rate of material degradation to tissue development. If degradation occurs too quickly then insufficient scaffolding will remain to support tissue ingrowth. Conversely, a rate that is too slow will prevent proper tissue development and can promote fibrosis and/or immune rejection. Tuning of degradation rates based on local environment has been approached using hydrolytically and enzymatically degradable materials. However, decoupling loss of material mechanical stability with cellular infiltration has proven extremely challenging. Promotion of cellular infiltration into the material can also be approached using a lightly crosslinked matrix, however this often results in mechanical mismatch with surrounding tissues and poor material stability. Alternatively, the hydrogel degradation rate can be tuned by altering the polymeric backbone identity or crosslinking density, matching the rates of degradation and tissue formation. Although these techniques can be tuned to address specific applications of injectable hydrogels, they do not provide a robust pathway to achieve bulk tissue integration that does not rely on loss of material stability.

Every wound site is unique in its physical, chemical, and degradation requirements for functional tissue regeneration, requiring a material strategy that is robust to a variety of challenging environments. The microporous gel system and the resulting scaffold 10 that is created as described herein circumvents the need for material degradation prior to tissue ingrowth by providing a stably linked interconnected network of micropores for cell migration and bulk integration with surrounding tissue. The microporous gel system achieves these favorable features by, according to one embodiment, using the self-assembly of microgel particles 12 as "building blocks" or "sub-units" formed by microfluidic water-in-oil droplet segmentation. According to one embodiment, the microgel particles 12 formed in this manner are substantially monodisperse. The microgel particles 12 can be injected and molded into any desired shape. Lattices of microgel particles 12 are then annealed to one another via surface functionalities to form an interconnected microporous scaffold 10 either with or without cells present in the interconnected porous networks. The scaffold 10 preferably, in one embodiment, includes covalently linked microgel particles 12 that form a three-dimensional scaffolding 10 for tissue regeneration and ingrowth.

By combining injectability and microporosity, the microporous gel system provides an ideal biomaterial scaffold for efficient cellular network formation in vitro and bulk tissue integration in vivo. The modular microporous gel system also provides mechanical support for rapid cell migration, molecular cues to direct cell adhesion, and resorption during and after tissue regeneration. Through microfluidic fabrication, the chemical, physical, and geometric properties of the microgel particles 12 can be predictably and uniformly tailored, allowing for downstream control of the properties of the emergent scaffolds 10. The novel building block-based approach in which robustly achieved imperfect self-assembly is desirable to achieve microporosity fundamentally changes the use and implementation of hydrogels as tissue mimetic constructs, providing a philosophical change in the approach to injectable scaffolding for bulk tissue integration.

In one aspect of the subject matter described herein, the microporous gel system uses microgel particles 12 having diameter dimensions within the range from about 5 μm to about 1,000 μm. The microgel particles 12 may be made from a hydrophilic polymer, amphiphilic polymer, synthetic or natural polymer (e.g., poly(ethylene glycol) (PEG), poly (propylene glycol), poly(hydroxyethylmethacrylate), hyaluronic acid (HA), gelatin, fibrin, chitosan, heparin, heparan, and synthetic versions of HA, gelatin, fibrin, chitosan, heparin, or heparan). In one embodiment, the microgel particle 12 is made from any natural (e.g., modified HA) or synthetic polymer (e.g., PEG) capable of forming a hydrogel. In one or more embodiments, a polymeric network and/or any other support network capable of forming a solid hydrogel construct may be used. Suitable support materials for most tissue engineering/regenerative medicine applications are generally biocompatible and preferably biodegradable. Examples of suitable biocompatible and biodegradable supports include: natural polymeric carbohydrates and their synthetically modified, crosslinked, or substituted derivatives, such as gelatin, agar, agarose, crosslinked alginic acid, chitin, substituted and cross-linked guar gums, cellulose esters, especially with nitrous acids and carboxylic acids, mixed cellulose esters, and cellulose ethers; natural polymers containing nitrogen, such as proteins and derivatives, including cross-linked or modified gelatins, and keratins; vinyl polymers such as poly(ethyleneglycol)acrylate/methacrylate/vinyl sulfone/maleimide/norbornene/allyl, polyacrylamides, polymethacrylates, copolymers and terpolymers of the above polycondensates, such as polyesters, polyamides, and other polymers, such as polyurethanes; and mixtures or copolymers of the above classes, such as graft copolymers obtained by initializing polymerization of synthetic polymers on a preexisting natural polymer. A variety of biocompatible and biodegradable polymers are available for use in therapeutic applications; examples include: polycaprolactone, polyglycolide, polylactide, poly(lactic-co-glycolic acid) (PLGA), and poly-3-hydroxybutyrate. Methods for making networks from such materials are well-known.

In one or more embodiments, the microgel particles 12 further include covalently attached chemicals or molecules that act as signaling modifications that are formed during microgel particle 12 formation. Signaling modifications includes the addition of, for example, adhesive peptides, extracellular matrix (ECM) proteins, and the like. Functional groups and/or linkers can also be added to the microgel particles 12 following their formation through either covalent methods or non-covalent interactions (e.g., electrostatic charge-charge interactions or diffusion limited sequestration). Crosslinkers are selected depending on the desired degradation characteristic. For example, crosslinkers for the microgel particles 12 may be degraded hydrolytically, enzymatically, photolytically, or the like. In one particular preferred embodiment, the crosslinker is a matrix metalloprotease (MMP)-degradable crosslinker.

Examples of these crosslinkers are synthetically manufactured or naturally isolated peptides with sequences corresponding to MMP-1 target substrate, MMP-2 target substrate, MMP-9 target substrate, random sequences, Omi target sequences, Heat-Shock Protein target sequences, and any of these listed sequences with all or some amino acids being D chirality or L chirality. In another embodiment, the crosslinker sequences are hydrolytically degradable natural and synthetic polymers consisting of the same backbones listed above (e.g., heparin, alginate, poly(ethyleneglycol), polyacrylamides, polymethacrylates, copolymers and terpolymers of the listed polycondensates, such as polyesters, polyamides, and other polymers, such as polyurethanes).

In another embodiment, the crosslinkers are synthetically manufactured or naturally isolated DNA oligos with sequences corresponding to: restriction enzyme recognition sequences, CpG motifs, Zinc finger motifs, CRISPR or Cas-9 sequences, Talon recognition sequences, and transcription factor-binding domains. Any of the crosslinkers from the listed embodiments one are activated on each end by a reactive group, defined as a chemical group allowing the crosslinker to participate in the crosslinking reaction to form a polymer network or gel, where these functionalities can include: cysteine amino acids, synthetic and naturally occurring thiol-containing molecules, carbene-containing groups, activated esters, acrylates, norborenes, primary amines, hydrazides, phosphenes, azides, epoxy-containing groups, SANPAH containing groups, and diazirine containing groups.

In one embodiment, the chemistry used to generate microgel particles 12 allows for subsequent annealing and scaffold 10 formation through radically-initiated polymerization. This includes chemical-initiators such as ammonium persulfate combined with Tetramethylethylenediamine. Alternatively, photoinitators such as Irgacure® 2959 or Eosin Y together with a free radical transfer agent such as a free thiol group (used at a concentration within the range of 10 µM to 1 mM) may be used in combination with a light source that is used to initiate the reaction as described herein. One example of a free thiol group may include, for example, the amino acid cysteine, as described herein. Of course, peptides including a free cysteine or small molecules including a free thiol may also be used. Another example of a free radical transfer agent includes N-Vinylpyrrolidone (NVP).

Alternatively, Michael and pseudo-Michael addition reactions, including $\alpha,\beta$-unsaturated carbonyl groups (e.g., acrylates, vinyl sulfones, maleimides, and the like) to a nucleophilic group (e.g., thiol, amine, aminoxy) may be used to anneal microgel particles 12 to form the scaffold 10. In another alternative embodiment, microgel particle 12 formation chemistry allows for network formation through initiated sol-gel transitions including fibrinogen to fibrin (via addition of the catalytic enzyme thrombin).

Functionalities that allow for particle-particle annealing are included either during or after the formation of the microgel particles 12. In one or more embodiments, these functionalities include $\alpha,\beta$-unsaturated carbonyl groups that can be activated for annealing through either radical initiated reaction with $\alpha,\beta$-unsaturated carbonyl groups on adjacent particles or Michael and pseudo-Michael addition reactions with nucleophilic functionalities that are either presented exogenously as a multifunctional linker between particles or as functional groups present on adjacent particles. This method can use multiple microgel particle 12 population types that when mixed form a scaffold 10. For example, microgel particle 12 of type X presenting, for example, nucleophilic surface groups can be used with microgel particle 12 type Y presenting, for example, $\alpha,\beta$-unsaturated carbonyl groups. In another embodiment, functionalities that participate in Click chemistry can be included allowing for attachment either directly to adjacent microgel particles 12 that present complimentary Click functionalities or via an exogenously presented multifunctional molecule that participates or initiates (e.g., copper) Click reactions.

The annealing functionality can include any previously discussed functionality used for microgel crosslinking that is either orthogonal or similar (if potential reactive groups remain) in terms of its initiation conditions (e.g., temperature, light, pH) compared to the initial crosslinking reaction. For example if the initial crosslinking reaction consists of a Michael-addition reaction that is temperature dependent, the subsequent annealing functionality can be initiated through temperature or photoinitiation (e.g., Eosin Y, Irgacure®). As another example, the initial microgels may be photopolymerized at one wavelength of light (e.g., ultraviolent with Irgacure®), and annealing of the microgel particles 12 occurs at the same or another wavelength of light (e.g., visible with Eosin Y) or vice versa. Besides annealing with covalent coupling reactions, annealing moieties can include non-covalent hydrophobic, guest/host interactions (e.g., cyclodextrin), hybridization between complementary nucleic acid sequences or nucleic acid mimics (e.g., protein nucleic acid) on adjoining microgel particles 12, or ionic interactions. An example of an ionic interaction would consist of alginate functionality on the microgel particle surfaces that are annealed with Ca2+. So-called "A+B" reactions can be used to anneal microgel particles 12 as well. In this embodiment, two separate microgel types (type A and type B) are mixed in various ratios (between 0.01:1 and 1:100 A:B) and the surface functionalities of type A react with type B (and vice versa) to initiate annealing. These reaction types may fall under any of the mechanisms listed herein.

In one embodiment, the microgel particles 12 are fabricated using either microfluidic or millifluidic methods, generating deterministic microgel particle length scales with small variability and in high throughput (e.g., frequencies greater than 10 particles/second). The coefficient of variation of the microgel particle 12 length scale (e.g., diameter) can be within 35% or more preferably within 15% and even more preferably within 5% of the mean length scale. Milli- or microfluidics allow for uniform, pre-determined, concise material properties to be included pre-, in-, and post-formation of microgel particles 12. Furthermore, the microfluidic/millifluidic production mechanism allows for ease of scaling-up production as well as good quality control over chemical composition and physical characteristics of the microgel particles 12. The millifluidic and/or microfluidic technologies for microgel particle 12 generation are easily scalable processes to create large amounts of material for commercial needs, while maintaining high accuracy and precision in microgel particle 12 characteristics. Moreover, this is all accomplished at low cost in comparison to other technologies involving electrospinning or large-scale fibrin purification.

In one embodiment, microgel particles 12 are formed using automated fluidic methods relying on water-in-oil emulsion generation. This includes microfluidic or millifluidic methods utilizing glass/PDMS, PDMS/PDMS, glass/glass, or molded/cast/embossed plastic chips to create water in oil droplets with a size distribution variation that is less than 35%.

FIGS. 3A-3F illustrates one embodiment of a microfluidic device 20 that is used to generate the microgel particles 12. The microfluidic device 20 is formed in a substrate material 22 such as PDMS which may include another substrate material 24 (e.g., glass) that is bonded the substrate 22. In this embodiment, the microfluidic device 20 includes a first inlet 26, a second inlet 28, and a third inlet 30. As seen in FIG. 3A, the third inlet 30 is interposed between the first inlet 26 and the second inlet 28. In this embodiment, the first inlet 26 is coupled to a solution containing a 4-arm poly (ethylene glycol) vinyl sulfone (PEG-VS) backbone (20 kDa) that has been pre-modified with oligopeptides for cell adhesive properties (e.g., RGD) and surface/tissue annealing functionalities (e.g., K and Q peptides). The PEG-VS backbone may be prefunctionalized with 500 µM K-peptide (Ac-FKGGERCG-NH$_2$ [SEQ ID NO: 1]) (Genscript), 500 µM Q-peptide (Ac-NQEQVSPLGGERCG-NH$_2$ [SEQ ID NO: 2]), and 1 mM RGD (Ac-RGDSPGERCG-NH$_2$ [SEQ ID NO: 3]) (Genscript). The solution input to the first inlet 26 may contain about 5% (on a weight basis) modified PEG-VS contained in a buffer of 0.3 M triethanolamine (Sigma), pH 8.25. The second inlet 28 is coupled to a solution containing the crosslinker, which in one embodiment, is an 12 mM di-cysteine modified Matrix Metalloprotease (MMP) (Ac-GCRDGPQGIWGQDRCG-NH$_2$ [SEQ ID NO: 4]) substrate (Genscript). In experiments conducted that utilized florescent imaging, the MMP substrate was pre-reacted with 10 µM Alexa-fluor 647-maleimide (Life Technologies). Of course, in practical applications, the use of the fluorescent probe is not needed. All solutions can be sterile filtered through a 0.2 μm Polyethersulfone (PES) membrane in a Luer-lock syringe filter.

As used herein, K-peptides refer to those peptides that contain therein a Factor XIIIa recognized lysine group. As used herein, Q-peptides refer to those peptides that contain therein a Factor XIIIa recognized glutamine group. Thus, peptide sequences beyond those specifically mentioned above may be used. The same applies to the RGD peptide sequence that is listed above.

The third inlet 30 is coupled to an aqueous solution containing 5% by weight of PEG-VS (unmodified by K, Q, or RGD peptides). The aqueous PEG-VS solution is preferably viscosity-matched with the PEG-VS solution introduced via the first inlet 26 and can be used to control the pH of the crosslinker solution and to inhibit crosslinking until droplet formation. By having the third inlet 30 interposed between the first inlet 26 and the second inlet 28 the aqueous PEG-VS solution acts as a barrier that prevents any material diffusive mixing of reactive solutions upstream of the droplet generation region. This significantly increases the lifespan of the device before fouling occurs. FIGS. 3E and 3F illustrate how the inert liquid solution prevents mixing of left and right solutions prior to droplet segmentation. Note that the method of making the microgel particles 12 will also work with omitting the third inlet 30, and adjusting peptide/crosslinker concentrations accordingly, yet the lifespan of the device will not be as long.

Referring to FIGS. 3A, 3B, and 3C, the first inlet 26, second inlet 28, and third inlet 30 are connected to, respectively, channels 32, 34, 36. The channels intersect at junction 38 and are carried in a common channel 40. The fourth inlet 42 is provided in the device and is coupled to an oil phase that contains a surfactant (e.g., 1% SPAN® 80 by volume although other surfactants can be used). The fourth inlet 42 is connected to two channels 44, 46 that intersect at junction 48 at a downstream region of the common channel 40. The junction 48 in the device 20 is where the aqueous-based droplets are formed that include the PEG-VS component and the crosslinker. The contents of the droplets undergo mixing and will form the microgel particles 12 upon gelation, which in this embodiment is a function of the ambient temperature and the passage of time. In this device, a fifth inlet 50 is provided that is coupled to another oil phase that contains a surfactant at a higher volumetric percentage than that connected to the fourth inlet 42. For example, the fifth inlet 50 can be connected to an oil phase containing 5% SPAN® 80 by volume. Again, other surfactants besides SPAN® 80 could also be used. The fifth inlet 50 is connected to two channels 52, 54 that intersect at junction 56 in a pinching orientation as illustrated.

The common channel 40 continues to a series of progressively branching branch channels 58. The branch channels 58 permit continuous flow of the microgel particles 12 through individual parallel channels where local environmental conditions can be optionally controlled. For example, temperature of the individual branch channels 58 can be controlled to regulate crosslinking conditions for the microgel particles 12. Likewise, the branch channels 58 may be illuminated with light to control light-activated reactions. The microgel particles 12 may be removed from the device 20 using the outlet 59. It should be understood, however, that regulation of the temperature of the branch channels 58 or the use of light activation is entirely optional as the cross-linking reaction may occur just through the passage of time when the device is operated at or around ambient temperatures.

As best seen in FIG. 3D, the first inlet 26, second inlet 28, third inlet 30, fourth inlet 42, and fifth inlet 50 are connected, respectively, to fluid lines 26', 28', 30', 42', and 50' that connect to a pumping device 51 or multiple pumping devices 51 that pumps respective fluids into the correspondingly connected inlets 28, 28, 30, 42, 50. The pumping device 51 may include separate pumps tied to each different fluid. Examples of types of pumps that may be used include syringe pumps or other pumps commonly used in connection with microfluidic devices. In one aspect, the pumping device 51 uses regulated pressurized gas above a fluid reservoir to pump fluid at the desired flow rate(s) through the device.

Figure 4A:
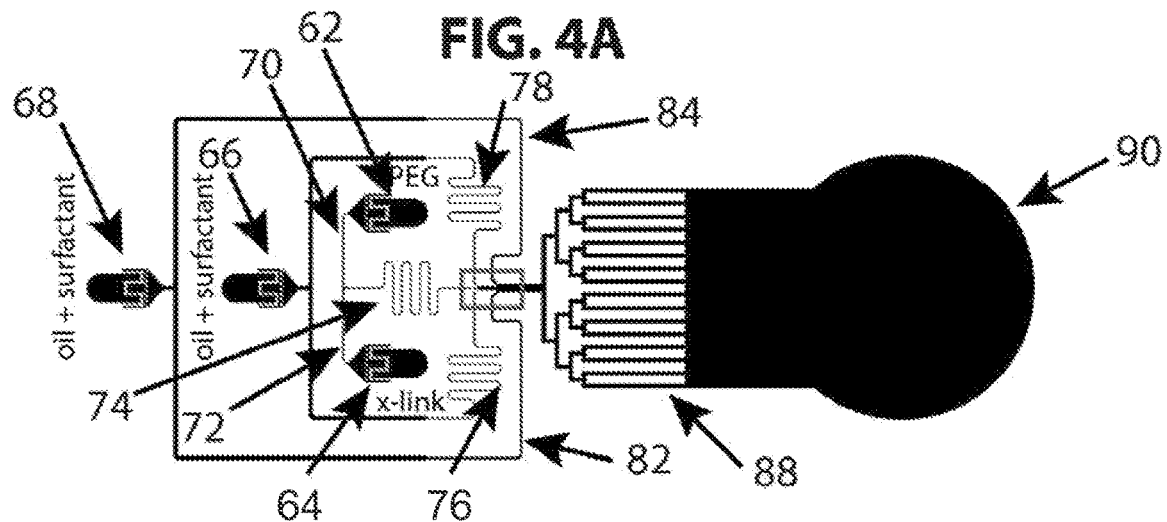
FIG. 4A illustrates a top down view of a microfluidic device according to another embodiment used to generate a plurality of microgel particles as part of a microporous gel system.
Figure 4B:
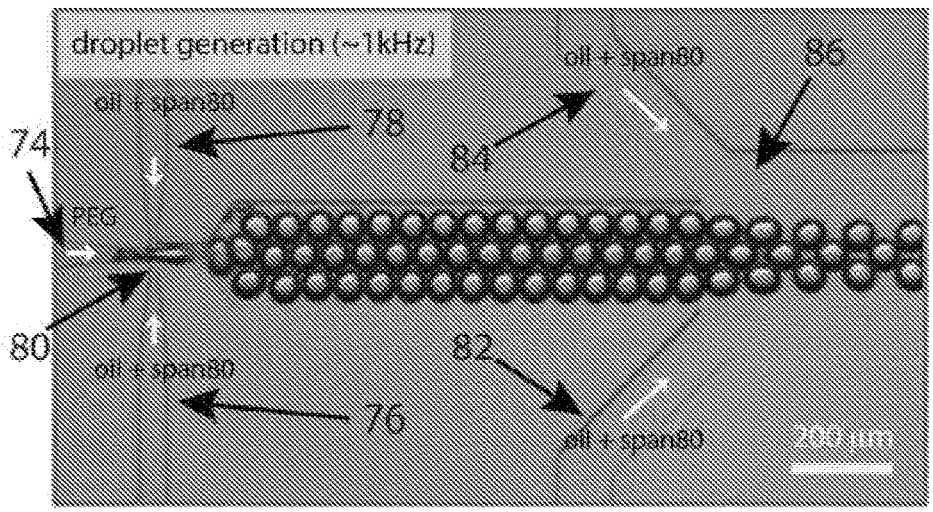
FIG. 4B illustrates that in the droplet segmentation region, mineral oil with 0.25% Span® 80 pinches and segments PEG pre-gel, and downstream a 5% Span® 80 solution in mineral oil mixes and prevents downstream coalescence of microgels before complete gelation.
Figure 4C:
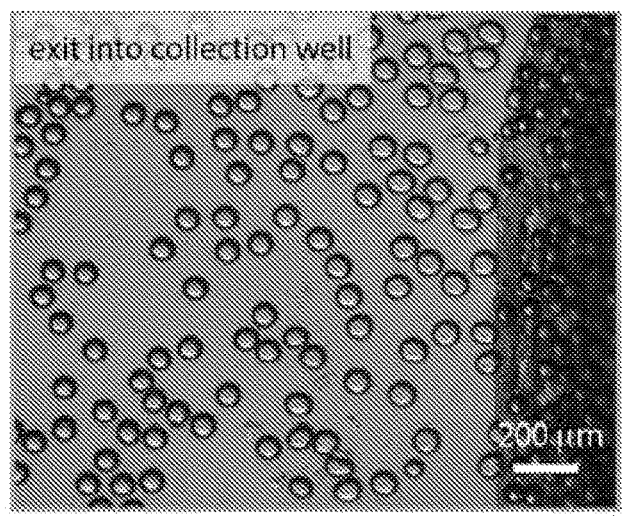
FIG. 4C illustrates droplets do not recombine during incubation in the bifurcation region and exit from the microchannel to the collection well.

FIGS. 4A-4C illustrate an alternative embodiment of a microfluidic device 60 that is used to generate the microgel particles 12. In this alternative embodiment, unlike the embodiment of FIGS. 3A-3C, there is no third inlet 30 that carries an aqueous solution that is used to separate the PEG and crosslinking components prior to droplet generation. Rather, in this embodiment, the microfluidic device 60 includes first inlet 62, a second inlet 64, a third inlet 66, and a fourth inlet 68. The first inlet 62 is coupled to a modified PEG-VS source such as that described above. The second inlet 64 is coupled to a crosslinking agent. The third inlet 66 is coupled to a source containing oil and a surfactant. The fourth inlet 68 is coupled to a source containing oil and a surfactant at a higher concentration than that coupled to the third inlet 66. In this embodiment, the first inlet 62 and the second inlet 64 are coupled to respective channels 70, 72 that lead to a common channel 74. The third inlet 66 is coupled to a pair of channels 76, 78 that intersect with the common channel 74 at a junction 80 (best seen in FIG. 4B) where droplet generation occurs (droplets will form the microgel particles 12 upon reaction). The fourth inlet 68 is coupled to a pair of channels 82, 84 that intersect with the common channel 74 at a downstream location 86 (best seen in FIG. 4B) with respect to junction 80. As seen in FIG. 4A, the device 60 includes a series of progressively branching branch channels 88 which are similar to those described in the context of the embodiment of FIGS. 3A-3C. Microgel particles 12 passing through branch channels 88 may be collected in a collection chamber 90 or the like which can be removed from the device 60. Fluid is delivered to the device 60 using fluid lines and a pumping device as described previously in the context of the embodiment of FIGS. 3A-3C.

The fluidic conditions that lead to microgel particle 12 formation include, in one embodiment, on-chip mixing of a PEG-based and crosslinker-based aqueous solutions, where one part contains base polymer and the other contains the crosslinking or initiating agent. Of course, in the embodiment of FIGS. 3A-3C, there is a three-input mixing which includes the aforementioned components plus the addition of the aqueous-based inert stream. These PEG and crosslinker solutions are mixed at either a 1:1 volumetric ratio, or another controllable ratio (controlled by relative flow rates into the device) up to 1:100. The ratios of the oil and total aqueous flow rates are controlled to determine a specific size microgel particle 12, where these ratios can range from 4:1 (aqueous:oil) down to 1:10 (aqueous:oil).

As explained above, in the embodiment of FIGS. 3A-3D, the chip device 20 is designed to have three aqueous-based solutions combined to form the microgel particles 12, wherein the base polymer and crosslinking/initiating agent are separated by a non-reactive solution upstream of the droplet generator to prevent reaction of solutions and fouling of the chip over time in the region upstream of droplet generation. In this configuration the portion of non-reactive solution should be equal to or less than base and cross-linker solutions, from 1 to 0.05 times of the volume rate of the other solutions. This embodiment can thus improve the reliability and lifetime of chips used for microgel generation. In addition, in this or the previous embodiment, cells can be introduced into either of the two or three introduced aqueous solutions to enable encapsulation of these cells (single cells or clusters of 2-20 cells per particle) within microgel particles 12 such that encapsulated cells can produce factors to enhance wound healing or cell ingrowth.

Figure 5:
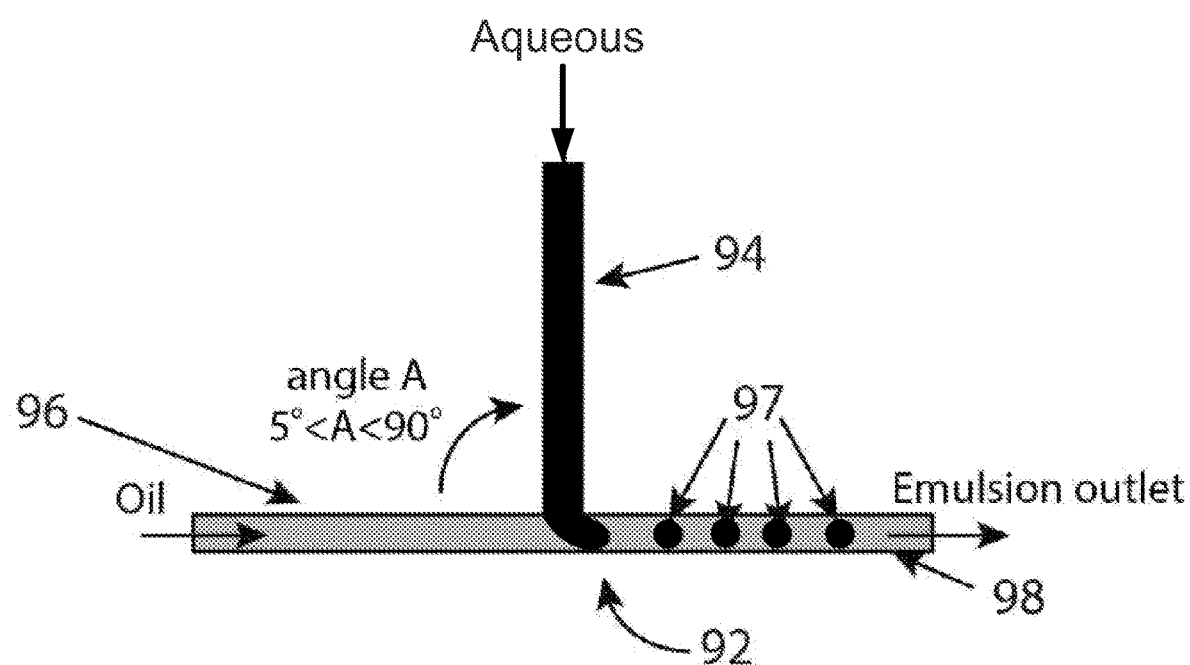
FIG. 5 illustrates an exemplary microfluidic T-junction that may be used to generate microgel droplets according to one embodiment.

While FIGS. 3A-3D and 4A-4C illustrate different embodiments of a microfluidic device 20, 60 that may be used to generate the microgel particles 12, in an alternative embodiment, the microfluidic flow path may include a 'T-junction' architecture such as that illustrated in FIG. 5. In this embodiment, the microfluidic device 92 includes a junction formed between a first channel 94 that carries the aqueous phase while a second channel 96 includes the oil phase. Droplets 97 are formed and carried via an outlet channel 98 (which may be the same as the first or second channels 94, 96). Alternatively, different droplet formation configurations may be used to generate the microgel particles 12. For example, the device may generate droplets 97 using the gradient of confinement due to non-parallel top and bottom walls such as that disclosed in Dangla et al., Droplet microfluidics driven by gradients of confinement, Proc Natl Acad Sci USA, 110(3): 853-858 (2013), which is incorporated by reference herein.

In the microfluidic devices described above, the channel surfaces should be modified such that the aqueous phase is non-wetting, which can include a fluorination of the surface, or converting the surfaces to become hydrophobic or fluorophilic, either by a covalent silane-based treatment or another non-specific adsorption based approach. Alternatively, a plastic polymer containing fluorophilic groups comprises the chip material and can be combined with the previously mentioned surface coatings or without a surface coating. Further, the oil used in the preferred embodiment should be either a mineral oil (paraffin oil) supplemented with a non-ionic surfactant, vegetable oil supplemented with an ionic surfactant, or a fluorinated oil supplemented with a fluorinated surfactant (or any combination of these two oil/surfactant systems). These microfluidic or millifluidic methods generate monodisperse (coefficient of variation less than 35%) populations of microgel particles 12 in rates equal to or exceeding 10 Hz, where collection is accomplished manually (by hand) or using automated fluidic handling systems. To prevent coalescence of microgel particles 12 prior to completion of the crosslinking reaction sufficient surfactant is necessary to stabilize the pre-gel droplets, however, high levels of surfactant also destabilize the droplet generation process. Therefore, a preferred embodiment of the microfluidic system for microgel particle 12 generation includes a low concentration of surfactant in the initial pinching oil flow (1% or less) that creates droplets followed by addition of an oil+surfactant solution from a separate inlet that is merged with the formed droplet and oil solution and contains a higher level of surfactant (up to 10 times or even 50 times higher than the initial surfactant). This is illustrated, for example, in the embodiments of FIGS. 3A-3D and 4A-4C.

In another alternative embodiment, the two oil pinching flows have the same concentration of surfactant. In still another embodiment, there is not a second pinching oil flow, and only the flow-focusing oil flow to generate droplets. Moreover, as explained above, in some alternative embodiments, there is no second pinching oil flow and only the t-junction oil flow is used to generate droplets. Of course, the t-junction droplet junction may optionally be combined with a second focusing oil inlet with equal or greater surfactant concentration.

After formation, microgel particles 12 are extracted from the oil phase using either centrifugation through an aqueous phase, or filtration through a solid membrane filtration device. For example, filtration may be used to reduce the volume of free aqueous solution holding the microgel particles 12 (free volume). In one embodiment, the aqueous free volume is less than about 35% of the total volume. In another embodiment, for generation of intentionally polydisperse populations, microgel particle generation is carried out in a milli- or microfluidic platform, generating stocks of relatively monodisperse microgel particles 12 that are then mixed at desired ratios to obtain deterministic distributions and ratios of microgel particle 12 sizes. Ratios of microgel particle 12 sizes can be controlled precisely to control pore structure, or chemical properties in a final annealed scaffold 10 with stoichiometric ratios from: 1:1, 10:1, or exceeding 100:1.

Alternatively, generation of microgel particles 12 via a water-in-oil system can also be carried out using sonic mixing methods or a rotating vortex. These latter methods generate polydisperse populations of microgel particles 12 with size ranges from 100 nanometers to 500 micrometers. These particles can then be filtered using porous filters, microfluidic filtration, or other techniques known in the art to obtain a narrower size distribution of microgel particles 12 (e.g., coefficient of variation less than 50%). As another alternative, the component microgel particles 12 of different shapes can be fabricated using stop flow lithography, continuous flow lithography, and other methods to create shaped particles that rely on shaping flows (see Amini et al. International Publication No. WO/2013/049404, which is incorporated by reference herein) combined with UV-initiated polymerization through a shape-defining mask. In this case the microgel particles 12 are non-spherical with long and short dimensions that can vary between 5 and 1000 micrometers. Shaped particles can also be fabricated by generating spherical particles in a water in oil emulsion, followed by extrusion of said particles through microfabricated constrictions that have length scales smaller than the diameter of the particle. The previously spherical particles adopt the shape of the constriction as they transition to a gel and retain that shape as they gel in the constriction by any of the crosslinker reactions listed above. The gels retain that shape after exiting the microfabricated construction. Shaped particles can allow for additional control of pores, overall porosity, tortuosity of pores, and improved adhesion within the final scaffold formed by microgel particle 12 annealing.

In one or more embodiments, the microgel particles 12 are either modified covalently or not (e.g., inclusion spatially within by diffusion) to provide biologically active molecules (e.g., small molecule drugs, antibiotics, peptides, proteins, steroids, matrix polymers, growth factors, antigens, antibodies, etc.). Inclusion of signaling molecules after formation of the microgel particle 12 may be accomplished through passive diffusion, surface immobilization (permanent or temporary), and/or bulk immobilization (permanent or temporary).

Figure 10:
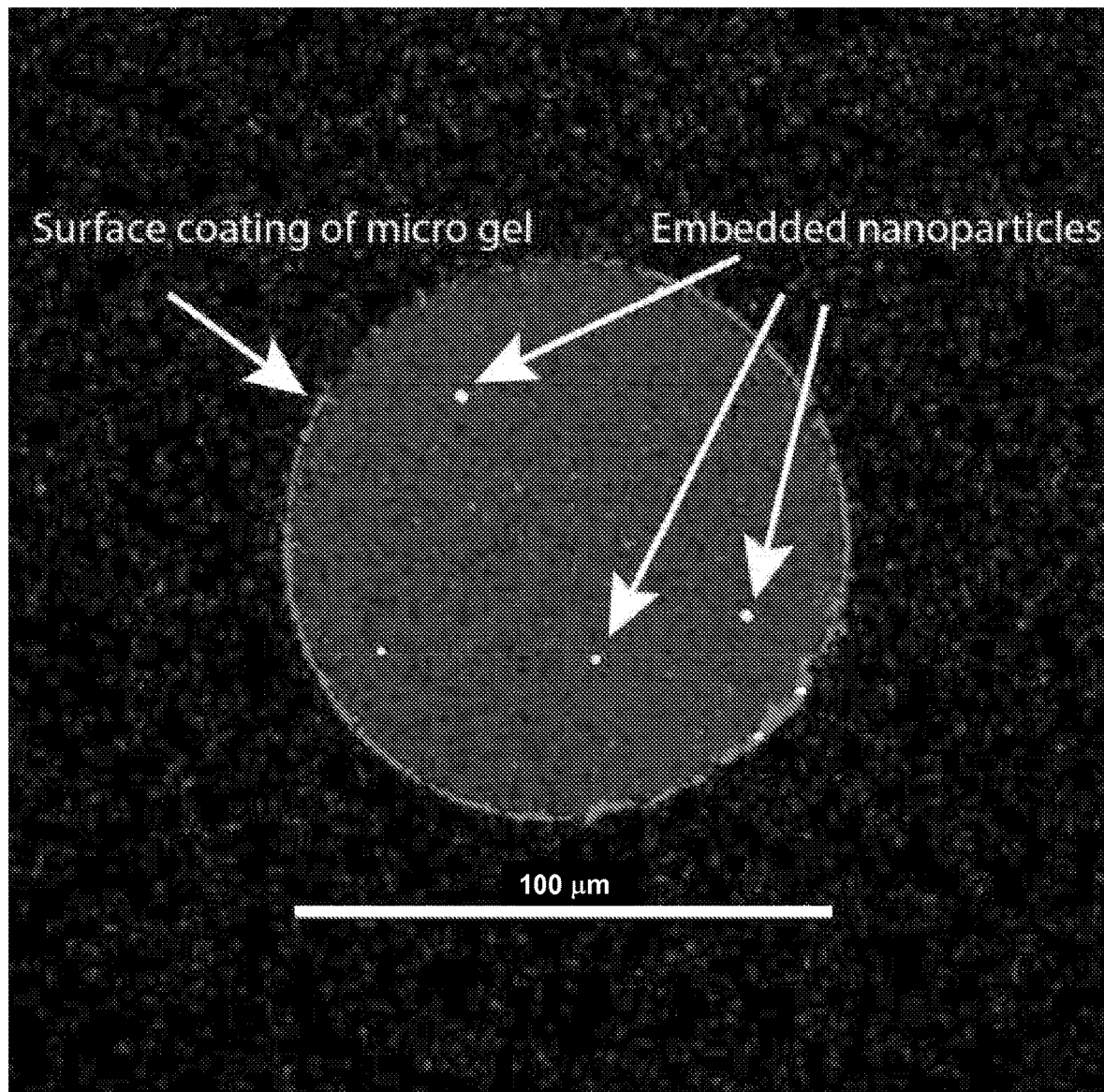
FIG. 10 shows a microgel fabricated using the described technique, where the surface of the microgel has been augmented with a fluorescent bovine serum albumin (BSA) protein (outer perimeter) through the use of phosphine-azide 'click' chemistry. Further, nanoparticles (500 nm) are embedded within the microgel during microfluidic fabrication.

In another embodiment, nanoparticles are included in the initial pre-polymer solution and incorporated in the microgel particles 12 during initial polymerization or gelation, and the nanoparticles may include biologically active molecules for sustained or rapid release and delivery. In another embodiment, microgel particles 12 containing free primary amines (included as part of a lysine-containing oligopeptides) can be modified with NHS-Azide. To this set of microgel particles 12 can be added a protein modified with a NHS-phosphine, resulting in surface-coating of the microgel particles 12 with the modified protein. FIG. 10 illustrates an embodiment in which a microgel particle 12 has nanoparticles embedded therein and a surface that has been modified with a protein using Click chemistry.

Following the production and optional modification, the microgel particles 12 (which can be a homogeneous or heterogeneous mixture) may be applied to a desired location (in vitro, in situ, in vivo). The desired location on mammalian tissue 102 can include, for example, a wound site 100 or other site of damaged tissue. The microgel particles 12 can be introduced alone in an aqueous isotonic saline solution or slurry (with preferably 30-99% volume fraction of microgel particles 12, and less preferably 1-30% volume fraction). Alternatively microgel particles 12 can be introduced along with cells as single-cells or aggregates with cell to particle ratios from 10:1 to create dense cell networks within the final annealed scaffold 10 or 1:100 or even 1:1000 to create sparsely seeded scaffolds 10 with cells that produce soluble factors useful for regeneration. In another embodiment microgel particles 12 can be cultured with cells at a low volume fraction of particles (<10%) for a period of time in cell-permissive media to promote adhesion to the individual microgel particles 12. These composite cell-adhered microgel particles 12 can be introduced as the active component that would anneal to form a microporous cell-seeded scaffold 10, which may be beneficial to enhance the speed of regenerative activity. Desired in vitro locations to introduce microgel particles 12 include well plates (e.g., 6-well, 96-well, 384-well) or microfluidic devices to form 3D microporous culture environments for cells following annealing, and enable subsequent biological assays or high-throughput screening assays with more physiologically-relevant 3D or multi-cellular conditions. For introduction in vitro, microgel particle 12 solutions can be pipetted into wells or introduced via syringe injection followed by introduction of an annealing solution or triggering of annealing photochemically. Alternatively, a solution of microgel particle 12 solution could be mixed with a slow acting annealing solution (annealing occurring over 10-30 min) before delivery. In situ locations include external wound sites (e.g., cuts, blisters, sores, pressure ulcers, venous ulcers, diabetic ulcers, chronic vascular ulcers, donor skin graft sites, post-Moh's surgery sites, post-laser surgery sites, podiatric wounds, wound dehiscence, abrasions, lacerations, second or third degree burns, radiation injury, skin tears and draining wounds, etc.). Since the epidermis is an epithelial structure, the microgel particle solution may be used to heal other epithelial surfaces (i.e., urothelial (bladder and kidney), aerodigestive (lung, gastrointestinal), similarly to skin epithelium (i.e., stomach or duodenal ulcer; following penetrating trauma to the lung, bladder or intestinal fistulas, etc.). Additionally, the microgel particle solution can be applied to other tissues through a catheter or cannula, such as nervous tissue and cardiac tissue where tissue ingrowth would be beneficial to prevent scarring and to facilitate regenerative healing following injury, such as after spinal cord trauma, cerebral infarction/stroke, and myocardial infarction.

For introduction in situ microgel particle containing solution can be stored separately from an annealing solution and be mixed during introduction (a method analogous to epoxy adhesives) to prevent premature initiation of the annealing reaction before entry into a wound site 100.

In another, the two solutions could be stored in a syringe or squeeze-tube applicator with two barrels of equal or unequal diameters, such that when the plunger of the syringe is depressed or squeeze tube is compressed it simultaneously delivers both the microgel particles 12 and annealing solution at the correct stoichiometry. FIG. 6A illustrates one such embodiment of a delivery device 110 that includes a first barrel 112, a second barrel 114, and a plunger 116 that is used to dispense the solution containing the microgel particles 12 from each barrel 112, 114. For example, the first barrel 112 contains microgel particles 12 and thrombin at a concentration ranging from 0.1 to 5 U/ml and the second barrel 114 contains the microgel particles 12 and FXIII at a concentration of 0.1 to 1,000 U/ml). In both barrels 112, 114 there is a 1 to 1 volume fraction of K and Q peptide containing microgel particles 12 where the concentration of K and Q peptides range from 10-1,000 µM in the microgel particles 12. In this embodiment, upon mixing the thrombin activates the FXIII (to form FXIIIa) and the resultant FXIIIa is responsible for surface annealing and linking of the K and Q peptides on the adjacent microgel particles 12.

Alternatively, the two barrels 112, 114 can contain two separate microgel particle 12 types with annealing moieties that require the combination to initiate cross-linking. An alternative storage and delivery method would be in a single barrel syringe 110 as illustrated in FIG. 6B or a multi-use or single-use compressible tube as illustrated in FIG. 6C (e.g., similar to toothpaste or antibiotic ointment) in which the microgel particle slurry can be squeezed out to a desired volume and spread over the wound site 100 and then annealed through exposure to light, where the active agent for photochemistry is Eosin-Y at a concentration of 100 µM although concentrations within the range of 10 µM-1 mM will also work. Preferably, Eosin-Y is accompanied with a radical transfer agent which can be, for example, a chemical species with a free thiol group. An example of one such radical transfer agent includes cysteine or peptides including cysteine(s) described herein (e.g., used at a concentration of 500 µM). The light should be delivered via a wide spectrum white light (incandescent or LED), or a green or blue LED light. A flashlight, wand, lamp, or even ambient light may be used to supply the white light. Exposure should occur between 0.1 seconds and 1000 seconds, and the intensity of light should range between 0.01 mW/cm$^2$ to 100 mW/cm$^2$ at the site of annealing. In another embodiment, light-mediated annealing can be accomplished using a UV light (wavelengths between 300-450 nm), where the agent for photochemistry is IRGACURE® 2959, at a concentration of 0.01% w/v to 10% w/v. The exposure time should be between 0.1 seconds and 100 seconds, with a light intensity of 0.1 mW/cm$^2$ to 100 mW/cm$^2$ at a site of annealing. For embodiments in which light initiated annealing is used, microgel precursors 12 would be stored in opaque (opaque with respect to wavelength range that initiates annealing) syringe or squeeze tubes 110 containers prior to use. Desired in situ locations include internal cuts and tissue gaps (e.g., from surgical incisions or resections), burn wounds, radiation wounds and ulcers, or in cosmetic surgery applications to fill the tissue location and encourage tissue ingrowth and regeneration rather than the fibrotic processes common to contemporary injectables.

Delivery using double or single barrel syringes is also suited to this indication as well as annealing using photo-activation and a UV or white light source that can be inserted into the surgical site. For both the in situ and in vivo applications the microgel particle slurry can be spread using a sterile applicator to be flush with the wound or mounded within and around the wound site 100 (within the wound and 2 mm to 1 cm beyond the original wound extents) to create an annealed scaffold that extends beyond the wound site 100 or tissue defect to provide additional protection, moisture, and structure to support tissue regeneration.

An annealing process is initiated through the application of a stimulus (e.g., radical initiator, enzyme, Michael addition, etc.) or through interactions with a stimulus that is already present at the site of application of the microgel particles 12 that interacts with functional groups on the surface of the microgel particles 12, forming a solid contiguous highly porous scaffold 10 formed from the annealed (linked) microgel particles 12. If used in tissue, the annealing process can allow for fusion of the scaffold 10 to the surrounding tissue, providing an effective seal, a local medication and/or cell delivery device, a vascularized scaffold for in vivo sensing, and a better path to tissue regeneration. The annealing process allows for on-site/on-demand gel formation (which is ideal for in vitro and in vivo applications), for example delivery through a small incision to a minimally-invasive surgical site or through injection by a needle or through a catheter or cannula. The scaffold 12 may comprise of homogeneous or heterogeneous populations of microgel particles 12. As discussed, the heterogeneous populations of microgel particles 12 may vary in physical (e.g., in size, shape, or stiffness) or vary in chemical composition (e.g., varied ratios of degradable linkers, or L- or D-amino acids to modify degradation rate, varied annealing moieties, cell adhesive moieties, or loading of microgels 12 with bioactive molecules or nanoparticles). The heterogeneous composition of the final annealed scaffold 10 can be random or structured in layers of uniform composition to create gradients in micro-porous structures (by varying microgel particle 12 sizes in layers, for example) or gradients of chemical composition (by layers of microgel particles 12 with different composition or bio-active molecule loading). Gradients may be useful in directing cell ingrowth and tissue regeneration in vivo, or development of tissue structures in vitro. Gradients in microgel particle 12 composition could be achieved by delivering sequential slurries of a gel of a single composition, followed by annealing, and then subsequent delivery of the next gel of a second composition, followed by annealing which links the new layer of microgels to the previous layer, until a desired number of layers have been accumulated. The thickness of each layer can be controlled using the volume of slurry injected and area of the injection site. An alternative embodiment to achieve gradients is to load a multi-barrel syringe applicator such as that illustrated in FIG. 6A with different microgel compositions in each of the barrels. Each of the barrels are simultaneously compressed and feed to the nozzle 120 in layered sheets. The nozzle 120 itself of the syringe applicator can be non-circular or rectangular to create a layered slurry of multiple composition that is injected to a site in a ribbon-like structure, which can then be annealed in this arrangement. Formation of the structurally contiguous annealed scaffold 10 may be achieved through radical, enzymatic or chemical (e.g., Click chemistry) processes.

In one or more embodiments, annealing occurs through surface chemistry interactions between microgel particles 12 once they are ready to be placed at the delivery site. In one embodiment, the process occurs through radical-initiated annealing via surface polymerizable groups (e.g., radical initiation by photo-sensitive radical initiators, etc.). In another embodiment, the process occurs through enzymatic chemistry via surface presented enzymatically-active substrates (e.g., transglutaminase enzymes like Factor XIIIa). In another embodiment, the process occurs through covalent coupling via Michael and pseudo-Michael addition reactions. This method can use multiple microgel particle population types that when mixed form a solid scaffold 10 (e.g., microgel particle 12 type A presenting, for example, nucleophilic surface groups and microgel particle 12 type B presenting, for example, $\alpha,\beta$-unsaturated carbonyl groups). In another embodiment, the process occurs through Click chemistry attachment. Similarly, this method can use heterogeneous microgel particle 12 populations that when mixed form a solid microporous gel. In another embodiment, annealing may be achieved using light (for example, either white light or UV light) to initiate a chemical reaction between molecules on the gel surfaces, mediated by a light activated molecule in solution in and around (or directly covalently liked to) the microgels as described herein.

In one preferred embodiment, the microgel particles 12 include a PEG based polymeric backbone in combination with an enzymatically degradable crosslinker to allow for bioresorbability. In certain embodiments, the PEG-based polymeric backbone is a 4-arm poly(ethylene glycol) vinyl sulfone (PEG-VS) backbone pre-modified with oligopeptides for cell adhesive properties (e.g., RGD) and surface annealing functionalities (e.g., K and Q peptides) and the cross-linker is a matrix metalloprotease (MMP)-degradable cross-linker.

In one or more embodiments, microgel particles 12 are formed by a water-in-oil emulsion. Gelation of the microgel particles 12 occurs upon combination of PEG solution with cross-linker solution (followed shortly by partitioning into microgel droplets before completion of gelation). A variety of substrates, including peptide ligands, can be further added for enhanced bioactivity. In one embodiment, scaffold formation is accomplished by addition and activation of radical photo-initiator to the purified microgel particles 12 to induce chemical cross-linking. In another embodiment, scaffold formation is accomplished by the use and/or activation of an endogenously present or exogenously applied transglutaminase enzyme, Factor XIII, to the purified microgel particles 12 that have been modified with two peptide ligands either pre-formation, during formation, or post-formation to induce enzymatic cross-linking. In a separate embodiment, scaffold formation is accomplished using a combination of the aforementioned radical and enzymatic methods.

The resultant scaffold 10 of the presently disclosed subject matter provides advantages over current porous scaffold technologies due to the ability to form a fully interconnected microporous scaffold in vivo. In general, porous scaffolds provide for greater access for live cells due to the freedom of movement through the pores (i.e., not requiring degradation to allow penetration like all current and previous non-porous and nano-porous scaffolds). For example when implanting and annealing a scaffold 10 in a skin wound in vivo, significantly enhanced cell invasion and tissue-structure in growth was observed after 5 days when compared to a non-porous gel of the same material as seen in FIG. 7B. FIG. 7A illustrates H&E staining of tissue sections in SKH1-Hr$^{hr}$ mice for tissue injected with the scaffold 10 (identified as MAP scaffold) as well as the non-porous control 24 hours after injection. FIG. 7B illustrates a graph of wound closure (%) as a function of days post-injection.

Figure 7C:
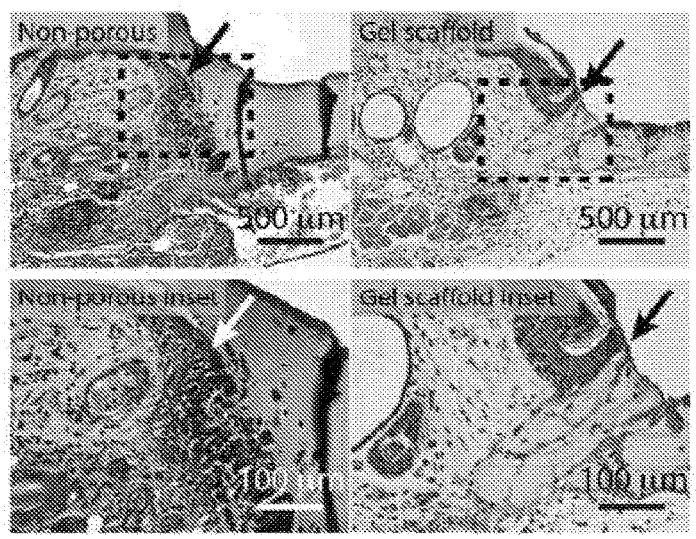
FIG. 7C illustrate representative images of wound closure during a 5-day in vivo wound healing model in SKH1-Hr$^{hr}$ mice comparing the gel scaffold (left panels) to a non-porous PEG gel control (right panels).
Figure 7C:
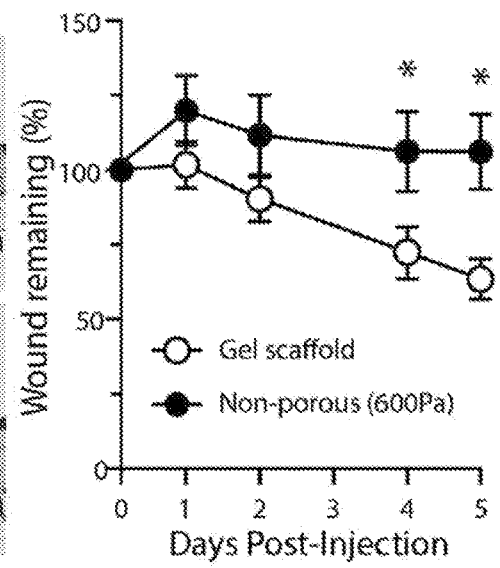
Figure 7C:
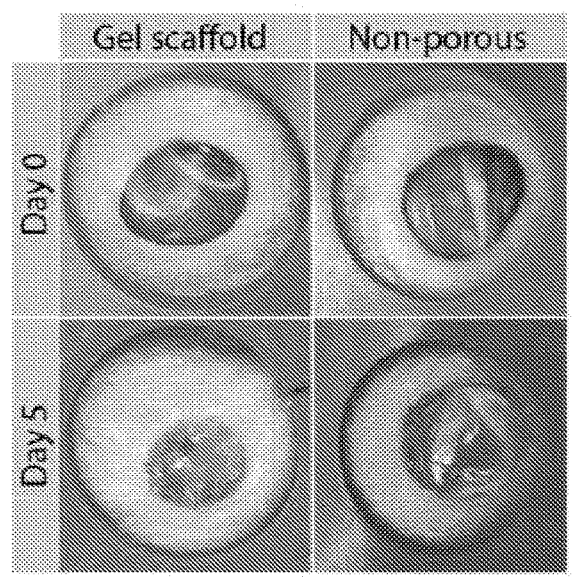
Figure 7D:
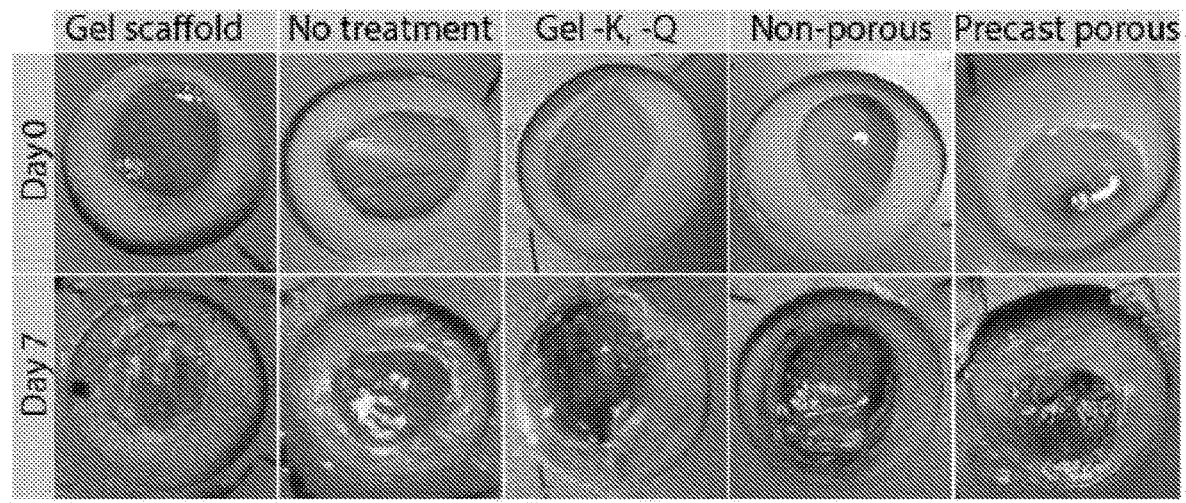
FIG. 7D illustrates representative images of wound closure during 7-day in vivo BALB/c experiments. After 7 days in vivo, the scaffolds promote significantly faster wound healing than the no treatment control, the gels lacking the K and Q peptides, the non-porous PEG gel, and faster wound healing than the precast porous gel. Porous gels created ex vivo to precisely match the wound shape using the canonical, porogen-based, casting method showed appreciable wound healing rates, comparable to the scaffolds, but lacking injectability (N≥5).
Figure 7E:
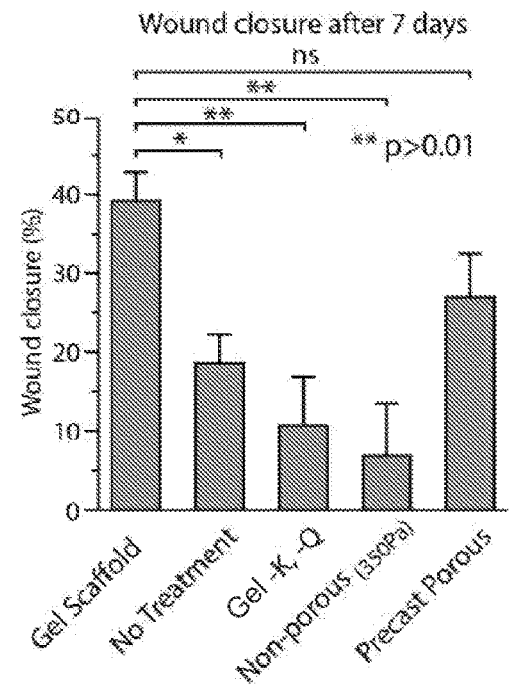
FIG. 7E is a bar graph illustrating wound closure quantification data from BALB/c in vivo wound healing for each treatment category corresponding to FIG. 7D. All data are presented as average +/−SEM. Statistical significance performed using standard two-tailed t-test (*: $p<0.05$; **$p<0.01$).
Figure 7F:
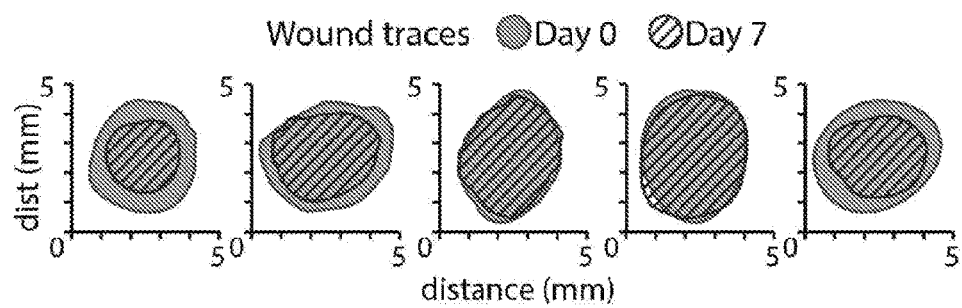
FIG. 7F illustrates traces of wound bed closure during 7 days in vivo for each treatment category corresponding to FIG. 7D and FIG. 7E.

This graphs shows that over a five (5) day period there is statistically significant improvement in the wound closure rates for using the scaffolds 10 when compared to non-porous bi-lateral controls (N=5). FIG. 7C illustrate representative images of wound closure during a 5 day in vivo wound healing model in SKH1-Hr$^{hr}$ mice. FIG. 7D illustrates representative images of wound closure during 7 day in vivo BALB/c mice experiments. FIG. 7E illustrates wound closure quantification data from BALB/c in vivo wound healing. After 7 days in vivo, the scaffolds 10 promote significantly faster wound healing than the no treatment control, the non-porous PEG gel, and the gels lacking the K and Q peptides. Porous gels created ex vivo to precisely match the wound shape using the canonical, porogen-based, casting method showed appreciable wound healing rates, comparable to the scaffolds 10, but lacking injectability (N≥5). FIG. 7F illustrates traces of wound bed closure during 7 days in vivo for each treatment category corresponding to FIG. 7D.

Figure 7G:
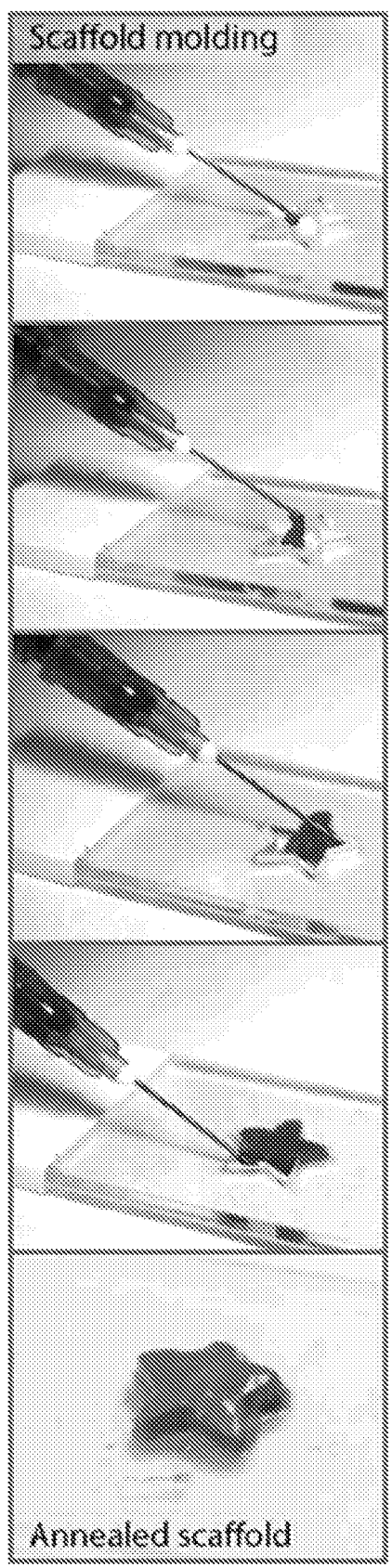
FIG. 7G illustrates how the microgel particle-containing solution or slurry can be injected using a syringe device (e.g., 25 Gauge syringe) like that of FIG. 6A or 6B into a treatment site where the microgel conforms to the shape of the injection site (e.g., in this case a star-shaped laser cut acrylic mold) and subsequent annealing of the scaffold into the star shape.
Figure 7G:
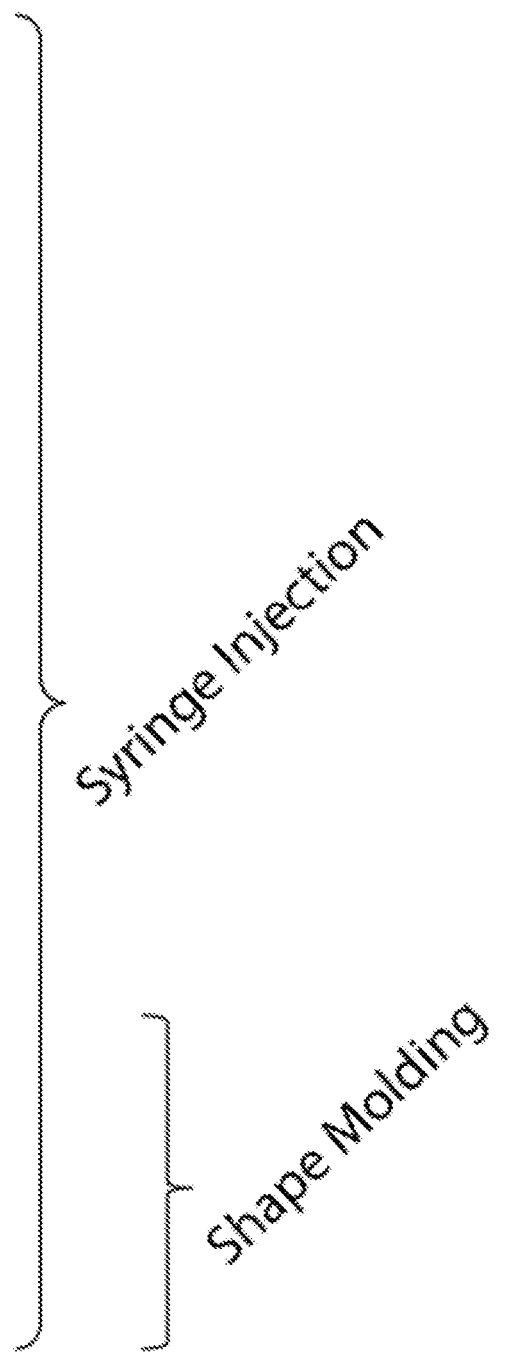

Furthermore, therapeutic agents applied to the microgel particles 12 or the scaffold 10 can be released slowly or rapidly, and the scaffold 10 has the ability to break down over a pre-determined period of time either from hydrolysis, proteolysis, or enzymolysis, depending on the intended treatment (e.g., if it is being used to treat a chronic wound, a more stable cross-linker that degrades slowly over time is used). Additionally, the annealing quality of the microgel scaffold 10 allows the scaffold 10 to function as a tissue sealant (e.g., acute wounds, surgical closure, etc.), and the filling of different molded shapes that are clinically useful to mimic tissues. FIG. 7G illustrates how the microgel particle containing solution or slurry can be applied using a syringe device like that of FIG. 6A or 6B into a treatment site where the microgel conforms to the shape of the injection site (e.g., in this case a star-shaped site) and subsequent annealing of the scaffold 10 into the star shape.

By adjusting the rate of degradation of the microgel scaffolds 10 the scar forming or regenerative response in a wound can be modified. In one embodiment, the degradation rate of the microgel scaffolds 10 was modified by using D- instead of L-amino acids in the MMP-degradable crosslinker. Adjusting the ratio of microgel particles 12 with D- or L-chirality in the crosslinker adjusted the rate of degradation in the tissue. Scaffolds 10 made from mixtures of D and L crosslinked microgels (at a 1:1 ratio) resulted in gels present in the tissue 21 days after injection, however in the D-only gels, there was no remaining gel left after 21 days in vivo. Tissue healing and scarring response also depends on the stoichiometry of D:L, and thus the degradation rate. FIGS. 8A-8G show the effects of scar reduction when using a 1:1 mixture of D:L, as compared directly to a no treatment wound. Dermal thickness is doubled and scar size is reduced by 25% in the 1:1 D:L gel treatment. Additionally, six (6) times more hair follicles and sweat glands are present in the gel-treated case, compared to the no treatment case.

Experimental

A microfluidic water-in-oil emulsion approach was used to segment a continuous pre-gel aqueous phase into uniform scaffold building blocks as described herein. Generating microgel particles 12 as building blocks serially at the microscale, rather than using the typical vortex and sonication-based approaches allowed tight control over the formation environment and ultimate material properties of the emergent scaffold 10. By tuning the flow rates of both the pre-gel solution and the pinching oil flow, as well as the geometry of the microfluidic channel, a range of microgel particle sizes were created with low polydispersity. Although the fabrication method was serial, it retained practicality in its high throughput nature, with generation rates that ranged from 250 Hz for larger particles (>100 µm) to ~1200 Hz for small particles (~15 µm). This translated to roughly 100 µl of pre-swollen gel every 50 min for a single device. This approach ultimately resulted in particles that were highly monodisperse, both physically and chemically. Microfluidic generation of microgel particle "building blocks" is a readily scalable process: a practical requirement for wide adoption and use.

The resultant microgel particles 12 were composed of a completely synthetic hydrogel mesh of poly(ethylene)glycol-vinyl sulfone (PEG-VS) backbones decorated with cell-adhesive peptide (RGD [SEQ ID NO: 3]) and two transglutaminase peptide substrates (K [SEQ ID NO: 1] and Q [SEQ ID NO: 2]). The microgel particles 12 were crosslinked via Michael type addition with cysteine-terminated matrix metalloprotease-sensitive peptide sequences that allowed for cell-controlled material degradation and subsequent resorption.

Figure 9A:
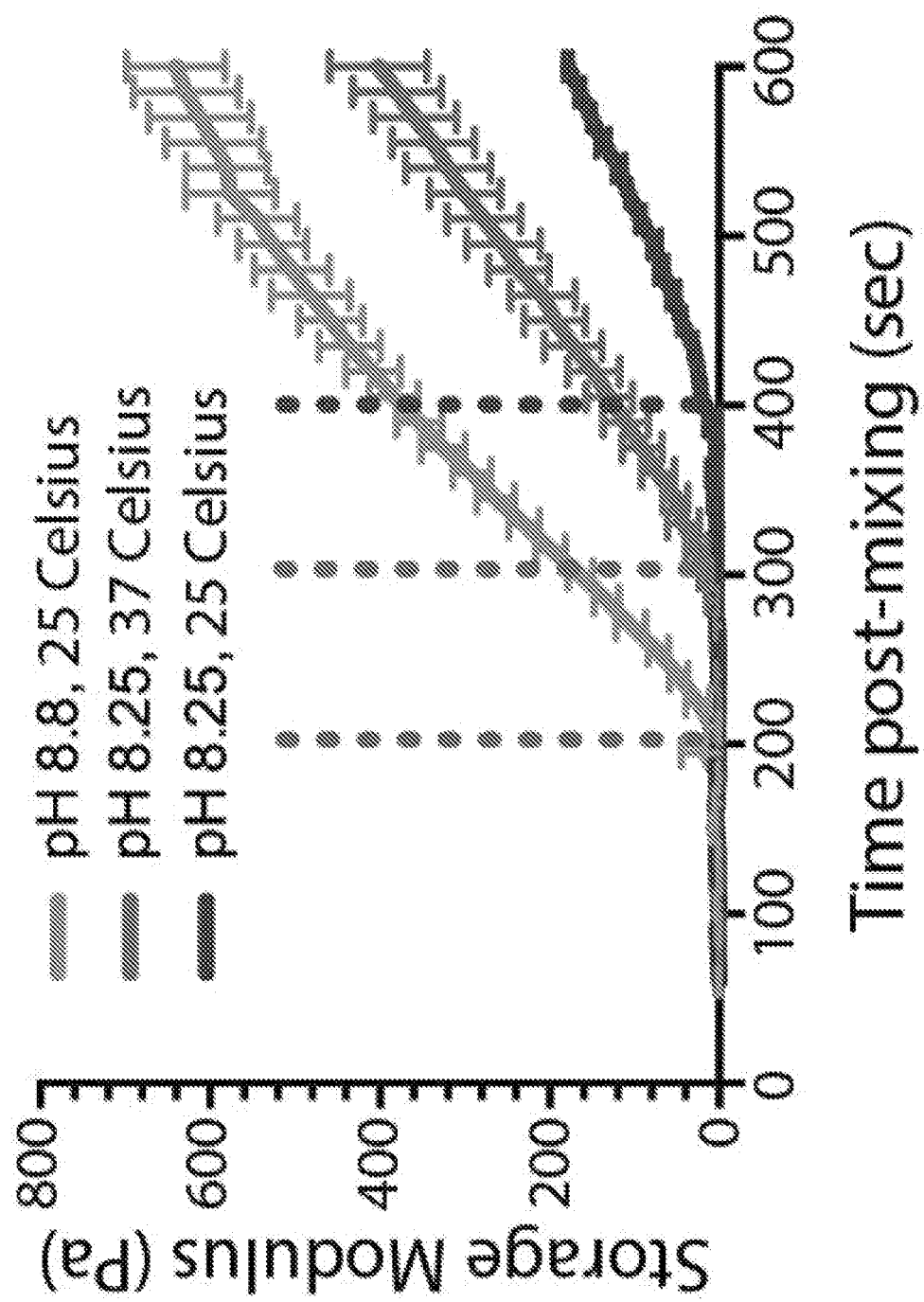
FIG. 9A illustrates a graph of storage modulus as a function of time post-mixing for different gelation kinetics (pH and temperature). pH 8.25 at 25 degrees Celsius is represented by the bottom line in the graph; pH 8.8 at 25 degrees Celsius is represented by the top line in the graph; and pH 8.25 at 37 degrees Celsius is represented by the middle line in the graph.

The microgel particles 12 were purified into an aqueous solution of isotonic cell culture media for storage and when used to form a gel were annealed to one another via a non-canonical amide linkage between the K and Q peptides mediated by activated Factor XIII (FXIIIa), a naturally occurring enzyme responsible for stabilizing blood clots. This enzyme-mediated annealing process, allowed incorporation of living cells into a dynamically forming scaffold 10 that contained interconnected microporous networks. Following addition of FXIIIa, but prior to scaffold annealing, a slurry of the microgel particles 12 can be delivered via syringe application, ultimately solidifying in the shape of the cavity in which they are injected. FIG. 9A illustrates how the annealing kinetics can be altered by the adjustment of pH and temperature. The annealing environment chosen for this experiment was pH 8.25 and a temperature of 37° C.

Figure 9B:
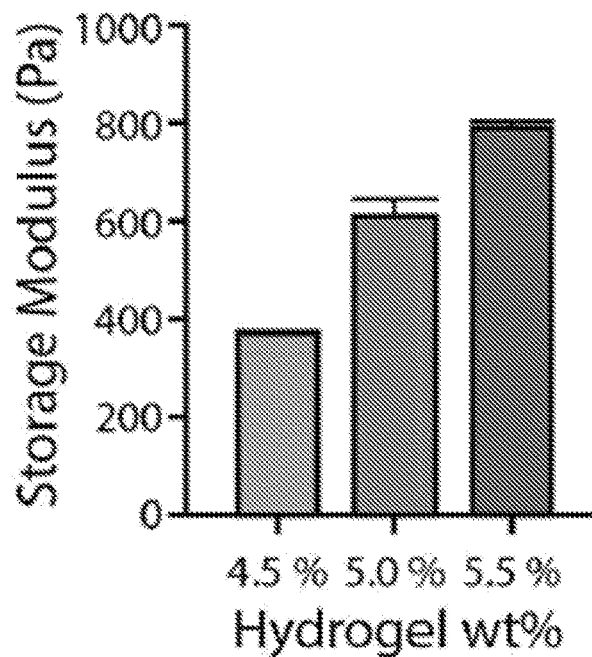
FIG. 9B illustrates different hydrogel weight percentages were used to produce different stiffness materials on the x-axis. The graph illustrated Storage Modulus (Pa) for various hydrogel weight percentages.
Figure 9C:
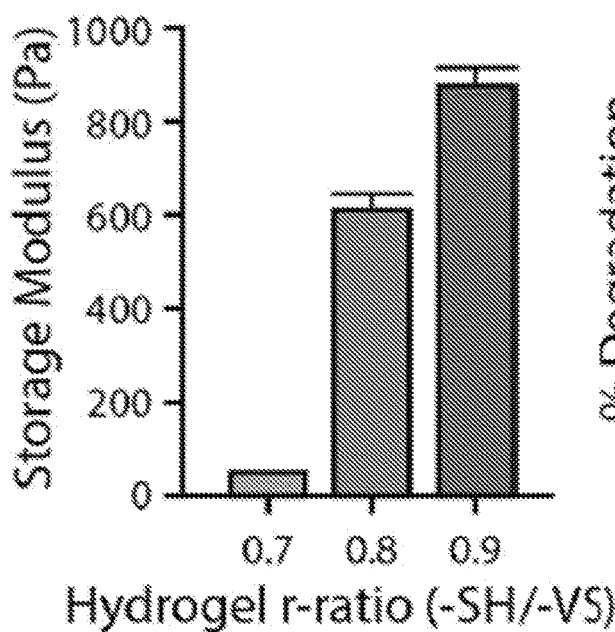
FIG. 9C illustrates different crosslinker stoichiometries that were used to produce different stiffness values in the resultant gel on the x-axis. The graph illustrated Storage Modulus (Pa) as a function of the r-ratio of free crosslinker ends (—SH) to vinyl groups (—VS) on the PEG molecule.
Figure 9D:
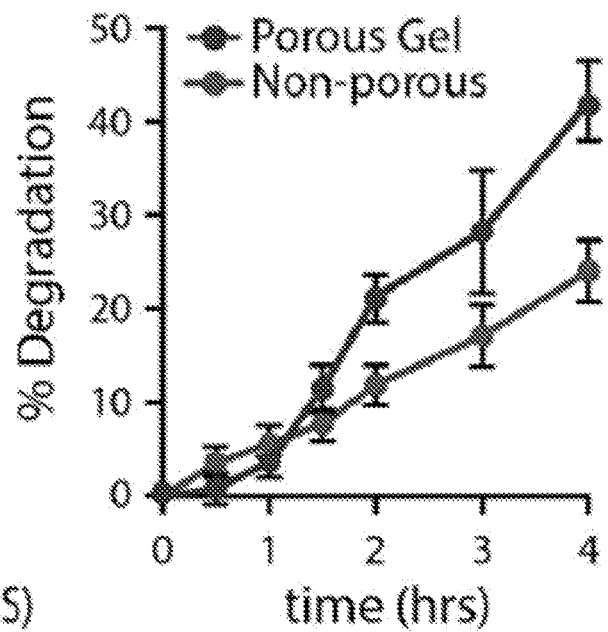
FIG. 9D illustrates a graph of the % degradation as a function of time for both the non-porous control (bottom line of the graph) as well as a porous gel described herein (top line of the graph).
Figure 9E:
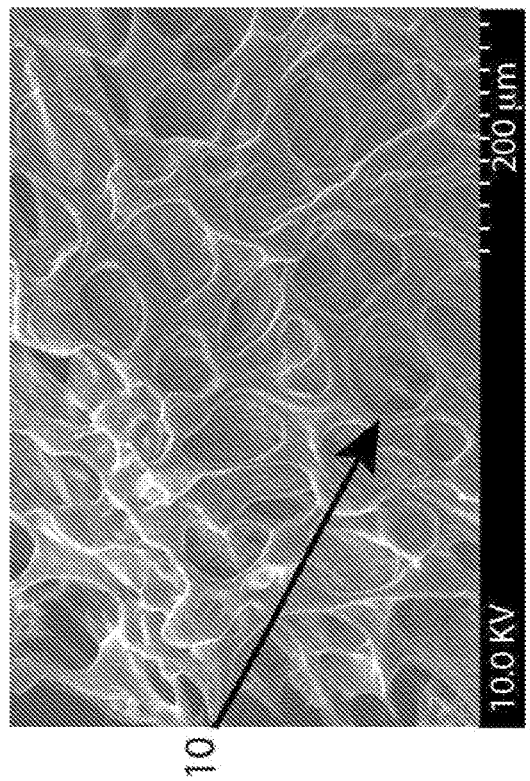
FIG. 9E illustrates SEM images of a scaffold annealed with FXIIIa at 200 μm (top panel) or 100 μm (bottom panel).
Figure 9E:
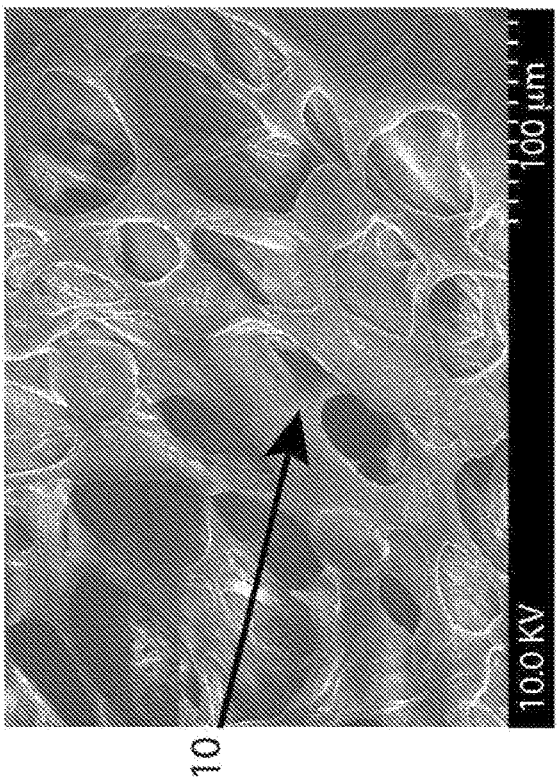

Structural changes leading to over a three-fold increase in storage modulus in the annealed gels was observed upon addition of FXIIIa to the microgel particles 12. Annealing was confirmed as being necessary for scaffold formation via high-vacuum SEM observation, wherein upon dehydration the scaffolds adopted a highly stretched but interconnected mesh whereas building blocks without FXIIIa separated into individual spherical beads (FIG. 9E).

Figure 9F:
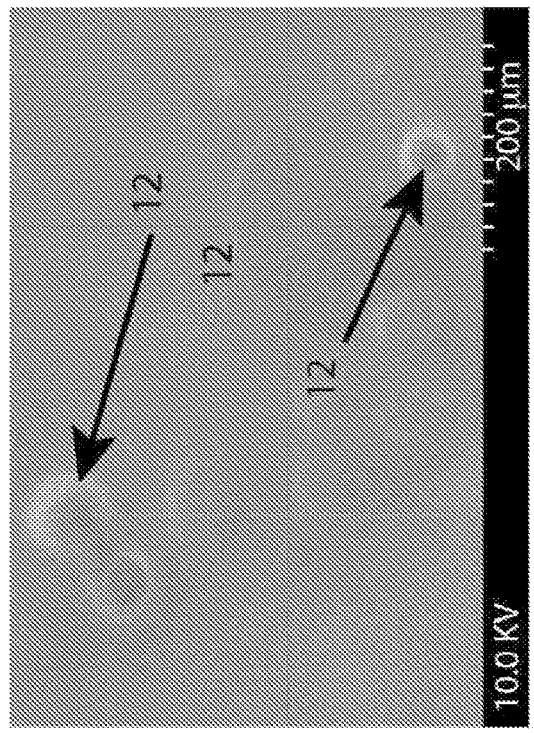
FIG. 9F illustrates SEM images of microgel particles without FXIIIa at 200 μm (top panel) or 100 μm (bottom panel). Un-annealed microgel particles are seen in FIG. 9F.
Figure 9F:
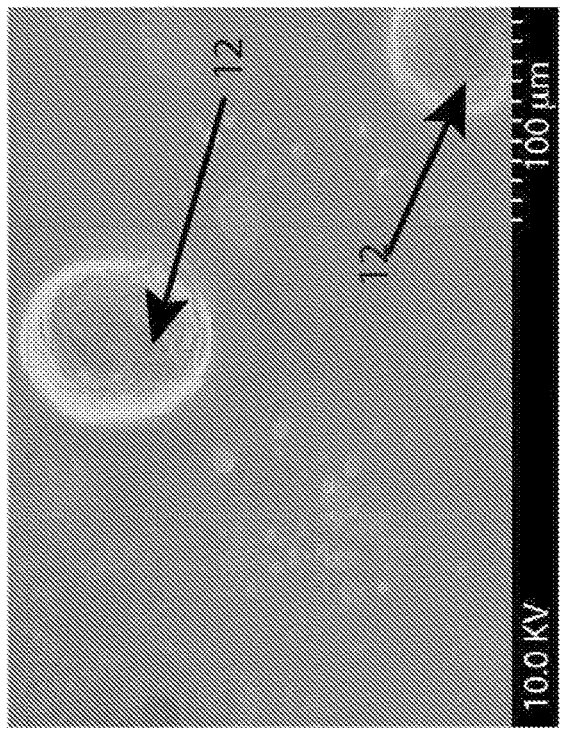

By tuning the microgel particle size and composition a diverse set of assembled scaffolds 10 were able to be generated. By using microgel particles 12 from 30 to 150 µm in diameter, networks with median pores diameters ranging from ~10 to ~35 µm were achieved). Different PEG weight percentages and crosslinker stoichiometries were screened to demonstrate a range of easily achievable storage moduli from ~10 to 1000 Pa that spans the stiffness regime necessary for mammalian soft tissue mimetics. FIG. 9B illustrates different hydrogel weight percentages were used to produce different stiffness materials. FIG. 9C illustrates different crosslinker stoichiometries (r-ratio of crosslinker ends (—SH) to vinyl groups (—VS)) that were used to produce different stiffness values in the resultant gel. FIG. 9D illustrates a graph of the % degradation as a function of time for both the non-porous control as well as the inventive porous gel described herein. Degradation kinetics of particle-based, porous gel and the non-porous are shown for equal volumes of gels in vitro. The particle-based, porous gels degrade faster than non-porous gel due to higher surface area to volume ratios and faster transport through the microporous gel. Degradation was carried out using 1:1000 TrypLE®, resulting in higher protease concentrations than in a wound bed and faster degradation kinetics. FIG. 9E illustrates SEM images of a scaffold annealed with FXIIIa. FIG. 9F illustrates SEM images of microgel particles 12 without FXIIIa. Un-annealed particles are seen in FIG. 9F.

In order to assess the ability of the generated scaffold to support cell growth and network formation, an in vitro cell morphology and proliferation model using three human cell lines was developed. These included: Dermal Fibroblasts (HDF), Adipose-derived Mesenchymal Stem Cells (AhMSC), and Bone Marrow-derived Mesenchymal Stem Cells (BMhMSC). A single-cell suspension was dynamically incorporated within a FXIIIa annealed gel. The three cell lines exhibited high cell viability 93%) following twenty-four (24) hours of culture within the scaffold. The HDF and AhMSC cell lines demonstrated continued proliferation over a six-day culture period with doubling times of 1.5 and 2 days, respectively. BMhMSCs were observed to undergo proliferation as well, however with an extended calculated doubling time of ~12 days.

Cells incorporated into the scaffold began to exhibit spread morphology 90 minutes following the onset of annealing. After two (2) days in culture, all observed cells within the scaffolds exhibited a completely spread morphology, which continued through day six (6). Importantly, an extensive network formation for all cell lines was observed by day two (2). Cell networks increased in size and complexity through the entirety of the experiment. The BMhMSCs were of particular note, as their expansive network formation and slower proliferation rate indicated that these cells were able to spread to extreme lengths, forming highly interconnected cellular networks within the microporous scaffolds. Notably, cells that were grown in non-porous gels of identical chemical properties (5 wt %, G'=600 Pa gel) and mechanical properties (4.5 wt %, G'=350 Pa gel) maintained viability but did not exhibit any appreciable network formation, even after six days in culture.

It was hypothesized that the ability of the scaffolds to enable both cell proliferation and expedient network formation in vitro was indicative of an ability to support in vivo cell migration and bulk tissue integration within the scaffold. To test this hypothesis, a murine skin wound healing model was used, addressing a tissue of interest for previous implanted porous biomaterials. Importantly, wound contraction was prevented using a sutured rubber splint that limited closure to tissue ingrowth, better simulating the human healing response. Because of the injectability of the microgel particle-based scaffold, the microgel particles were able to be directly delivered to the wound site, followed by in situ annealing via exogenous FXIIIa. This provided a seamless interface by simultaneously linking the microgel particle "building blocks" to one another as well as to endogenous lysine and glutamine residues present in the surrounding tissue. Similarly, a seamless interface was observed for the chemically identical, nonporous bi-lateral control. Despite their similar interface, the generated scaffold resulted in significantly faster wound closure than the non-porous controls (60% versus 100% remaining wound area after 5 days, respectively) when injected into the wounds of CLR:SKH1-Hr$^{hr}$ mice as seen in FIG. 7B.

The disparities in wound closure rates led to the investigation of the differences in tissue responses to the non-porous and injectable partible-based gel. The scaffold injection using the microgel particles resulted in extensive wound re-epithelialization after five (5) days in vivo. keratin-5$^+$ cells were observed with stratified squamous morphology over the apical surface of the scaffold, however no cells (keratin-5$^+$ or otherwise) were observed past the non-porous wound edge. Importantly, the scaffold was able to sustain the formation of what appeared to be a complete hair follicle with adjoining sebaceous gland within the wound bed resembling the structure of these glands in the uninjured skin. Further, other instances of large Keratin-5$^+$ tissue structures were observed within the scaffold including tubular structures and epithelial invaginations. It is hypothesized that together, these results are an indication of higher order collective migration (i.e., movement of multicellular clusters in concert) contributing to epidermal regeneration. Although cells were able to infiltrate the non-porous bi-lateral controls (as indicated by DAPI staining), no evidence of re-epithelialization or cutaneous tissue formation was found after five (5) days in vivo.

Through further investigation, it was found that the scaffold promoted bulk integration via complex vascular network formation in vivo. After five (5) days, both endothelial cells and supporting pericytes were present within the scaffold, while only single branches of endothelial cells without supporting pericytes were present in the non-porous bilateral controls. The presence of co-localized endothelial cells and pericytes was evidence of mature vessel network formation. To our knowledge, this is the first instance of early (<7 days) pericyte migration into a synthetic injectable material or implanted porous scaffold without the inclusion of exogenous growth factors.

While investigating the seamless interface provided by the injectable scaffolds differences were observed in both overall and immune cell quantities at day one (1). After one (1) day post-injection, the scaffolds contained significantly higher numbers of cells within the scaffold than their non-porous bi-lateral controls. This corroborated the greater ease of cell mobility previously observed in our in vitro network formation experiments. Further, the scaffold and its surrounding tissue contained a significantly lower number of polymorphonuclear cells when compared to the non-porous bi-lateral control of the same mouse. This result indicated an overall lower initial innate immune response to the scaffolds at day one (1). After five (5) days post-injection, lower fractions of CD11b$^+$ cells (activated leukocytes) were present both in the surrounding tissue and within the scaffold relative to the non-porous controls, indicating a sustained lower level of inflammatory immune response, in agreement with what has been observed in ex vivo constructed and implanted micro-porous scaffolds. Combined, these two results support a presently underexplored geometric component to immune stimulation from chemically-identical injectable biomaterials.

The annealed, microgel particle-based scaffolds represent a new class of injectable biomaterial that introduces microscale interconnected porosity through robustly achieved imperfect self-assembly and annealing of individual building blocks. This approach allows control of micro-scale and hierarchical macro-scale properties through deterministic chemical composition and microfluidic particle generation. Both incorporated live cells and surrounding host tissue are able to immediately infiltrate the scaffold without the need for material degradation, a feat never before accomplished using injectable scaffolds.

In vivo, the injectable microgel particles completely filled the tissue void, providing a seamless boundary with the surrounding tissue. The interconnected microporosity of the resulting scaffold promoted cellular migration at the wound site that resulted in greater bulk integration with the surrounding tissue while eliciting a reduced host immune response, in comparison to an injectable non-porous control. Ultimately this led to faster healthy tissue reformation than with similarly comprised injectable non-porous gels.

This gel system presents a fundamental change in the approach to bottom-up modular biomaterials by utilizing the negative space of lattice formation to promote the development of complex three-dimensional networks on time scales previously unseen using current hydrogel technologies. The "plug and play" nature of this strategy allows the incorporation of a wide range of already established materials (e.g., fibrin), signals (e.g., growth factors), and cell populations (e.g., stem cells). Complex combinations of building blocks with deterministic chemical and physical properties may enable tissue regeneration in a range of distinct physiological niches (e.g., neural, cardiac, skin, etc.), where particle-annealed scaffolds are tailored to each niche via their building block properties. The unique combination of microporosity, injectability, and modular assembly inherent to scaffolds has the potential to alter the landscape of tissue regeneration in vivo and tissue creation de novo.

Microfluidic water-in-oil droplet generators were fabricated using soft lithography as previously described. Briefly, master molds were fabricated on mechanical grade silicon wafers (University wafer) using KMPR 1025 or 1050 photoresist (Microchem). Varying channel heights were obtained by spinning photoresist at different speeds, per the manufacturer's suggestions. Devices were molded from the masters using poly(dimethyl)siloxane (PDMS) SYLGARD® 184 kit (Dow Corning). The base and crosslinker were mixed at a 10:1 mass ratio, poured over the mold, and degassed prior to curing for 6 hours at 65° C. Channels were sealed by treating the PDMS mold and a glass microscope slide (VWR) with oxygen plasma at 500 mTorr and 75 W for 15 seconds. Immediately after channel sealing, the channels were functionalized by injecting 100 µl of a solution of RAIN-X® and reacting for 20 minutes at room temperature. The channels were then dried by air followed by desiccation overnight.

Droplets were generated using a microfluidic water-in-oil segmentation system as illustrated in FIGS. 3A-3F and 4A-4C. The aqueous phase is a 1:1 volume mixture of two parts: (i) a 10% w/v 4 arm PEG-VS (20 kDa) in 300 mM triethanolamine (Sigma), pH 8.25, prefunctionalized with 500 µM K-peptide (Ac-FKGGERCG-NH$_2$ [SEQ ID NO: 1]) (Genscript), 500 µM Q-peptide (Ac-NQEQVSPLGGERCG-NH$_2$ [SEQ ID NO: 2]), and 1 mM RGD (Ac-RGD-SPGERCG-NH$_2$ [SEQ ID NO: 3]) (Genscript) and (ii) an 8 mM (12 mM for the three-inlet device) di-cysteine modified Matrix Metallo-protease (MMP) (Ac-GCRDGPQGIWGQDRCG-NH$_2$ [SEQ ID NO: 4]) (Genscript) substrate pre-reacted with 10 µM Alexa-fluor 647-maleimide (Life Technologies). All solutions were sterile-filtered through a 0.2 µm Polyethersulfone (PES) membrane in a Leur-Lok syringe filter prior to use in the segmentation system.

Generation was performed at 37° C. on an incubated microscope stage (NIKON® Eclipse Ti) for real time monitoring of microgel quality. The input aqueous solutions did not appreciably mix until droplet segmentation (Peclet number >10). The oil phase was a heavy mineral (Fisher) oil supplemented with 0.25% v/v SPAN® 80 (Sigma-Aldrich). Downstream of the segmentation region, a second oil inlet with a high concentration of SPAN® 80 (5% v/v) was added and mixed to the flowing droplet emulsion. Ultimately, the microgel-in-oil mixture exited into a large (12 mm diameter, ~1 mL volume) well, where the microgel particles cured at 37° C. for a minimum of 1 hour. The mixture was then extracted and purified by overlaying the oil solution onto an aqueous buffer of HEPES buffered saline pH 7.4 and pelleting in a table top centrifuge at 18000× g for 5 mins. The microgel-based pellet was washed in HEPES buffered saline pH 7.4 with 10 mM CaCl$_2$ and 0.01% w/v Pluronic F-127 (Sigma). The microgel aqueous solution was then allowed to swell and equilibrate with buffer for at least 2 hours at 37° C.

To determine the operational regime of droplet segmentation, device operation was monitored in real time using a high-speed camera (Phantom), followed by image analysis for size and polydispersity measurement (using ImageJ software) as well as segmentation frequency (Phantom PC2). For stable droplet segmentation on this platform: (i) initiate all flows simultaneously (both aqueous flows and both oil flows) at 5 µl/min until all air has been flushed from the device, (ii) turn down aqueous flow rates to the desired overall volumetric rate (aqueous flow rate between 1.5 and 2 µL/minute and oil flow rates between 1 and 5 µL/minute for 5 minutes, (iii) aspirate all accumulated liquid from collection well to ensure collection of monodisperse µgels, and (iv) run generation.

Fully swollen and equilibrated "building block" microgel particles were pelleted by centrifugation at 18000× g for five minutes, and the excess buffer (HEPES pH 7.4+10 mM CaCl$_2$) was removed by aspiration and drying with a cleanroom wipe. Subsequently, microgel particles were split into aliquots, each containing 50 µl of concentrated building blocks. An equal volume of HEPES pH 7.4+10 mM CaCl$_2$ was added to the concentrated building block solutions. Half of these include Thrombin (Sigma) to a final concentration of 2 U/ml and the other half includes FXIII (CSL Behring) to a final concentration of 10 U/ml. These solutions were then well mixed and spun down at 18000× g, followed by removal of excess liquid with a cleanroom wipe (American Cleanstat).

Annealing was initiated by mixing equal volumes of the building block solutions containing Thrombin and FXIII using a positive displacement pipet (Gilson). These solutions were well mixed by pipetting up and down, repeatedly, in conjunction with stirring using the pipet tip. The mixed solution was then pipetted into the desired location (mold, well plate, mouse wound, etc.).

To determine the gelation kinetics for each microgel, a macroscale (50 µL) non-porous gel was generated with the same chemical composition. A 30 µL solution of 2×PEG-VS+peptides (RGD, K, and Q peptides) dissolved in 0.3 M TEOA was combined with 30 µL of 2×MMP-1 crosslinker dissolved in water. The mixture was quickly vortexed and 50 µL of the mixture was placed between two 8 mm rheological discs at a spacing of 1 mm (Anton Paar Physica MCR301 Rheometer). The storage modulus was then measured over a period of 20 minutes (2.5 Hz, 0.1% strain).

To determine the bulk storage modulus of the pre-annealed microgel particles and post-annealed scaffold an amplitude sweep (0.01-10% strain) was performed to find the linear amplitude range for each. An amplitude within the linear range was chosen to run a frequency sweep (0.5-5 Hz). For pre-annealed microgel particles, 50 µL of microgel particles (5 wt % PEG-VS 4-arm MW=20 KDa, r=0.8 MMP-1 crosslinker, with synthetic peptide concentrations of 250 µM synthetic K, 250 µM synthetic Q, 500 µM synthetic RGD) was injected between two 8 mm rheological discs at a spacing of 1 mm. For post-annealed scaffold measurement, we first pipetted 50 µL of microgel particles (N=3) (5 wt % PEG-VS 4-arm MW=20 KDa, r=0.8 MMP-1 crosslinker, with synthetic peptide concentrations of 250 µM synthetic K, 250 µM synthetic Q, 500 µM synthetic RGD) spiked with FXIIIa, 5 U/mL final concentration, and thrombin, 1 U/mL final concentration, between two glass slides. This mixture was allowed to partially anneal for 10 minutes before removal of top glass slide and placement in a humidified incubator at 37° C. for 90 minutes. The scaffolds were then placed into HEPES buffered saline (pH 7.4) overnight to reach equilibrium. The samples were then placed between two 8 mm discs on the rheometer and tested identically to the pre-annealed microgel particles.

To determine median pore size in the annealed microgel scaffolds, stock solutions of different sized microgel particles were used to anneal three separate scaffolds from each (9 scaffolds in total), as described above. Using a Nikon Ti eclipse equipped with the C2 laser LED confocal, individual slices were taken in each gel, separated by 50 µm between each slice (10 slices per gel, with 30 total slices for each gel type). These images were then analyzed using a custom script written in MATLAB®, to identify the pore regions and calculate each one's size in $px^2$. Each individual pore's size was then used to calculate the median pore size for that gel, and converted to $\mu m^2$ using the pixel to µm conversion from the original microscope image (0.31 µm/px). These areas were then converted to a characteristic length measurement by forcing the areas to a circle, and calculating the characteristic diameter of these circles. For 30 µm microgel particles, mean pore diameter was around 12 µm. For 100 µm microgel particles, mean pore diameter was around 19 µm. For 150 µm microgel particles, mean pore diameter was around 37 µm. Note that the interstices or voids are continuous and not similar to the well-defined spherical open regions connected by circular pores as produced through microparticle leaching or inverse opal gel fabrication methods, however, referring to a pore diameter is useful to simply describe the length scale of the void spaces.

To determine if microgel particles were covalently linked after addition of FXIIIa, SEM was used to directly visualize scaffolds. Microgel particle mixtures were either treated with FXIIIa (10 U/ml) or with buffer only. Subsequently, the building block solutions were placed onto a 1×1 in silicon wafer piece, and dried in an SEM (Hitachi S4700) high vac chamber ($1 \times 10^{-3}$ mTorr). Building blocks with or without FXIIIa were then visualized using 10 kV (10 mA max) on either 200× or 500× as seen in FIGS. 9D and 9F.

HEK293T cells constitutively expressing GFP via lentiviral transfection were maintained in DMEM (Life Technologies) supplemented with 10 µg/ml puromycin. Three cell lines were used for in vitro experiments: human dermal fibroblasts (HDF, Life Technologies), bone marrow-derived human mesenchymal stem cells (BMhMSC, Life Technologies), and adipose-derived human mesenchymal stem cells (AhMSC, Life Technologies). All cell lines were maintained according to manufacturer's specifications (before and after incorporation into porous or non-porous gels). Specifically, for the MSC populations reduced-serum, basal medium (Life Technologies) was used to retain stemness.

For quantification of cell proliferation and visualizations of network formation in the porous scaffolds in vitro, particle-based scaffolds were annealed with microgel particles as described above, with the addition of cell suspensions to the building block solutions prior to annealing. For each cell line, cell suspensions were prepared at a final concentration of $25 \times 10^6$ cells/ml in respective culture media un-supplemented with serum. Subsequently, 2 µl of cell suspension was added to 50 µl of microgel particle mixture containing FXIII and combined with 50 µl of microgel particle mixture containing Thrombin (500 cells/µl of gel).

This mixture was injected into the corner of a coverslip-bottom PDMS well. The well top was covered with a second coverslip and the µgel/cell mixture was allowed to undergo annealing for 90 minutes at 37° C.

After annealing was completed, the top coverslip was removed, and the appropriate complete culture media was added to the PDMS well. For the day 0 time point, 4% PFA was added directly to the PDMS wells and allowed to fix overnight at 4° C. Other cells were grown in 5% $CO_2$ and 37° C. for the times indicated (2, 4, and 6 days), at which point they were washed once with 1×PBS and fixed with 4% PFA overnight at 4° C. HEK-293-T cells were incorporated into a star-shaped mold by mixing cells with microgel particles (as described above) and pipetting 5 µl of the mixture into the center of the mold Immediately following, microgel particles without cells were pipetted in the remainder of the mold, and annealed as described above.

Proliferation was assessed by counting the number of cell nuclei present in the particle-based scaffold constructs after 0, 2, 4, and 6 days of culture in vitro. Nuclei were stained with a 2 µg/ml DAPI solution in 1×PBS for 2 hours, followed by visualization on a Nikon C2 using the 405 nm LED laser. Specifically, each scaffold was imaged by taking 55 z slices in a 150 µm total z height and compressing every 5 slices into a maximum intensity projection (MIP) image. Nuclei in the MIPs were enumerated using a custom MATLAB® script, counting the total number of cells. For each time point, z-stack images of three separate microgel scaffolds were analyzed, where each z-stack image measured a total volume of $1270 \times 1270 \times 150$ µm$^3$ (or ~280 nL). The 90 minute counts lead to a calculation of ~525 cells/µl of gel, consistent with the experimental amount added (500 cells/µl of gel).

For visualization of cell network formation within the microgel scaffolds in vitro, the constructs were prepared, grown, and fixed as above. The scaffolds were blocked with 1% BSA in 1×PBS for 1 hour at room temperature, followed by staining for f-actin via a Rhodamine-B conjugate of phalloidin (Life Technologies) for 3 hours at room temperature. The scaffolds were then washed with 1% BSA in 1×PBS, followed by counterstaining with a 2 µg/ml DAPI solution in 1×PBS for 1 hour at room temperature. Imaging was performed as with proliferation imaging, with the exception of using a 40× magnification water immersion lens. Total heights of image stacks were 130 µm, with the total number of slices at 260 (volume captures ~15 nL).

PEG-VS scaffolds (5 wt % PEG-VS 4-arm MW=20 KDa, r=0.8 MMP-1 crosslinker, with synthetic peptide concentrations of 250 µM synthetic K [SEQ ID NO: 1], 250 µM synthetic Q [SEQ ID NO: 2], 500 µM synthetic RGD [SEQ ID NO: 3]) were used to encapsulate cells (500 cells/µL). Cell lines used were the same as in microgel scaffold experiments. Gels were formed for 20 minutes (TEOA 0.3 M, pH 8.25) before being placed into appropriate media. The gels were fixed after pre-determined time points (t=90 minutes, 2 days, 4 days, and 6 days) using PFA overnight at 4° C., washed and stored in PBS. Gels were stained as in the microgel scaffolds. All samples were stored at 4° C. in PBS with P/S when not being imaged. Imaging was performed using a NIKON® C2 confocal exactly as in the microgel scaffold in vitro experiments.

CLR:SKH1-Hrhr Mice (Charles River Laboratories) (N=6 per test) were anesthetized with isofluorane (1.5% for 10 minutes), followed by clipping of nails and injection of painkiller (buprenorphine, 60 µL per 20 g at 0.015 µg/µL). The skin was pulled taut and a 4 mm biopsy punch was used to create identical circular wounds on the back of the mouse.

The periphery of the wounds was secured using a rubber splint sewn via 7-8 stitches to the surrounding skin to prevent wound closure by contraction. Either non-porous or porous hydrogel including 10 U/ml FXIIIa was injected into wound beds, allowed to undergo gelation for 10 minutes, followed by subsequent covering of the wound by a stretchy gauze wrap to prevent animal interaction. The mice were then separated into individual cages. Pain medication was administered subcutaneously every 12 hours for the next 48 hours (for Day 1 sacrifices pain killer was administered once after surgery).

At Day 1, mice (N=6) were sacrificed via isofluorane overdosing, followed by subsequent spinal dislocation. The skin of the back was removed using surgical scissors and the wound site was isolated via a 10 mm biopsy punch. The samples were immediately fixed using 4% formaldehyde at 4° C. (overnight) followed by transfer to ethanol and embedding of the sample into a paraffin block. The blocks were then sectioned at 6 µm thickness by microtome (Leica) and underwent Hematoxylin and Eosin (H&E) staining. For quantification of cell infiltration within the hydrogels and immune response surrounding the hydrogels, a series of 3 random high power (40×) fields (HPFs) were examined for each section. Samples were analyzed for cell infiltration (>0.1 mm into the gel) by counting the total number of cells of any type within the injected hydrogels (N=5 with a sum of cells in 3 sections analyzed per wound). Greater than 95% of the cells infiltrating the gels were neutrophils. To measure immune response, the average of 3 HPFs from different sections of the wound were examined. The total number of leukocytes/HPF within 0.2 mm of the hydrogel at the wound edge was quantified and averaged for each wound type. The leukocyte count for each wound was compared to its bilateral control on the same animal and the relative difference was recorded as a fraction of each animal's overall immune response. This comparison was possible because each animal had one wound injected with the microgel scaffold and one wound with the non-porous control.

Wounds were imaged daily to follow closure of the wounds. Each wound site was imaged using high-resolution camera (NIKON® COOLPIX®). Closure fraction was determined by comparing the pixel area of the wound to the pixel area within the 10 mm center hole of the red rubber splint. Closure fractions were normalized to Day 0 for each mouse/scaffold type (FIG. 7B).

At Day 5, mice (N=6) were sacrificed and tissue collected as in day 1 mice. The samples were immediately submerged in TISSUE-TEK® Optimal Cutting Temperature (OCT) fluid and frozen into a solid block with liquid nitrogen. The blocks were then cryo-sectioned at 25 µm thickness by cryostat microtome (Leica) and kept frozen until use. The sections were then fixed with paraformaldehyde for 30 minutes at room temperature, hydrated with PBS, and kept at 4° C. until stained.

Slides containing tissue sections were either blocked with 3% normal goat serum (NGS) in 1×PBS+0.05% Tween-20 (PBST) or simultaneously blocked and permeabilized with 0.2% TRITON® X-100 in 3% NGS in 1×PBST for sections stained with anti keratin-5 only. Sections were then washed in 3% NGS in 1×PBST. Primary antibody dilutions were prepared as follows in 3% NGS in 1×PBST:
- rat anti mouse CD11b (BD Pharmingen)—1:100
- rat anti mouse PECAM-1 (BD Pharmingen)—1:100
- rabbit anti mouse NG2 (Millipore)—1:100
- rabbit anti mouse keratin 5 (Covance, Inc.)—1:250

Sections were stained with primary antibodies overnight at 4° C., and subsequently washed with 3% NGS in 1×PBST.

Secondary antibodies were all prepared in 3% NGS in 1×PBST at a dilution of 1:100. Sections were incubated in secondary antibodies for 1 hour at room temperature, and subsequently washed with 1×PBST. Sections were counter-stained with 2 µg/ml DAPI in 1×PBST for 30 mins at room temperature. Sections were mounted in Antifade Gold mounting medium.

Confocal z-stack images acquired from day 5 tissue sections from both non-porous and microgel scaffold tissue blocks were compressed into MIPs, followed by separation into individual images corresponding to each laser channel (i.e., Gel, DAPI, CD11b). The gel channel image was used to trace the edge of the gel-tissue interface using Adobe illustrator. The width of this line was expanded 75 µm both into the tissue and into the gel from the interface (150 µm in total thickness). The new edges of this line were then used to crop the original DAPI and CD11b images, to capture only the areas corresponding to +/−75 µm from the tissue gel interface. These images were then imported into ImageJ, and overlaid to merge the DAPI and CD11b channels into a single image. This image was analyzed using the cell counter plugin from ImageJ, where both the total number of nuclei was quantified, as well as the total number of CD11b+ cells. Finally, the fraction of nuclei with a corresponding CD11b+ signal were reported for both within the tissue and within the gel.

Figure 11:
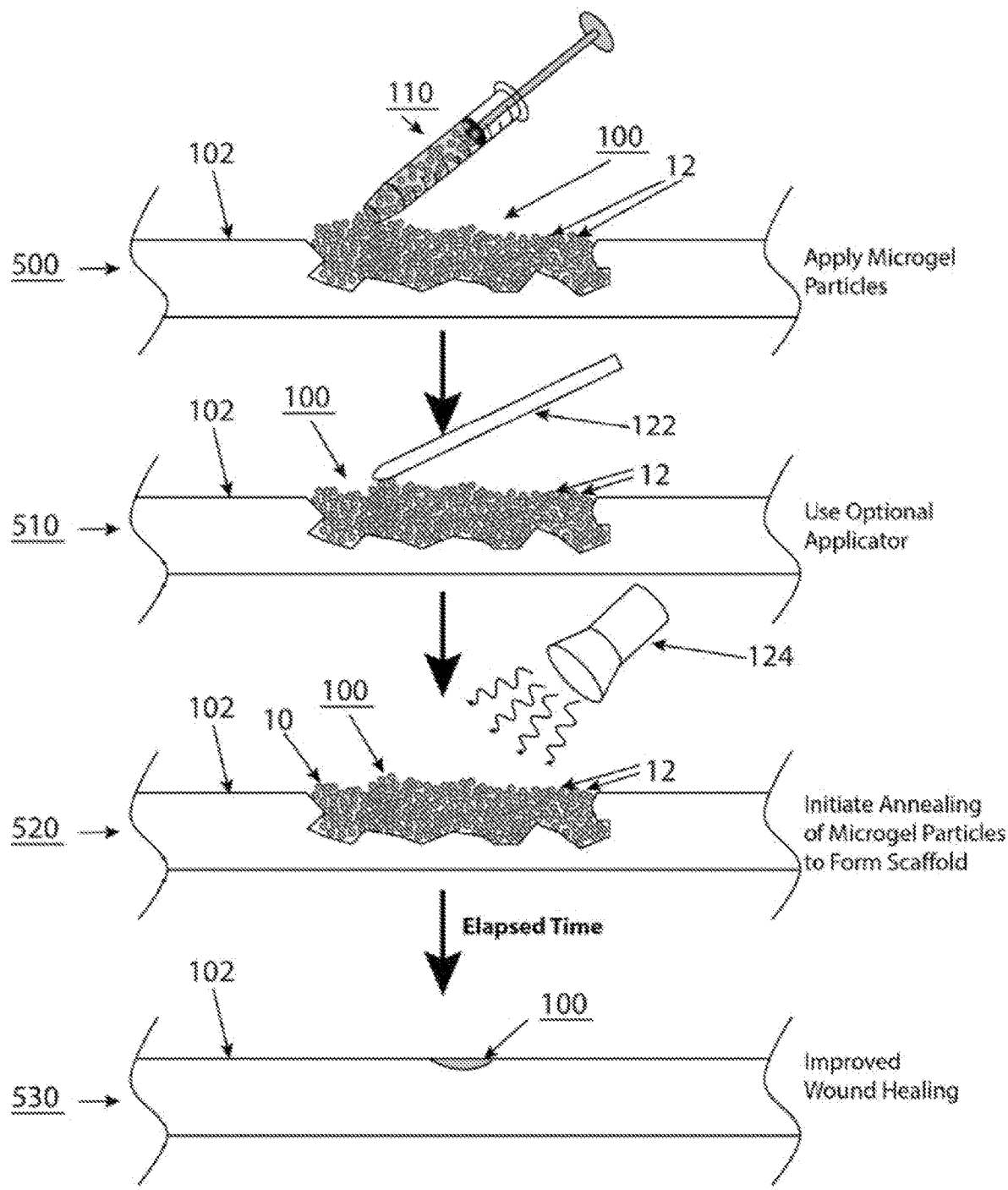
FIG. 11 illustrates an exemplary method of treating damaged tissue using the microporous gel system described herein. Microgel particles are applied (top panel), optionally, an applicator is utilized (second panel), annealing of microgel particles is initiated to form a scaffold (third panel) and improved wound healing is observed (bottom panel).

FIG. 11 illustrates one example of method of treating damaged tissue 102. FIG. 11 illustrates a wound site 100 formed in tissue 102 of a mammal. In operation 500, a delivery device 110 (e.g., tube as illustrated) that contains therein the slurry of microgel particles 12 contained in an aqueous solution is used to deliver the microgel particles 12 to the wound site 100. Next, as seen in operation 510, an optional applicator 122 is used to spread the microgel particles 12 into and over the wound site 100. The applicator 122 is also used to make the upper, exposed surface of the microgel particles 12 generally flush with the surface of the tissue 102. The applicator 122 can also be used to make the upper, exposed surface of the microgel particles 12 mounded or elevated with respect to the surface of the tissue 102 to allow for increased structure for cellular ingrowth and prevention of a depressed tissue interface upon full healing. Next, as seen in operation 520, annealing of the microgel particles 12 is initiated to form the scaffold 10 of annealed microgel particles 12. In this particular example, a light source 124 in the form of a flashlight is used to illuminate a mixture of microgel particles 12, a photoinitiator (e.g., Eosin Y), and a free radical transfer agent (e.g., RGD peptide). Of course, other annealing modalities as described herein may also be used. The annealing reaction illustrated in FIG. 11 causes the formation of a covalently-stabilized scaffold 10 of microgel particles 12 having interstitial spaces therein. Cells 106 (as seen in FIG. 2C) from the surrounding tissue 102 then begin to infiltrate the spaces within the scaffold 10, grow, stimulate, and ultimately effectuate the healing process of the tissue 102. In one embodiment, following the annealing reaction a bandage or moist dressing is optionally placed over the scaffold-filled wound to protect it from damage during the healing process. After a period of elapsed time, as illustrated in operation 530, the scaffold 10 has degraded and the tissue 102 has returned to a healed state.

In order to assess the ability of the porous gel scaffold to support cell growth and network formation, an in vitro cell morphology and proliferation model was developed using three human cell lines: Dermal Fibroblasts (HDF), Adipose-derived Mesenchymal Stem Cells (AhMSC), and Bone Marrow-derived Mesenchymal Stem Cells (BMhMSC). A single-cell suspension was dynamically incorporated within a FXIIIa annealed porous gel scaffold. The three cell lines exhibited high cell viability (≥93%, FIG. 12B) following twenty-four (24) hours of culture within the porous gel scaffold.

Figures 12A, 12B:
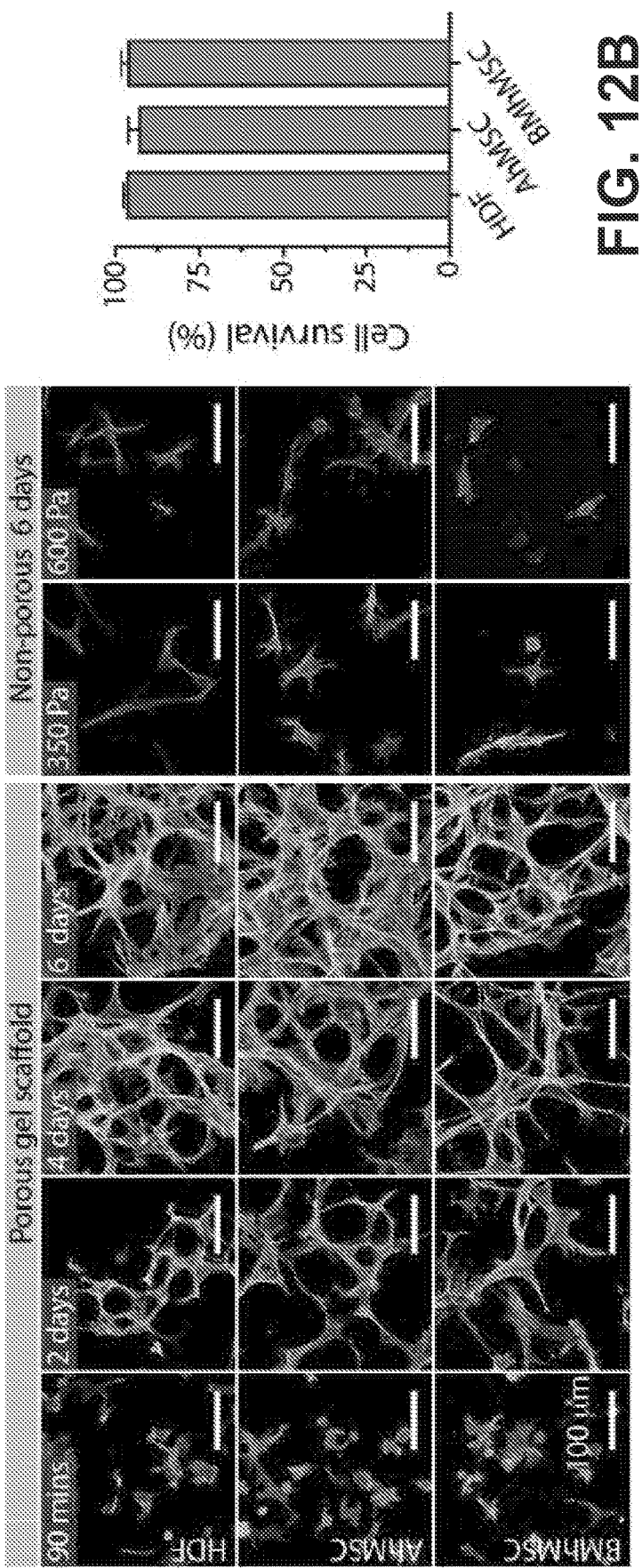
FIG. 12A illustrates fluorescent images demonstrating the formation of 3D cellular networks during six days of culture in porous gel scaffolds in vitro as well as non-porous gels after 6 days. (350 Pa: bulk modulus identical to porous gel scaffolds, 600 Pa: microscale modulus matched to individual microgels).
FIG. 12B illustrates a graph of cell survival twenty-four (24) hours post annealing is greater than 93% across three cell lines representing different human tissue types. HDF: Human dermal fibroblasts, AhMSC: Adipose-derived human mesenchymal stem cells, BMhMSC: Bone marrow-derived human mesenchymal stem cells.

Cells incorporated into the porous gel scaffold began to exhibit spread morphology ninety (90) minutes following the onset of annealing. After two (2) days in culture, all observed cells within the porous gel scaffolds exhibited a completely spread morphology, which continued through day six. Importantly, an extensive network formation for all cell lines was observed by day two. Cell networks increased in size and complexity through the entirety of the experiment. The BMhMSCs were of particular note, as their expansive network formation and slower proliferation rate indicated that these cells were able to spread to extreme lengths, forming highly interconnected cellular networks within the microporous scaffolds as seen in FIG. 12A.

Figure 13A:
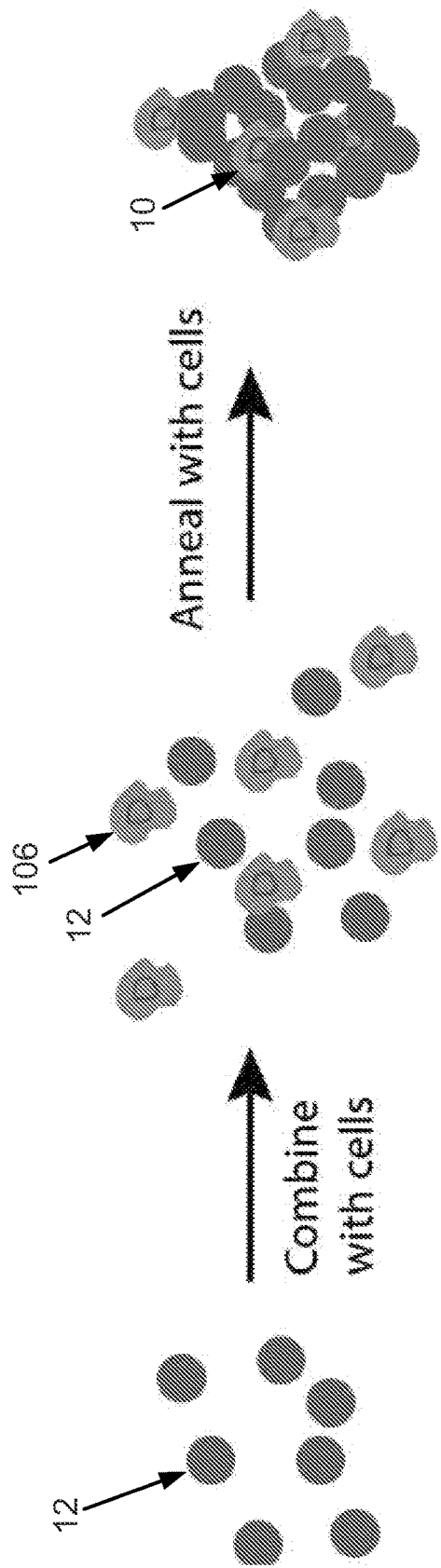
FIG. 13A illustrates an exemplary method for combining living cells with preformed microgel particles prior to annealing. The microgel particles are annealed to one another, entrapping the living cells within the interconnected microporous network created upon microgel annealing.
Figures 13B, 13C, 13D, 13E:
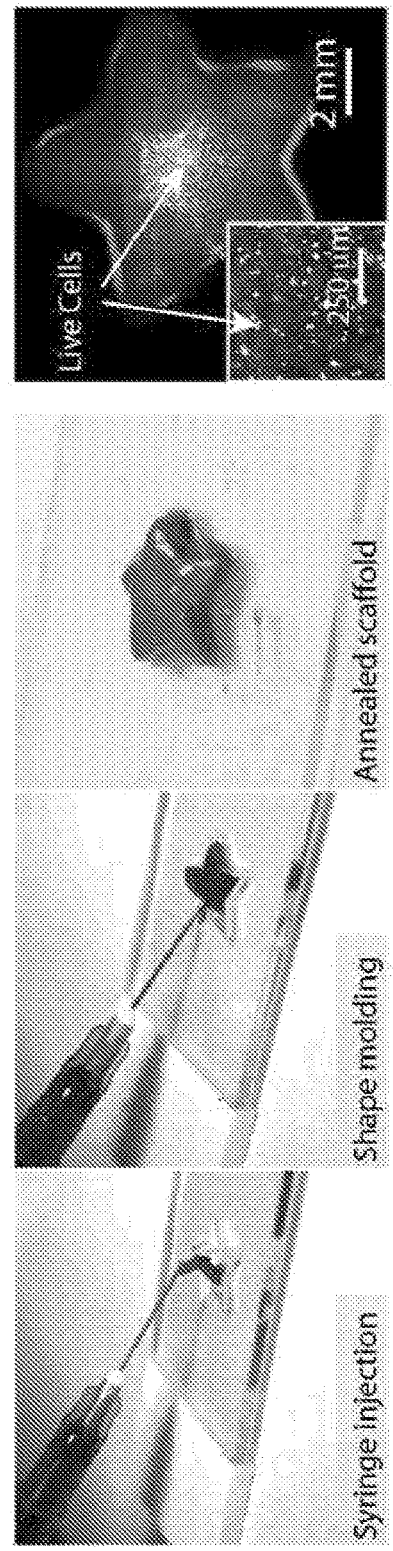
FIGS. 13B-D are photographic images illustrating that microgel particle solutions combined with living cells are moldable to macro-scale shapes, and can be injected to form complex shapes that are maintained after annealing.
FIG. 13E illustrates microgel particles are moldable to macro-scale shapes and can be performed in the presence of live cells (indicated by arrows pointing to fluorescent HEK-293T cells).

The microgel particles 12 can be combined and mixed with a solution of living cells 106 prior to annealing to create a microporous scaffold 10 that contains living cells 106 residing in the microporous network and dispersed either homogenously or heterogeneously within the macroscopic annealed gel scaffold 10 as seen in FIG. 13A.

The microgel particles 12 can be purified into an aqueous solution of isotonic cell culture media for storage and when used to form a porous gel were annealed to one another via a non-canonical amide linkage between the K and Q peptides mediated by activated Factor XIII (FXIIIa), a naturally occurring enzyme responsible for stabilizing blood clots. This enzyme-mediated annealing process, allowed incorporation of living cells 106 into a dynamically forming porous scaffold 10 that contained interconnected microporous networks. Following addition of FXIIIa, but prior to scaffold annealing, a slurry of the microgel particles 12 can be delivered via syringe application (FIG. 13A), ultimately solidifying in the shape of the cavity in which they are injected as seen in FIGS. 13B-E.

Figure 14A:
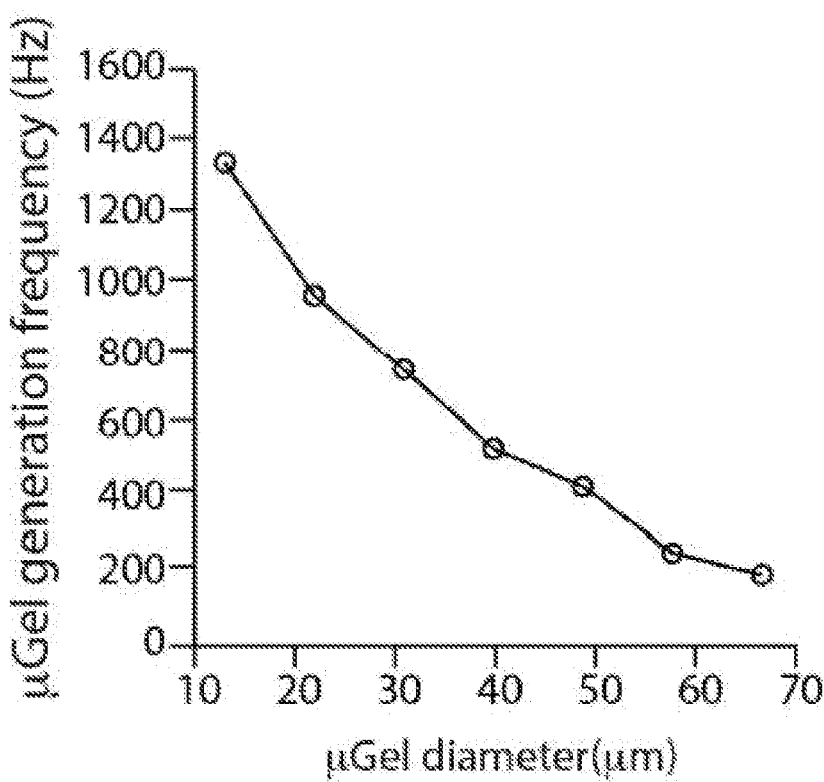
FIG. 14A illustrates a graph showing that varying sizes of microgel particles can be synthesized over a range of frequencies of production in an exemplary embodiment.
Figure 14B:
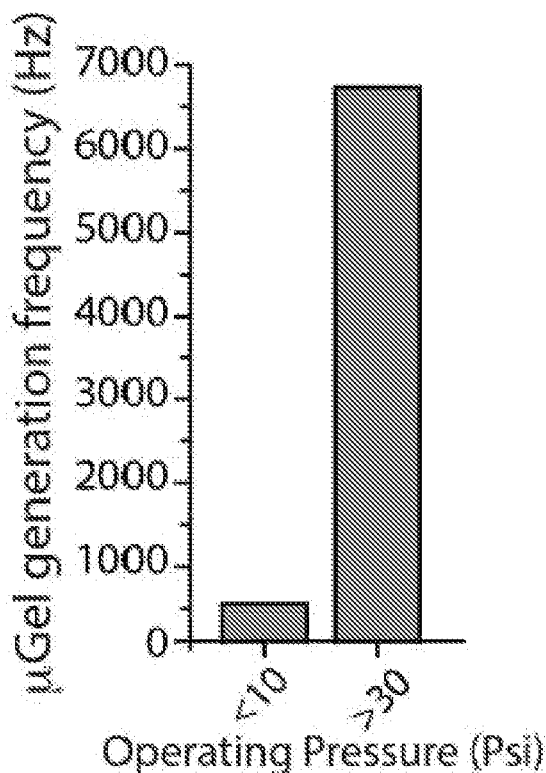
FIG. 14B illustrates that providing a high inlet pressure to each solution inlet (where the oil inlets are exceeding 30 Psi) enables an increase in production frequency in another exemplary embodiment.
Figure 14C:
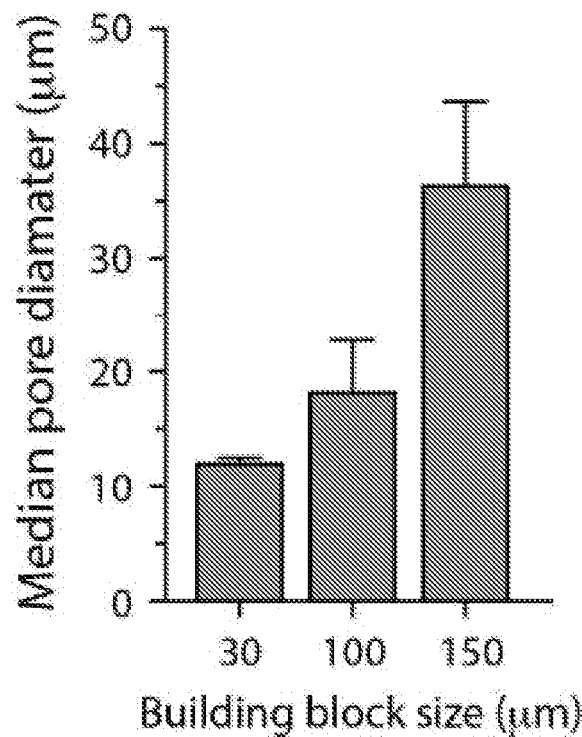
FIG. 14C illustrates a graph showing high precision fabrication of microgel building blocks allows creation of defined gel scaffolds. Different building block sizes allow for deterministic control over resultant micro-porous network characteristics, presented here as median pore sizes +/− standard deviation (SD).

Microfluidic fabrication of the microgel particles 12 enables deterministic control over the microgel size and production frequency as illustrated in FIG. 14A. The pressure that is applied to the inlets of the microfluidic system 20, determines the frequency of microgel production (FIG. 14B). Further, porous microgel scaffolds 10 created using different size microgel particles 12 have distinct porous characteristics, such as the median pore size within the network as seen in FIG. 14C.

While embodiments have been shown and described, various modifications may be made without departing from the scope of the inventive concepts disclosed herein. The subject matter described herein, therefore, should not be limited, except to the following claims, and their equivalents.

---

What is claimed is:

1. A method of delivering to living mammalian tissue a covalently-stabilized porous scaffold of spherical microgel particles comprising:
   (a) delivering to the living mammalian tissue a plurality of flowable, spherical microgel particles comprising diameters between 10 micrometers to 1000 micrometers, the plurality of flowable, spherical microgel particles comprising a cross-linked poly(ethylene glycol) (PEG) backbone polymer cross-linked with a matrix metalloprotease (MMP)-degradable crosslinker and an annealing component comprising K-peptides and Q-peptides and a cell-adhesive peptide comprising RGD; and
   (b) following delivery in (a) exposing the flowable, spherical microgel particles to an annealing agent comprising Factor XIIIa that links the flowable, spherical microgel particles together via a covalent annealing reaction at points of physical contact between adjacent spherical microgel particles via the K peptides and Q-peptides to form the covalently-stabilized porous scaffold, wherein the covalently-stabilized porous scaffold comprises pores with a median diameter of about 10 to about 35 micrometers into which cells from the living mammalian tissue become integrated within forty-eight hours of exposing in (b).

* * * * *